(12) United States Patent
Burgey et al.

(10) Patent No.: US 7,491,713 B2
(45) Date of Patent: Feb. 17, 2009

(54) CGRP RECEPTOR ANTAGONISTS

(75) Inventors: Christopher S. Burgey, Philadelphia, PA (US); Daniel V. Paone, Lansdale, PA (US); Anthony W Shaw, Harleysville, PA (US); Craig A. Stump, Pottstown, PA (US); Theresa M. Williams, Harleysville, PA (US)

(73) Assignee: Merck + Co., Inc., Rahway, NJ (US)

( * ) Notice: Subject to any disclaimer, the term of this patent is extended or adjusted under 35 U.S.C. 154(b) by 0 days.

(21) Appl. No.: 10/587,121

(22) PCT Filed: Jan. 25, 2005

(86) PCT No.: PCT/US2005/002199

§ 371 (c)(1), (2), (4) Date: May 14, 2007

(87) PCT Pub. No.: WO2005/072308

PCT Pub. Date: Aug. 11, 2005

(65) Prior Publication Data

US 2007/0287696 A1   Dec. 13, 2007

Related U.S. Application Data

(60) Provisional application No. 60/539,957, filed on Jan. 29, 2004.

(51) Int. Cl.
C07D 401/14 (2006.01)
C07D 413/14 (2006.01)
C07D 417/14 (2006.01)
A61K 31/4178 (2006.01)
A61K 31/4439 (2006.01)
A61K 31/551 (2006.01)
A61K 31/553 (2006.01)
A61K 31/554 (2006.01)
A61P 25/06 (2006.01)

(52) U.S. Cl. .............. 514/211.03; 514/212.06; 514/218; 514/318; 514/326; 540/488; 540/492; 540/524; 546/193; 546/208; 546/210

(58) Field of Classification Search ............. 540/488, 540/492, 524; 546/187, 193, 208, 210; 514/211.03, 514/211.08, 212.08, 218, 318, 326
See application file for complete search history.

*Primary Examiner*—Bruck Kifle
(74) *Attorney, Agent, or Firm*—William Krovatin; John Todaro

(57) ABSTRACT

Compounds of Formula I:

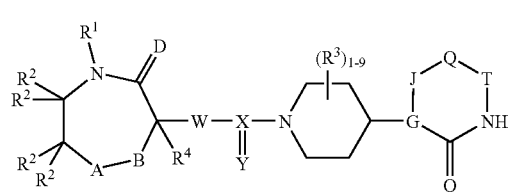

and Formula II:

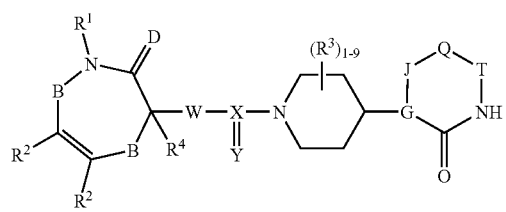

(where variables $R^1$, $R^2$, $R^3$, $R^4$, A, B, D, G, J, Q, T, W, X and Y are as defined herein) useful as antagonists of CGRP receptors and useful in the treatment or prevention of diseases in which the CGRP is involved, pharmaceutical compositions comprising these compounds, use of these compounds and compositions to prevent or treat diseases involving CGRP.

12 Claims, No Drawings

CGRP RECEPTOR ANTAGONISTS

RELATED APPLICATION DATA

This is a National filing under 35 U.S.C 371 of PCT/US. 2005/002199, filed Jan. 25, 2005, which claims priority from USSN 60/539,957, filed Jan. 29, 2004.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human $\square$-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, asthma (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of Formula I:

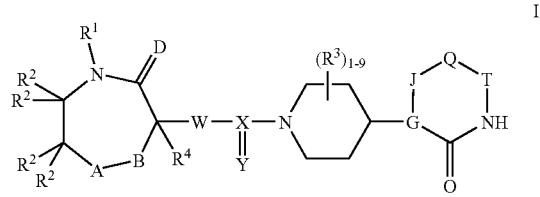

and Formula II:

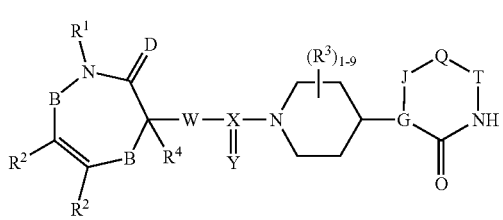

(where variables $R^1$, $R^2$, $R^3$, $R^4$, A, B, D, G, J, Q, T, W, X and Y are as defined herein) useful as antagonists of CGRP receptors and useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to CGRP antagonists which include compounds of Formula I:

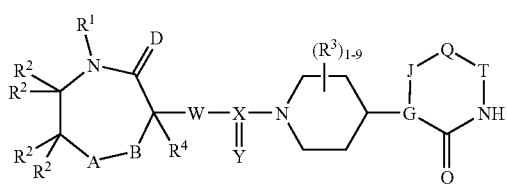

and Formula II:

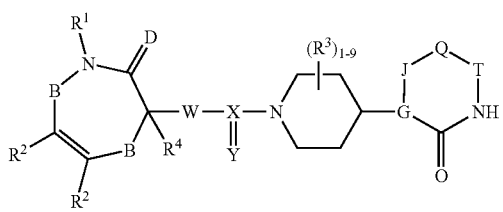

wherein:

A is a bond, $C(R^2)_2$, O, $S(O)_m$ or $NR^2$;

B is $(C(R^2)_2)_n$;

D is O;

$R^1$ is selected from:
1) H, $C_1$-$C_6$ alkyl, $C_2$-$C_6$ alkenyl, $C_2$-$C_6$ alkynyl, $C_{3-6}$ cycloalkyl, and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2 NR^{10}R^{11}$,
   q) $N(R^{10})SO_2 R^{11}$,
   r) $S(O)_m R^{10}$,
   s) CN,
   t) $NR^{10}R^{11}$,
   u) $N(R^{10})(CO)NR^4 R^{11}$, and,
   v) $O(CO)R^4$;
2) aryl or heteroaryl, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2 NR^{10}R^{11}$,
   q) $N(R^{10})SO_2 R^{11}$,
   r) $S(O)_m R^{10}$,
   s) CN,
   t) $NR^{10}R^{11}$,
   u) $N(R^{10})(CO)NR^4 R^{11}$, and
   v) $O(CO)R^4$;

$R^2$ is independently selected from:
1) H, $C_0$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$, e) heterocycle, unsubstituted or substituted with 1-5 substituents where the substituents are independently selected from $R^4$,
f) $(F)_pC_{1-3}$ alkyl,
g) halogen,
h) $OR^4$,
i) $O(CH_2)_sOR^4$,
j) $CO_2R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$, and,
v) $O(CO)R^4$; and 2) aryl or heteroaryl, unsubstituted or substituted with one or more substituents independently selected from:
a) $C_{1-6}$ alkyl,
b) $C_{3-6}$ cycloalkyl,
c) aryl, unsubstituted or substituted with 1-5 substituents where the substituents are independently selected from $R^4$,
d) heteroaryl, unsubstituted or substituted with 1-5 substituents where the substituents are independently selected from $R^4$,
e) heterocycle, unsubstituted or substituted with 1-5 substituents where the substituents are independently selected from $R^4$,
f) $(F)_pC_{1-3}$ alkyl,
g) halogen,
h) $OR^4$,
i) $O(CH_2)_sOR^4$,
j) $CO_2R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$, and
v) $O(CO)R^4$;

or, any two independent $R^2$ on the same carbon or on adjacent carbons may be joined together to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, where said ring is unsubstituted or substituted with 1-5 substituents independently selected from:
(a) —$C_{1-6}$alkyl, which is unsubstituted or substituted with 1-3 substituents independently selected from:
(i) halo,
(ii) hydroxy,
(iii) —O—$C_{1-6}$alkyl,
(iv) —$C_{3-6}$cycloalkyl,
(v) —$COR^{10}$,
(vi) —$CO_2R^{10}$,
(vii) —$NR^{10}R^{11}$,
(viii) —$SO_2R^{10}$,
(ix) —$CONR^{10}R^{11}$, and
(x) —$(NR^{10})CO_2R^{11}$,
(b) —$SO_2NR^{10}R^{11}$
(c) halo,
(d) —$SO_2R^{10}$,
(e) hydroxy,
(f) —O—$C_{1-6}$alkyl, which is unsubstituted or substituted with 1-5 halo,
(g) —CN,
(h) —$COR^{10}$,
(i) —$NR^{10}R^{11}$,
(j) —$CONR^{10}R^{11}$,
(k) —$CO_2R^{10}$,
(l) —$(NR^{10})CO_2R^{11}$,
(m) —$O(CO)NR^{10}R^{11}$,
(n) —$(NR^4)(CO)NR^{10}R^{11}$, and
(o) oxo;

$R^{10}$ and $R^{11}$ are independently selected from: H, $C_{1-6}$ alkyl, $(F)_pC_{1-6}$ alkyl, $C_{3-6}$ cycloalkyl, aryl, heteroaryl, and benzyl, unsubstituted or substituted with halogen, hydroxy or $C_1$-$C_6$ alkoxy, where $R^{10}$ and $R^{11}$ may be joined together to form a ring selected from: azetidinyl, pyrrolidinyl, piperidinyl, piperazinyl, or morpholinyl, which is unsubstituted or substituted with 1-5 substituents where the substituents are independently selected from $R^4$;

$R^4$ is independently selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;

X is C or S;

Y is O, $(R^4)_2$, NCN, $NSO_2CH_3$ or $NCONH_2$, or Y is $O_2$ when X is S;

$R^5$ is independently selected from H and:
1) $C_1$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
a) $C_{1-6}$ alkyl,
b) $C_{3-6}$ cycloalkyl,
c) aryl, unsubstituted or substituted with 1-5 substituents where the substituents are independently selected from $R^4$,
d) heteroaryl, unsubstituted or substituted with 1-5 substituents where the substituents are independently selected from $R^4$,
e) heterocycle, unsubstituted or substituted with 1-5 substituents where the substituents are independently selected from $R^4$,
f) $(F)_pC_{1-3}$ alkyl,
g) halogen,
h) $OR^4$,
i) $O(CH_2)_sOR^4$,
j) $CO_2R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$, p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$, and,
v) $O(CO)R^4$;

2) aryl or heteroaryl, unsubstituted or substituted with one or more substituents independently selected from:
  a) $C_{1-6}$ alkyl,
  b) $C_{3-6}$ cycloalkyl,
  c) aryl, unsubstituted or substituted with 1-5 substituents where the substituents are independently selected from $R^4$,
  d) heteroaryl, unsubstituted or substituted with 1-5 substituents where the substituents are independently selected from $R^4$,
  e) heterocycle, unsubstituted or substituted with 1-5 substituents where the substituents are independently selected from $R^4$,
  f) $(F)_pC_{1-3}$ alkyl,
  g) halogen,
  h) $OR^4$,
  i) $O(CH_2)_sOR^4$,
  j) $CO_2R^4$,
  k) $(CO)NR^{10}R^{11}$,
  l) $O(CO)NR^{10}R^{11}$,
  m) $N(R^4)(CO)NR^{10}R^{11}$,
  n) $N(R^{10})(CO)R^{11}$,
  o) $N(R^{10})(CO)OR^{11}$,
  p) $SO_2NR^{10}R^{11}$,
  q) $N(R^{10})SO_2R^{11}$,
  r) $S(O)_mR^{10}$,
  s) CN,
  t) $NR^{10}R^{11}$,
  u) $N(R^{10})(CO)NR^4R^{11}$, and
  v) $O(CO)R^4$;
3) $C_{1-6}$ alkyl,
4) $C_{3-6}$ cycloalkyl,
5) heterocycle, unsubstituted or substituted with 1-5 substituents where the substituents are independently selected from $R^4$,
6) $(F)_pC_{1-3}$ alkyl,
7) halogen,
8) $OR^4$,
9) $O(CH_2)_sOR^4$,
10) $CO_2R^4$,
11) $(CO)NR^{10}R^{11}$,
12) $O(CO)NR^{10}R^{11}$,
13) $N(R^4)(CO)NR^{10}R^{11}$,
14) $N(R^{10})(CO)R^{11}$,
15) $N(R^{10})(CO)OR^{11}$,
16) $SO_2NR^{10}R^{11}$,
17) $N(R^{10})SO_2R^{11}$,
18) $S(O)_mR^{10}$,
19) CN,
20) $N^{10}R^{11}$,
21) $N(R^{10})(CO)NR^4R^{11}$, and,
22) $O(CO)R^4$, or two $R^5$ attached to the same carbon form the substituent =O, such that $C(R^5)_2$ may be C=O, where the number of $R^5$ substituents that are not H, can range from zero to three;

$R^6$ is independently selected from: H, $C_{1-6}$ alkyl, $(F)_pC_{1-6}$ alkyl, $C_{3-6}$ cycloalkyl, aryl, heteroaryl and benzyl, unsubstituted or substituted with
  a) $(F)_pC_{1-3}$ alkyl,
  b) halogen,
  c) $OR^4$,
  d) $O(CH_2)_sOR^4$,
  e) $CO_2R^4$,
  f) $(CO)NR^{10}R^{11}$,
  g) $O(CO)NR^{10}R^{11}$,
  h) $N(R^4)(CO)NR^{10}R^{11}$,
  i) $N(R^{10})(CO)R^{11}$,
  j) $N(R^{10})(CO)OR^{11}$,
  k) $SO_2NR^{10}R^{11}$,
  l) $N(R^{10})SO_2R^{11}$,
  m) $S(O)_mR^{10}$,
  n) CN,
  o) $NR^{10}R^{11}$,
  p) $N(R^{10})(CO)NR^4R^{11}$, and
  q) $O(CO)R^4$;

G-J is selected from: N, $C(R^5)$, $C=C(R^5)$, $N-C(R^5)_2$, C=N, $C(R^5)-C(R^5)_2$, $C(R^5)-N(R^6)$, and $N-N(R^6)$;

Q-T is selected from: $C(R^5)_2-C(R^5)_2$, $C(R^5)=C(R^5)$, $N=C(R^5)$, $C(R^5)=N$, N=N, $N(R^6)$, $C(R^5)_2-(C=O)$, $N(R^6)-(C=O)$, and $C(R^5)_2-N(R^6)$;

$R^3$ is independently selected from H, substituted or unsubstituted $C_1-C_3$ alkyl, CN, F, $OR^4$ and $CO_2R^4$;

p is 0 to 2q+1, for a substituent with q carbons;

m is 0, 1 or 2;

n is 0 or 1;

s is 1, 2 or 3;

and pharmaceutically acceptable salts and individual diastereomers thereof.

Further embodiments of the invention are CGRP antagonists of Formula I which include compounds of the Formula Ia:

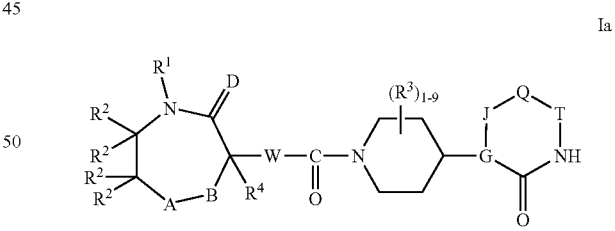

Ia wherein:

A is a bond, $C(R^2)_2$, O, $S(O)_m$ or $NR^2$;

B is $(C(R^2)_2)_n$;

D is O;

n is 0 or 1; and $R^1$, $R^2$, $R^4$, W, $R^3$, G-J, Q-T, and m are as defined in Formula I;

and pharmaceutically acceptable salts and individual stereoisomers thereof.

Still further embodiments of the invention are CGRP antagonists of Formula I which include compounds of the Formula Ib:

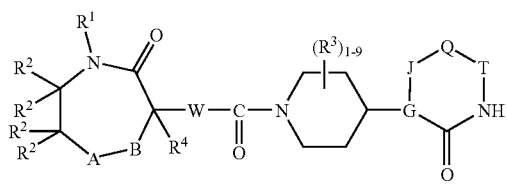

wherein:

A is a bond, $C(R^2)_2$, O, $S(O)_m$ or $NR^2$;

B is $(C(R^2)_2)_n$;

n is 0 or 1; and $R^1$, $R^2$, $R^4$, W, $R^3$, G-J, Q-T, and m are as defined in Formula I;

and pharmaceutically acceptable salts and individual stereoisomers thereof.

Additional embodiments of the invention are CGRP antagonists of Formula I which include compounds of the Formula Ic:

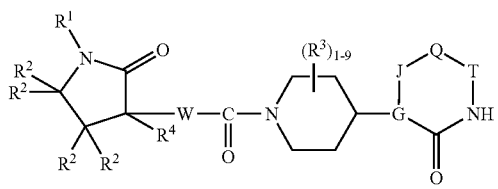

wherein:

$R^1$, $R^2$, $R^4$, W, $R^3$, G-J, Q-T, and m are as defined in Formula I;

and pharmaceutically acceptable salts and individual stereoisomers thereof.

Additional embodiments of the invention are CGRP antagonists of Formula I which also include compounds of the Formula Id:

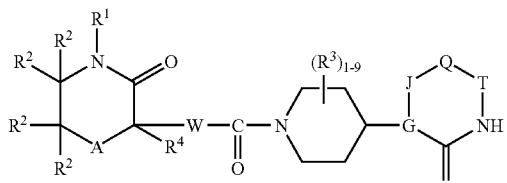

wherein:

A is $C(R^2)_2$, O, $S(O)_m$ or $NR^2$;

$R^1$, $R^2$, $R^4$, W, $R^3$, G-J, Q-T, and m are as defined in Formula I;

and pharmaceutically acceptable salts and individual stereoisomers thereof.

Additional embodiments of the invention are CGRP antagonists of Formula I which include compounds of the Formula Ie:

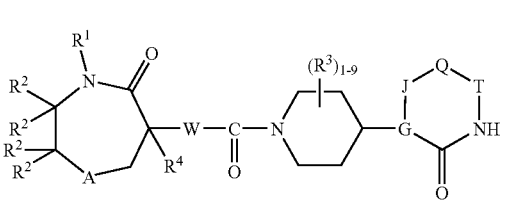

wherein:

A is $C(R^2)_2$, O, $S(O)_m$ or $NR^2$;

$R^1$, $R^2$, $R^4$, W, $R^3$, G-J, Q-T, and m are defined in Formula I;

and pharmaceutically acceptable salts and individual stereoisomers thereof.

Further embodiments of the invention are CGRP antagonists of Formula I, and in particular Formulae Ia-Ie, wherein:

$R^1$ is selected from:

1) H, $C_1$-$C_6$ alkyl, $C_{3-6}$ cycloalkyl and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) CN,
   l) $NR^{10}R^{11}$, and
   m) $O(CO)R^4$; and 2) aryl or heteroaryl, unsubstituted or substituted with one or more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$,
   k) CN,
   l) $NR^{10}R^{11}$, and,
   m) $O(CO)R^4$;

$R^2$ is selected from:
1) H, $C_0$-$C_6$ alkyl, $C_2$-$C_6$ alkynyl, $C_{3-6}$ cycloalkyl and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $S(O)_m R^4$,
   l) CN,
   m) $NR^{10}R^{11}$, and
   n) $O(CO)R^4$; and
2) aryl or heteroaryl, unsubstituted or substituted with one or more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$
   j) $S(O)_m R^4$,
   k) CN,
   l) $NR^{10}R^{11}$, and
   m) $O(CO)R^4$;

or, any two independent $R^2$ on the same carbon or on adjacent carbons may be joined together to form a ring selected from cyclobutyl, cyclopentenyl, cyclopentyl, cyclohexenyl, cyclohexyl, thiazolinyl, oxazolinyl, imidazolinyl, imidazolidinyl, pyrrolinyl, morpholinyl, thiomorpholinyl, thiomorpholinyl S-oxide, thiomorpholinyl S-dioxide, azetidinyl, pyrrolidinyl, piperidinyl, tetrahydrofuranyl, tetrahydropyranyl, tetrahydropyridyl, furanyl, dihydrofuranyl, dihydropyranyl or piperazinyl, where said ring is unsubstituted or substituted with 1-5 substituents independently selected from:
   (a) —$C_{1-6}$alkyl, which is unsubstituted or substituted with 1-3 substituents independently selected from:
      (i) halo,
      (ii) hydroxy,
      (iii) —O—$C_{1-6}$alkyl,
      (iv) —$C_{3-6}$cycloalkyl,
      (v) —$COR^{10}$
      (vi) —$CO_2 R^{10}$,
      (vii) —$NR^{10}R^{11}$,
      (viii) —$SO_2 R^{10}$,
      (ix) —$CONR^{10}R^{11}$, and
      (x) —$(NR^{10})CO_2 R^{11}$,
   (b) —$SO_2 NR^{10}R^{11}$,
   (c) halo,
   (d) —$SO_2 R^{10}$,
   (e) hydroxy,
   (f) —O—$C_{1-6}$alkyl, which is unsubstituted or substituted with 1-5 halo,
   (g) —CN,
   (h) —$COR^{10}$,
   (i) —$NR^{10}R^{11}$,
   (j) —$CONR^{10}R^{11}$,
   (k) —$CO_2 R^{10}$,
   (l) —$(NR^{10})CO_2 R^{10}$,
   (m) —$O(CO)NR^{10}R^{11}$,
   (n) —$(NR^4)(CO)NR^{10}R^{11}$, and
   (o) oxo;

$R^{10}$ and $R^{11}$ are independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ may be joined together to form a ring selected from: azetidinyl, pyrrolidinyl, piperidinyl, piperazinyl and morpholinyl, which is unsubstituted or substituted with 1-5 substituents where the substituents are independently selected from $R^4$ $R^4$ is independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;

G-J is selected from:

N, such that when G-J is so defined, and Q-T is $C(R^5)_2$—$C(R^5)_2$ the following structure forms:

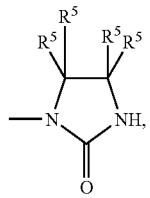

N, such that when G-J is so defined, and Q-T is $C(R^5)$=$C(R^5)$ the following structure forms:

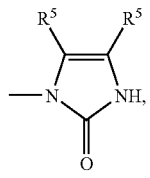

N, such that when G-J is so defined, and Q-T is N=$C(R^5)$ the following structure forms:

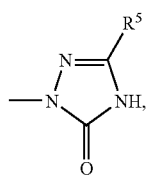

N, such that when G-J is so defined, and Q-T is C(R$^5$)=N the following structure forms:

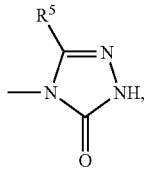

N, such that when G-J is so defined, and Q-T is N=N the following structure forms:

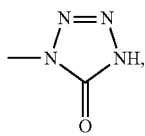

C=C(R$^5$), such that when G-J is so defined, and Q-T is N(R$^6$) the following structure forms:

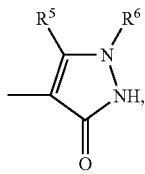

N, such that when G-J is so defined and Q-T is C(R$^5$)$_2$—(C=O) the following structure forms:

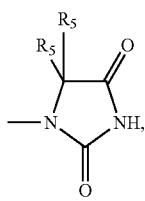

N—C(R$^5$)$_2$, such that when G-J is so defined and Q-T is C(R$^5$)$_2$—C(R$^5$)$_2$ the following structure forms:

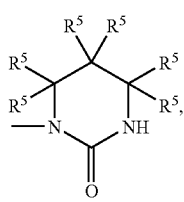

C=C(R$^5$), such that when G-J is so defined and Q-T is C(R$^5$)=C(R$^5$) the following structure forms:

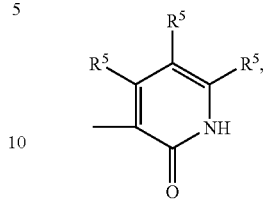

C=C(R$^5$), such that when G-J is so defined and Q-T is C(R$^5$)=N the following structure forms:

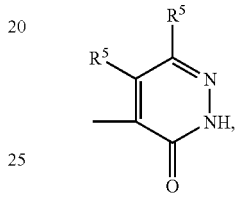

C=C(R$^5$) such that when G-J is so defined and Q-T is N=C(R$^5$) the following structure forms:

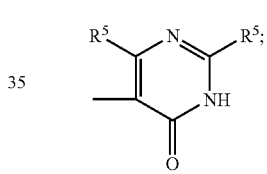

C=N, such that when G-J is so defined and Q-T is C(R$^5$)=C(R$^5$) the following structure forms:

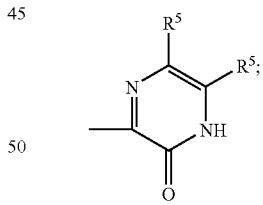

N—C(R$^5$)$_2$, such that when G-J is so defined and Q-T is C(R$^5$)$_2$—(C=O) the following structure forms:

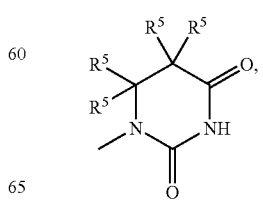

C(R⁵)—C(R⁵)₂, such that when G-J is so defined and Q-T is N(R⁶)—(C=O) the following structure forms:

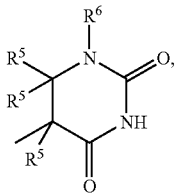

C(R⁵)—C(R⁵)₂, such that when G-J is so defined and Q-T is C(R⁵)₂—C(R⁵)₂ the following structure forms:

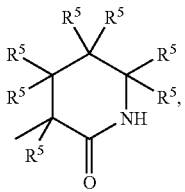

C(R⁵)—C(R⁵)₂, such that when G-J is so defined and Q-T is C(R⁵)₂—N(R⁶) the following structure forms:

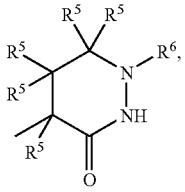

C(R⁵)—N(R⁶), such that when G-J is so defined and Q-T is C(R⁵)₂—C(R⁵)₂ the following structure forms:

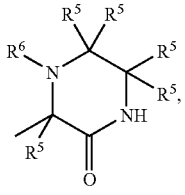

C(R⁵)—C(R⁵)₂, such that when G-J is so defined and Q-T is N=C(R⁵) the following structure forms:

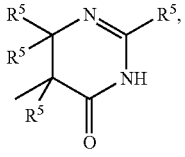

N—C(R⁵)₂, such that when G-J is so defined and Q-T is C(R⁵)₂—N(R⁶) the following structure forms:

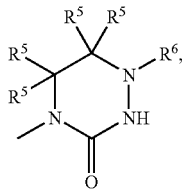

N—N(R⁶), such that when G-J is so defined and Q-T is C(R⁵)₂—C(R⁵)₂ the following structure forms:

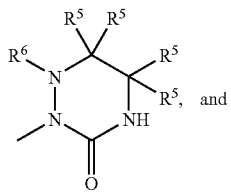

N—C(R⁵)₂, such that when G-J is so defined and Q-T is N=C(R⁵) the following structure forms:

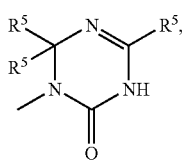

and tautomers;

$R^5$ is independently selected from H and:
1) $C_1$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_pC_{1-3}$ alkyl,
   g) halogen,
   h) $OR^4$,
   i) $O(CH_2)_sOR^4$,
   j) $CO_2R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2NR^{10}R^{11}$, q) $N(R^{10})SO_2R^{11}$,
r) $S(O)_m R^{10}$,
s) CN,
t) $NR^{10}R^{11}$,
u) $N(R^{10})(CO)NR^4R^{11}$, and,
v) $O(CO)R^4$;

2) aryl or heteroaryl, unsubstituted or substituted with one or more substituents independently selected from:
  a) $C_{1-6}$ alkyl,
  b) $C_{3-6}$ cycloalkyl,
  c) aryl, unsubstituted or substituted with 1-5 substituents where the substituents are independently selected from $R^4$,
  d) heteroaryl, unsubstituted or substituted with 1-5 substituents where the substituents are independently selected from $R^4$,
  e) heterocycle, unsubstituted or substituted with 1-5 substituents where the substituents are independently selected from $R^4$,
  f) $(F)_p C_{1-3}$ alkyl,
  g) halogen,
  h) $OR^4$,
  i) $O(CH_2)_s OR^4$,
  j) $CO_2 R^4$,
  k) $(CO)NR^{10}R^{11}$,
  l) $O(CO)NR^{10}R^{11}$,
  m) $N(R^4)(CO)NR^{10}R^{11}$,
  n) $N(R^{10})(CO)R^{11}$,
  o) $N(R^{10})(CO)OR^{11}$,
  p) $SO_2 NR^{10}R^{11}$,
  q) $N(R^{10})SO_2 R^{11}$,
  r) $S(O)_m R^{10}$,
  s) CN,
  t) $NR^{10}R^{11}$,
  u) $N(R^{10})(CO)NR^4R^{11}$, and
  v) $O(CO)R^4$;

3) $C_{1-6}$ alkyl,
4) $C_{3-6}$ cycloalkyl,
5) aryl, unsubstituted or substituted with 1-5 substituents where the substituents are independently selected from $R^4$,
6) heteroaryl, unsubstituted or substituted with 1-5 substituents where the substituents are independently selected from $R^4$, 7) heterocycle, unsubstituted or substituted with 1-5 substituents where the substituents are independently selected from $R^4$,
8) $(F)_p C_{1-3}$ alkyl,
9) halogen,
10) $OR^4$,
11) $O(CH_2)_s OR^4$,
12) $CO_2 R^4$,
13) $(CO)NR^{10}R^{11}$,
14) $O(CO)NR^{10}R^{11}$,
15) $N(R^4)(CO)NR^{10}R^{11}$,
16) $N(R^{10})(CO)R^{11}$,
17) $N(R^{10})(CO)OR^{11}$,
18) $SO_2 NR^{10}R^{11}$,
19) $N(R^{10})SO_2 R^{11}$,
20) $S(O)_m R^{10}$,
21) CN,
22) $NR^{10}R^{11}$,
23) $N(R^{10})(CO)NR^4R^{11}$, and
24) $O(CO)R^4$, or two $R^5$ attached to the same carbon form the substituent =O, such that $C(R^5)_2$ may be C=O, where the number of $R^5$ substituents that are not H, can range from zero to three;

$R^3$ is independently selected from H, substituted or unsubstituted $C_1-C_3$ alkyl, CN and $CO_2R^4$;

p is 0 to 2q+1, for a substituent with q carbons;

m is 0 to 2;

s is 1 to 3;

and pharmaceutically acceptable salts and individual stereoisomers thereof.

Further embodiments of the present invention include those wherein G-J is selected from N, C=C($R^5$), N—C($R^5$)$_2$ and C=N, and wherein Q-T is selected from C($R^5$)=C($R^5$)$_2$, C($R^5$)$_2$—C($R^5$)$_2$, N=C($R^5$), C($R^5$)=N, N=N, N($R^6$) and C($R^5$)$_2$=(C=O).

It is to be understood that where one or more of the above recited structures or substructures recite multiple substituents having the same designation each such variable may be the same or different from each similarly designated variable. For example, $R^2$ is recited four times in Formula I, and each $R^2$ in Formula I may independently be any of the substructures defined under $R^2$. The invention is not limited to structures and substructures wherein each $R^2$ must be the same for a given structure. The same is true with respect to any variable appearing multiple time in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not all of the $R^{10}$ and $R^{11}$ substituents are capable of forming a ring structure. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear, branched and cyclic structures having no double or triple bonds. Thus $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl and hexyl. "Cycloalkyl" is an alkyl, part or all of which forms a ring of three or more atoms. $C_0$ or $C_0$alkyl is defined to identify the presence of a direct covalent bond.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. Thus $C_{2-6}$alkynyl is defined to identify the group as having 2, 3, 4, 5 or 6 carbons in a linear or branched arrangement, such that $C_{2-6}$alkynyl specifically includes 2-hexynyl and 2-pentynyl.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The number of certain variables present in certain instances is defined in terms of the number of carbons present. For example, variable "p" is occasionally defined as follows: "p is 0 to 2q+1, for a substituent with q carbons". Where the substituent is "$(F)_pC_{1-3}$ alkyl" this means that when there is one carbon, there are 2(1)+1=3 fluorines. When there are two carbons, there are 2(2)+1=5 fluorines, and when there are three carbons there are 2(3)=1=7 fluorines.

When variables G and J are presented or depicted as "G-J" this indicates that G and J together represent a particular moiety. G-J may represent a single ring atom or various arrangements of multiple ring atoms. For instance, G-J is at times herein defined as the single ring atom N, and is at other times defined as multiple ring atoms C=C($R^5$), C=N, and so forth. Similarly, when variables Q and T are presented or depicted as "Q-T" this indicates that these variables together represent a particular moiety. Here, Q-T may represent various arrangements of multiple ring atoms, for instance $C(R^5)_2$—$C(R^5)_2$, N=C($R^5$), C($R^5$)=N, N=N, N and $C(R^5)_2$=(C=O), among others.

It is understood that fused rings formed by $R^2$ groups on adjacent carbon atoms are necessarily limited by the nature of the bond between the adjacent carbon atoms. Thus, where adjacent carbon atoms are double bonded, a fused ring formed by $R^2$ groups on these adjacent carbon atoms must of course include a carbon-carbon double bond, for instance cyclopentenyl, cyclohexenyl, phenyl, naphthyl, thienyl, thiazolyl, thiazolinyl, oxazolyl, oxazolinyl, imidazolyl, imidazolinyl, pyridyl, pyrimidyl, pyrazinyl, pyrrolyl, pyrrolinyl, tetrahydropyridyl, furanyl, dihydrofuranyl and dihydropyranyl.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 □g) were incubated in 1 ml of binding buffer [10 mM HEPES, pH 7.4, 5 mM $MgCl_2$ and 0.2% bovine serum albumin (BSA)] containing 10 pM $^{125}$I-CGRP and inhibitor. After incubation at room temperature for 3 h, the assay was terminated by filtration through GFB glass fibre filter plates (Millipore) that had been blocked with 0.5% polyethyleneimine for 3 h. The filters were washed three times with ice-cold assay buffer, then the plates were air dried. Scintillation fluid (50 l) was added and the radioactivity was counted on a Topcount (Packard Instrument). Data analysis was carried out by using Prism and the $K_i$ was determined by using the Cheng-Prusoff equation (Cheng & Prusoff (1973) *Biochem. Pharmacol.* 22, 3099-3108).

FUNCTIONAL ASSAY: SK-N-MC cells were grown in minimal essential medium (MEM) supplemented with 10% fetal bovine serum, 2 mM L-glutamine, 0.1 mM non-essential amino acids, 1 mM sodium pyruvate, 100 units/ml penicillin and 100 g/ml streptomycin at 37° C., 95% humidity, and 5% $CO_2$. For cAMP assays, cells were plated at $5 \times 10^5$ cells/well in 96-well poly-D-lysine-coated plates (Becton-Dickinson) and cultured for ~18 h before assay. Cells were washed with phosphate-buffered saline (PBS, Sigma) then pre-incubated with 300 M isobutylmethylxanthine in serum-free MEM for 30 min at 37° C. —CGRP-(8-37) was added and the cells were incubated for 10 min before the addition of CGRP. The incubation was continued for another 15 min, then the cells were washed with PBS and processed for cAMP determination according to the manufacturer's recommended protocol. Maximal stimulation over basal was defined by using 100 nM CGRP. Dose-response curves were generated by using Prism. Dose-ratios (DR) were calculated and used to construct full Schild plots (Arunlakshana & Schild (1959) *Br. J. Pharmacol.* 14, 48-58).

In particular, the compounds of the following examples had activity as antagonists of the CGRP receptor in the aforementioned assays, generally with a $K_i$ or $IC_{50}$ value of less than about 50 □M. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; asthma; shock; sepsis; opiate withdrawal syndrome; morphine tolerance; hot flashes in men and women; allergic dermatitis; encephalitis; brain trauma; epilepsy; neurodegenerative diseases; skin diseases; neurogenic cutaneous redness, skin rosaceousness and erythema; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of the invention or the other drugs may have utility, where the combination of the drugs together are safer or more effective than either drug alone. Such other drug(s) may be administered, by a route and in an amount commonly used therefor, contemporaneously or sequentially with inventive compounds. When an inventive compound is used contemporaneously with one or more other drugs, a pharmaceutical composition in unit dosage form containing such other drugs and the inventive compound may be used. However, the combination therapy may also include therapies in which the inventive sompounds and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to an inventive compound or compounds.

For example, the present compounds may be used in conjunction with an anti-inflammatory or analgesic agent or an anti-migraine agent, such as an ergotamine or 5-HT$_1$ agonists, especially a 5-HT$_{1B/1D}$ agonist, for example sumatriptan, naratriptan, zolmitriptan, eletriptan, almotriptan, frovatriptan, donitriptan, and rizatriptan; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as aspirin, ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or a steroidal analgesic. Similarly, the instant compounds may be administered with a pain reliever such as acetaminophen, phenacetin, codeine, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; a tricyclic antidepressant, for example amitriptyline, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with ergot alkaloids, for example ergotamine, ergonovine, ergonovine, methylergonovine, metergoline, ergoloid mesylates, dihydroergotamine, dihydroergocornine, dihydroergocristine, dihydroergocryptine, dihydro-I-ergocryptine, dihydro-ϑ-ergocryptine, ergotoxine, ergocornine, ergocristine, ergocryptine, I-ergocryptine, ϑ-ergocryptine, ergosine, ergostane, bromocriptine, or methysergide.

Additionally, the present compounds may be used in conjunction with a beta-adrenergic antagonist such as timolol, propanolol, atenolol, or nadolol, and the like; a MAO inhibitor, for example phenelzine; a calcium channel blocker, for example flunarizine, nimodipine, lomerizine, verapamil, nifedipine, prochlorperazine or gabapentin; neuroleptics such as olanzapine and quetiapine; an anticonvulsant such as topiramate, zonisamide, tonabersat, carabersat or divalproex sodium; an angiotensin II antagonist, for example losartan and candesartan cilexetil; an angiotensin converting enzyme inhibitor such as lisinopril; or botulinum toxin type A.

The present compounds may be used in conjunction with a potentiator such as caffeine, an H2-antagonist, simethicone, aluminum or magnesium hydroxide; a decongestant such as phenylephrine, phenylpropanolamine, pseudoephedrine, oxymetazoline, epinephrine, naphazoline, xylometazoline, propylhexedrine, or levo-desoxy-ephedrine; an antitussive such as codeine, hydrocodone, caramiphen, carbetapentane, or dextromethorphan; a diuretic; a prokinetic agent such as metoclopramide or domperidone, and a sedating or non-sedating antihistamine.

In one embodiment the present compounds are used in conjunction with an anti-migraine agent, such as: an ergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan and rizatriptan; and a cyclooxygenase inhibitor, such as a selective cyclooxygenase-2 inhibitor, in particular, rofecoxib, etoricoxib, celecoxib, meloxicam, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is possible. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood; however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

The synthesis of the lactams and 4-heteroarylpiperidine intermediates may be conducted as described in Schemes 1-15.

Reaction Schemes

The preparation of final compounds proceeds through intermediates such as those of Formula III and Formula IV, and the synthesis of each intermediate is described herein.

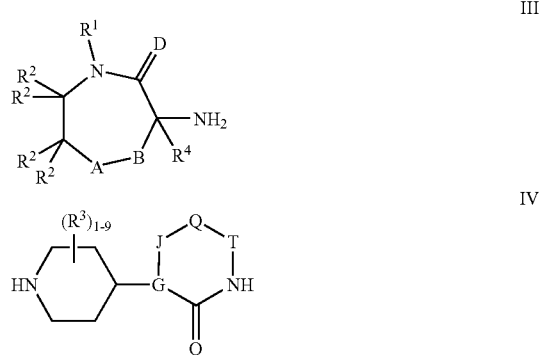

In general, intermediates of the Formulae III and IV can be coupled through a urea linkage as shown in Scheme 1. Amine intermediate 1 can be converted to a reactive carbamate, for example p-nitrophenylcarbamate 2, which is subsequently reacted with an amine like that of intermediate 3 to produce urea 4. Other activated intermediates known to those skilled in the art can be used to prepare compounds like 4. For example, amine 1 can be directly acylated with the appropriate carbamoyl chloride.

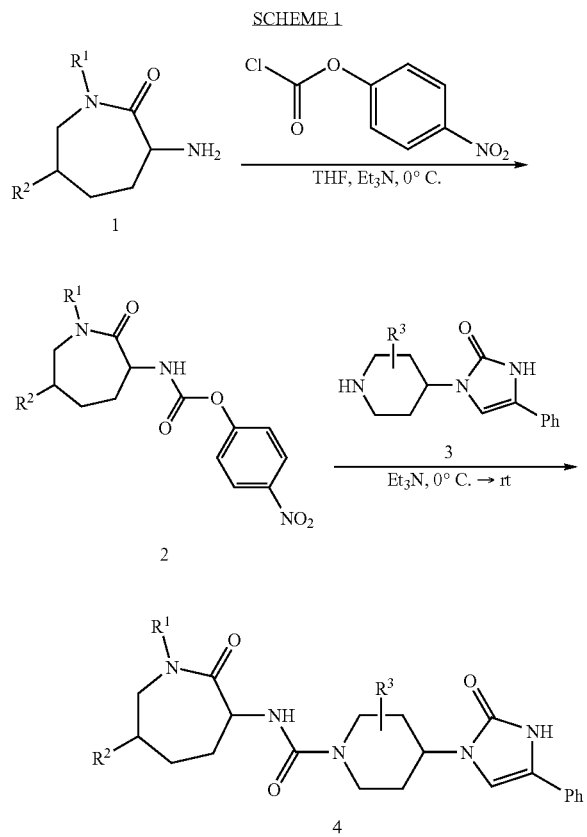

The synthesis of compounds represented by 3 can be accomplished by procedures similar to those described in U.S. Pat. No. 6,344,449 and references cited therein.

Additionally, the synthesis of compounds represented by 11 can be accomplished according to Scheme 2. For example, a 4-piperidinone 5 can be reductively aminated with a carbazate which, after reduction of hydrazone 6, gives the monalkylated product 7. Deprotection to afford hydrazine 8 and condensation/ring closure with a benzothioyl carbamate such as 9 furnishes triazolinone 10. Final deprotection under standard conditions gives the product 11.

Commercially available lactam 12 can be selectively alkylated with a variety of electrophiles such as alkyl bromides to give amide 13 (Scheme 3). Removal of the protective group under acidic conditions affords amines of the general formula 14.

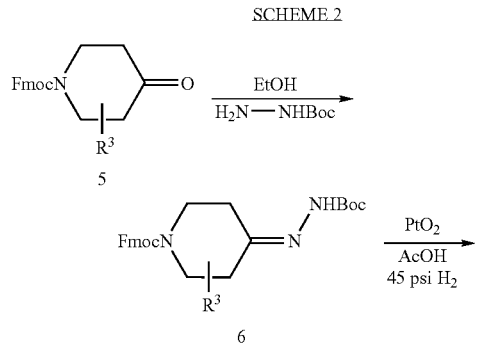

Lactam 15 (Scheme 4) can be prepared according to known procedures (J. Med. Chem., 1988, 31, 422-428). After bromination and displacement with sodium azide, hydrogenation under standard conditions yields amine 18. Protection of the primary amine allows for selective alkylation of the amide nitrogen with various electrophiles, for example alkyl bromides, and deprotection and of the primary amine can be accomplished under acidic conditions, affording compounds of the general formula 21.

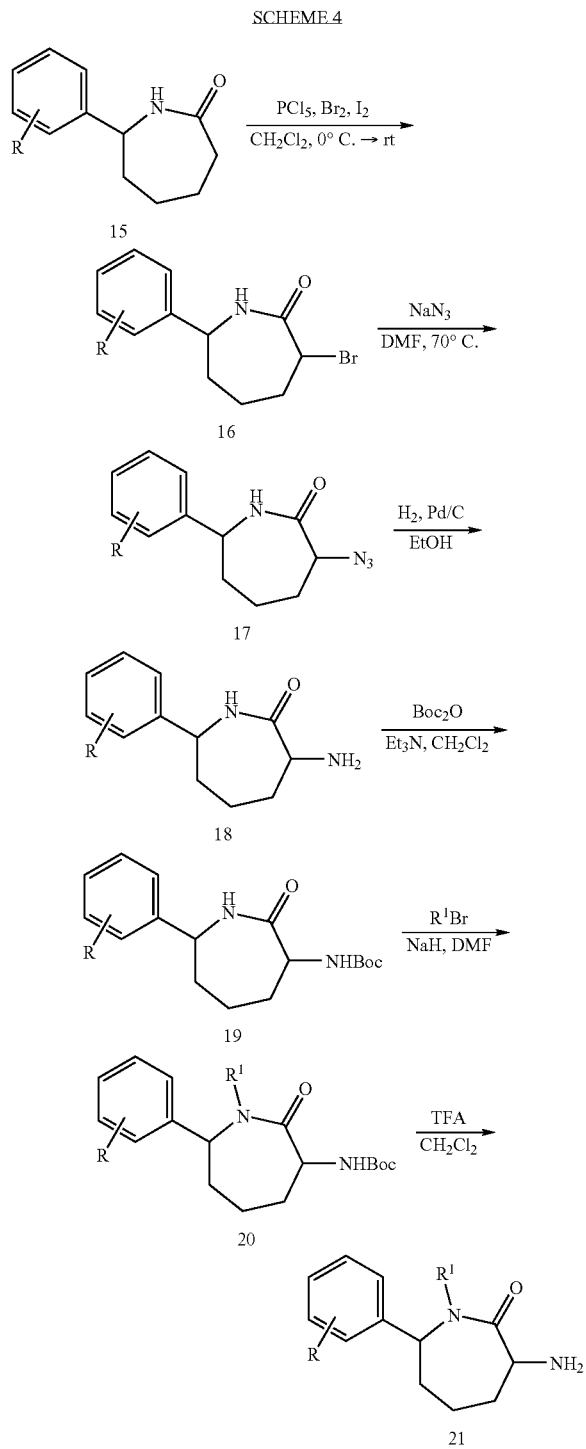

corresponding bromide 24, which is reacted with sodium azide and finally reduced under standard hydrogenation conditions, yielding amine compounds of the general formula 26.

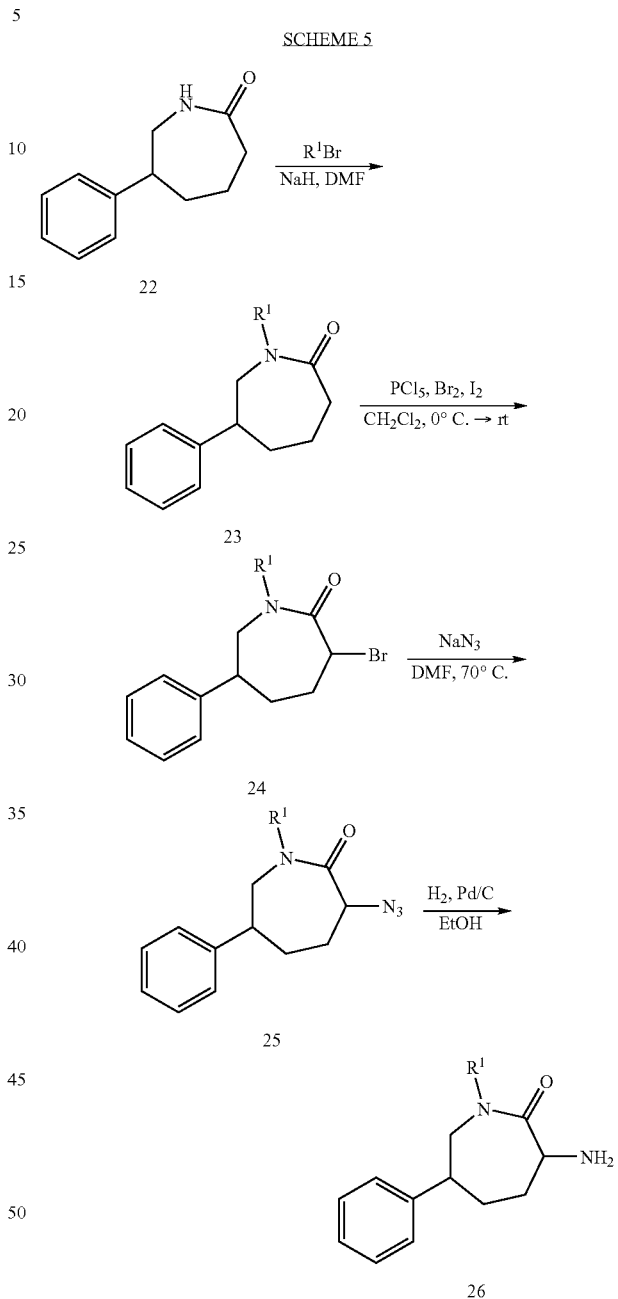

Lactam 22 can be prepared according to known procedures (J. Med. Chem., 1988, 31, 422-428) (Scheme 5). Using sodium hydride as the base, the amide can be alkylated with various electrophiles such as alkyl bromides. Bromination with phosphorus pentachloride and liquid bromine gives the Alternatively, caprolactams can be assembled following an olefin metathesis strategy as outlined in Scheme 6. 2,4-Dimethoxybenzylamine hydrochloride is alkylated with 2,3-dibromopropene under mild basic conditions to give amine 28. (2R)-2-{[(benzyloxy)carbonyl]amino}pent-4-enoic acid 29, prepared in one step from commercially available D-allyl glycine according to known procedures (J. Chem. Soc., 1962, 3963-3968), can be coupled to amine 28 under a variety of conditions to give amide 30. A variety of transition metal catalyzed cross couplings can be performed on the vinyl bromide, for example palladium-mediated arylations with phenylboronic acids and sodium carbonate, yielding styrene derivative 31. Ring-closing metathesis occurs in the presence of the Grubbs second generation ruthenium catalyst in dichloromethane with mild heating to afford lactam 32. Removal of the dimethoxybenzyl group and hydrogenation with in situ protection of the primary amine gives the corresponding saturated lactam 34. After selective alkylation of the amide nitrogen with various electrophiles such as alkyl bromides, deprotection under acidic conditions yields compounds of the general formula 36.

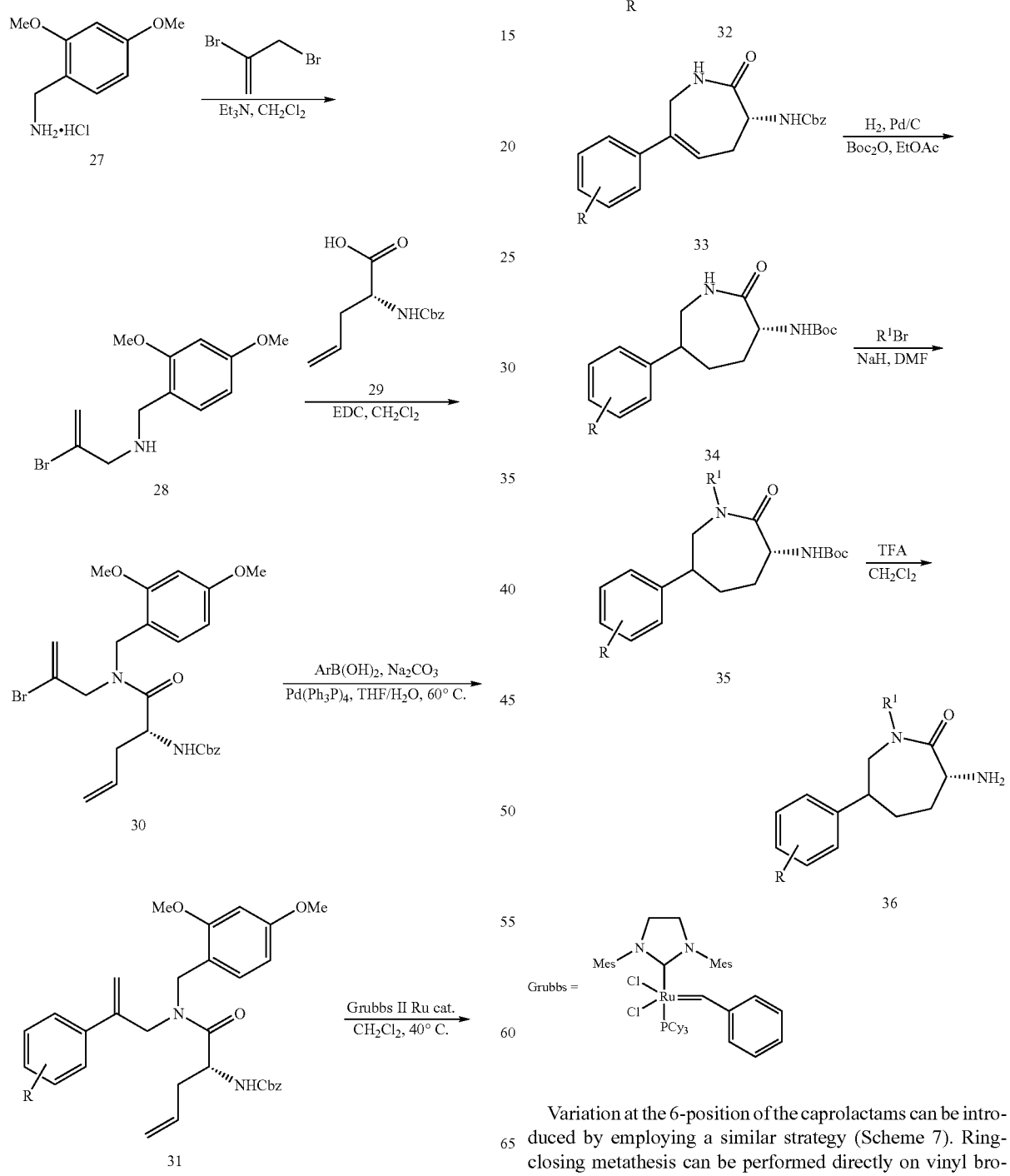

Variation at the 6-position of the caprolactams can be introduced by employing a similar strategy (Scheme 7). Ring-closing metathesis can be performed directly on vinyl bromide 30 using the Grubbs second generation ruthenium catalyst to give cyclic vinyl bromide 37. Removal of the dimethoxybenzyl group and palladium-mediated cross coupling, in this case with a boronic acid, furnishes compounds of the general formula 39. The transformation of 38 to 39 is not limited to boronic acid derivatives. After standard hydrogenation, the amide nitrogen can be selectively alkylated with various electrophiles, for example alkyl bromides, using sodium hydride as base. Deprotection yields lactams of the general formula 42.

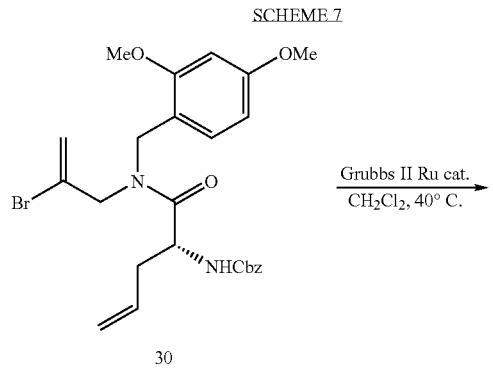

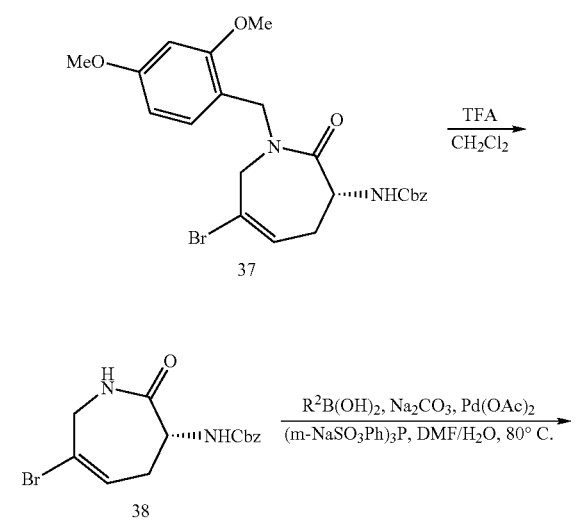

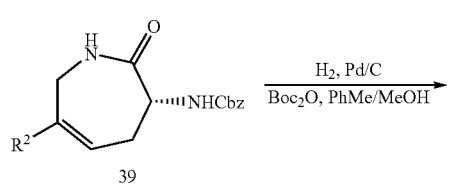

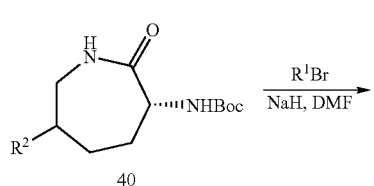

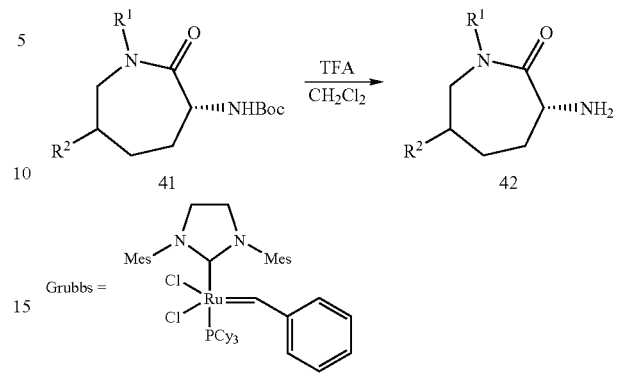

The 5-phenyl-3-amino caprolactam derivatives are prepared according to Scheme 8. 4-Phenylcyclohexanone (or substituted derivatives) can be reacted with alkyl and aryl azides in the presence of titanium(IV) chloride to give the corresponding lactams 44, following known general procedures (J. Am. Chem. Soc., 2000, 122, 7226-7232). Bromination with phosphorus pentachloride and elemental bromine gives the alkyl bromide 45, which is reacted with sodium azide and then reduced under standard hydrogenation conditions, yielding lactams of the general formula 47.

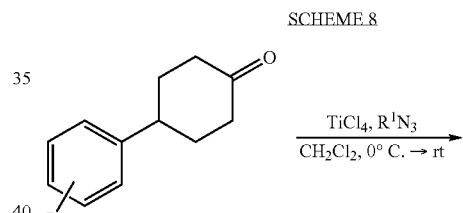

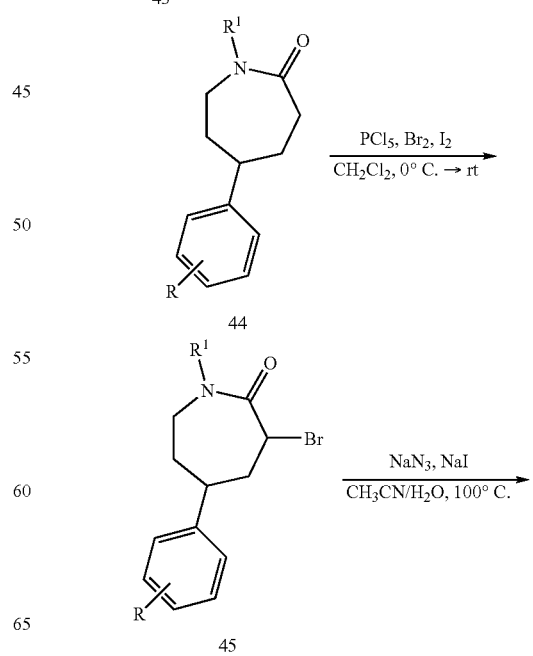

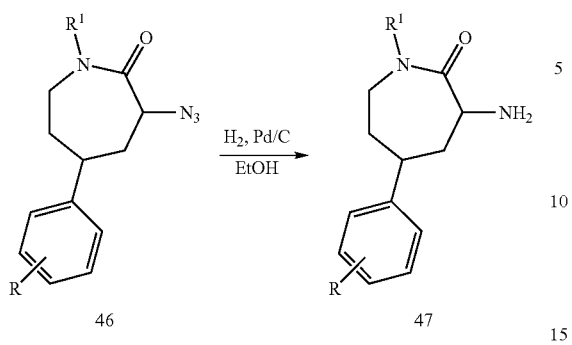

The oxazepanones can be prepared according to Scheme 9. (S)-(−)-Styrene oxide (or substituted derivatives) can be opened by reaction with various primary amines in isopropanol solvent to afford the corresponding amino alcohols 49. Selective N-protection followed by boron trifluoride etherate catalyzed aziridine opening of 51 (prepared according to known procedures: J. Chem. Soc., Perkins Trans. 1, 1994, 7, 807-816) provides ether 52. Hydrolysis of the methyl ester, selective amine deprotection, and amide bond formation with diphenylphosphoryl azide gives 54, which after standard hydrogenation conditions yields amine 55.

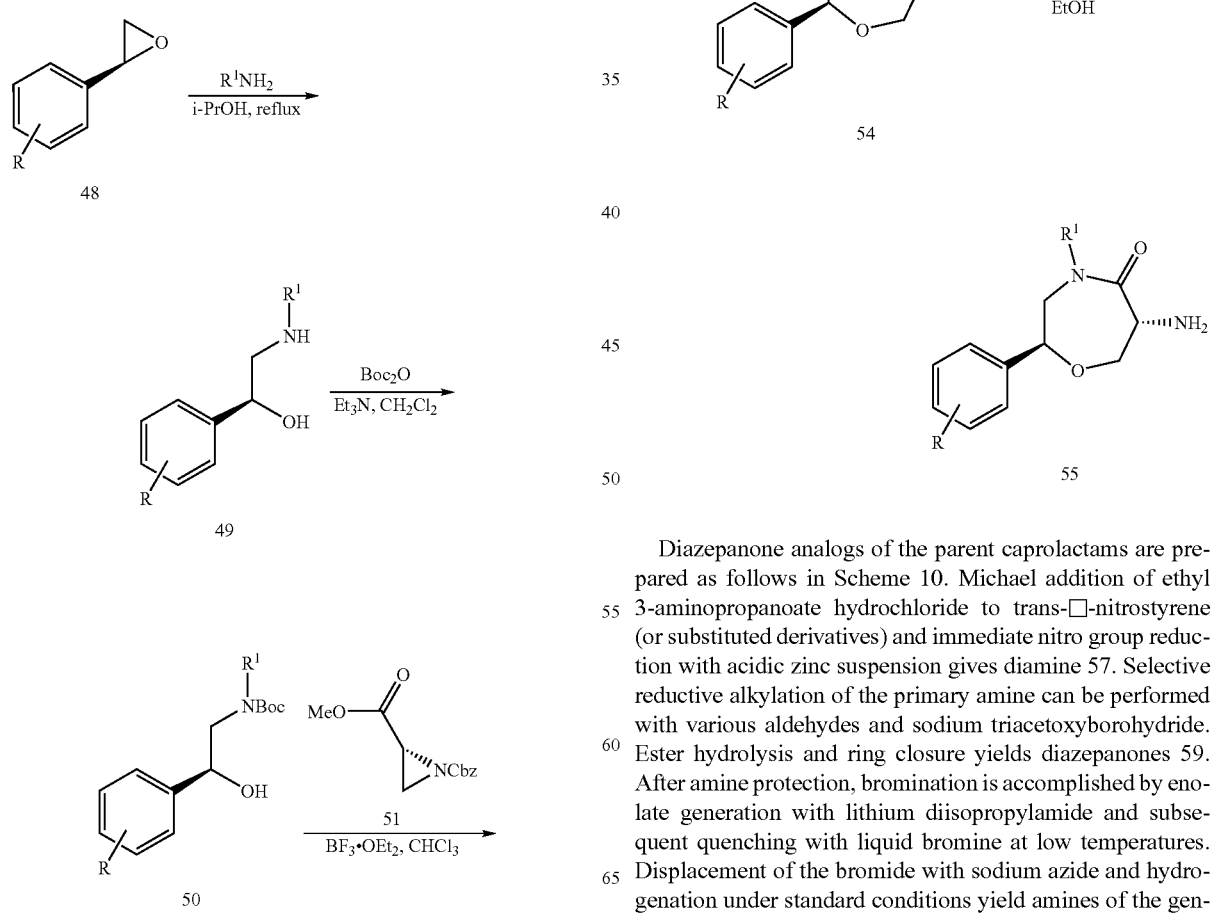

Diazepanone analogs of the parent caprolactams are prepared as follows in Scheme 10. Michael addition of ethyl 3-aminopropanoate hydrochloride to trans-□-nitrostyrene (or substituted derivatives) and immediate nitro group reduction with acidic zinc suspension gives diamine 57. Selective reductive alkylation of the primary amine can be performed with various aldehydes and sodium triacetoxyborohydride. Ester hydrolysis and ring closure yields diazepanones 59. After amine protection, bromination is accomplished by enolate generation with lithium diisopropylamide and subsequent quenching with liquid bromine at low temperatures. Displacement of the bromide with sodium azide and hydrogenation under standard conditions yield amines of the general formula 63.

SCHEME 10

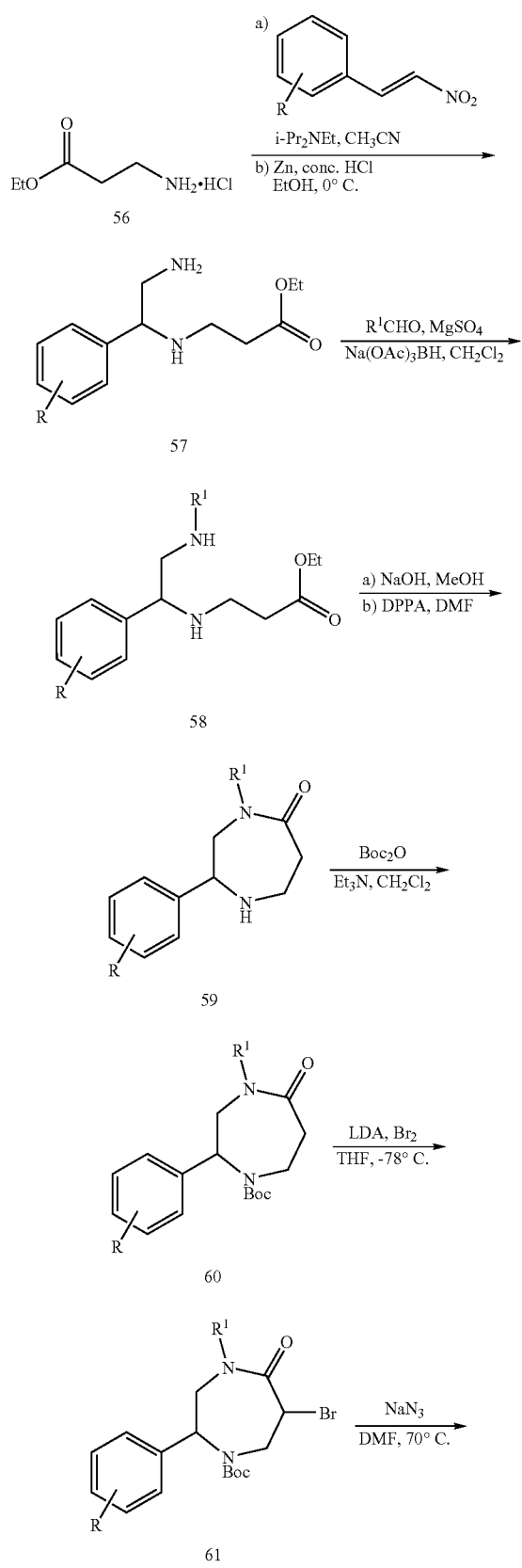

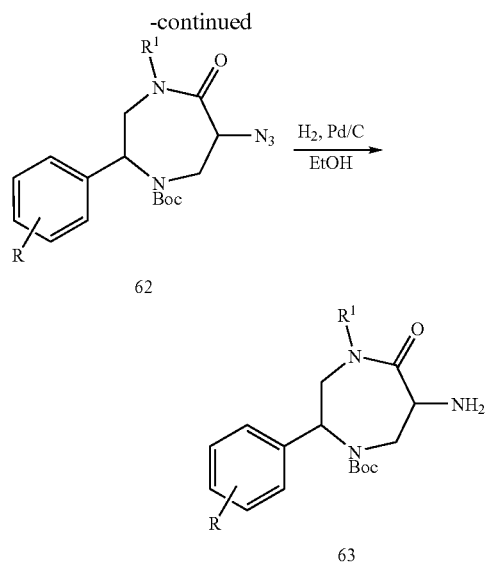

Thiazepanone analogs can be obtained following the strategy outlined in Scheme 11. Michael addition of N-Boc-D-cysteine methyl ester (prepared according to known procedures: Tetrahedron Asymmetry, 1997, 8, 1453-1466) to trans-□-nitrostyrene (or substituted derivatives) gives thioether 65. Reduction of the nitro group can be accomplished with hydrogen and palladium on carbon at high pressure. The corresponding amine 66 can be reductively alkylated with various aldehydes and sodium cyanoborohydride to the appropriate secondary amines 67. Ester hydrolysis, ring closure with diphenylphosphoryl azide, and deprotection under acidic conditions gives lactams of the general formula 69.

SCHEME 11

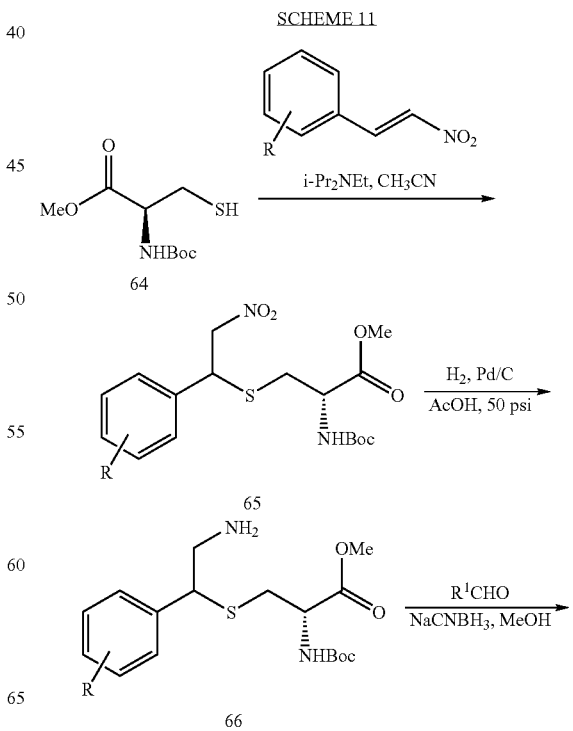

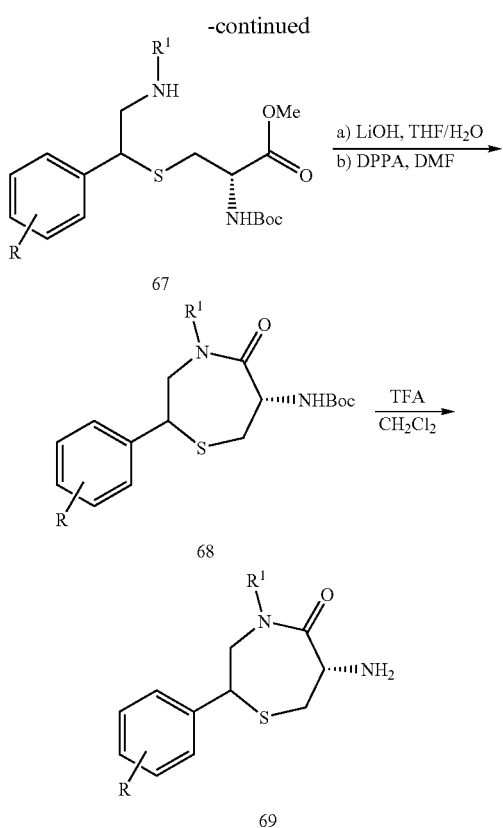

Alkyl substituted caprolactams 42 can be condensed with benzaldehyde to form the imine in the presence of magnesium sulfate (Scheme 12). Deprotonation with lithium bis(trimethylsilyl)amide, followed by quenching with electrophiles, for example alkyl bromides, and acid catalyzed imine hydrolysis gives substituted caprolactams of the general formula 71.

The 3-acetyl caprolactam derivatives can be prepared as outlined in Scheme 13. Lactam 22 (prepared according to known procedures: J. Med. Chem., 1988, 31, 422-428) can be alkylated selectively at the amide nitrogen with a variety of electrophiles, such as alkyl bromides, using sodium hydride as base. C-alkylation is achieved by generation of the enolate with lithium diisopropylamide followed by quenching with tert-butyl bromoacetate, giving ester 72. Deprotection of the carboxyl group is accomplished with trifluoroacetic acid. Coupling of the resultant carboxylic acid with amine 3 under standard conditions affords 3-acetyl lactams of the general formula 74.

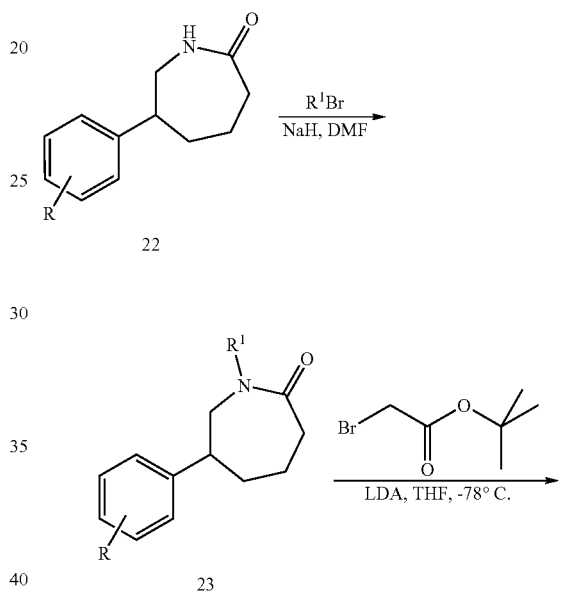

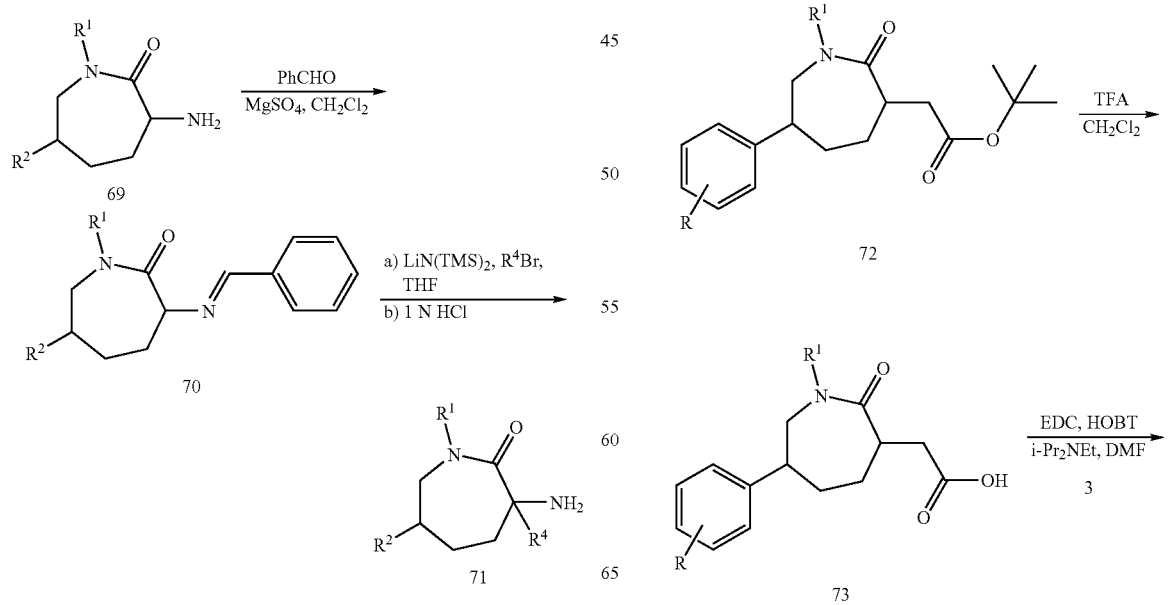

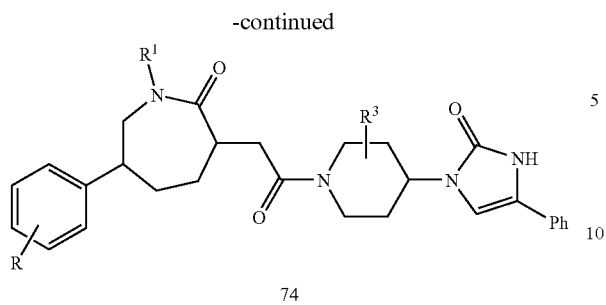
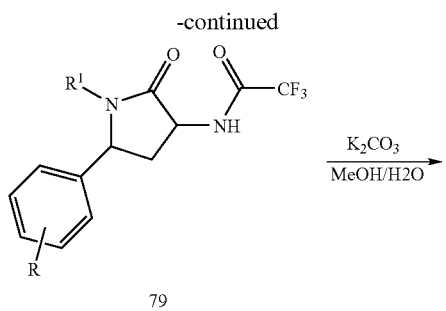

Aminopyrrolidinones such as 80 can be prepared as in Scheme 14. Friedel-crafts acylation of a benzene derivative with anhydride 75 produces an acid such as 76, which can be coupled with amines to gives amides such as 77. Cyclodehydration and double-bond reduction affords the pyrrolidinones 79. Final deprotection with base furnishes aminopyrrolidinones 8.

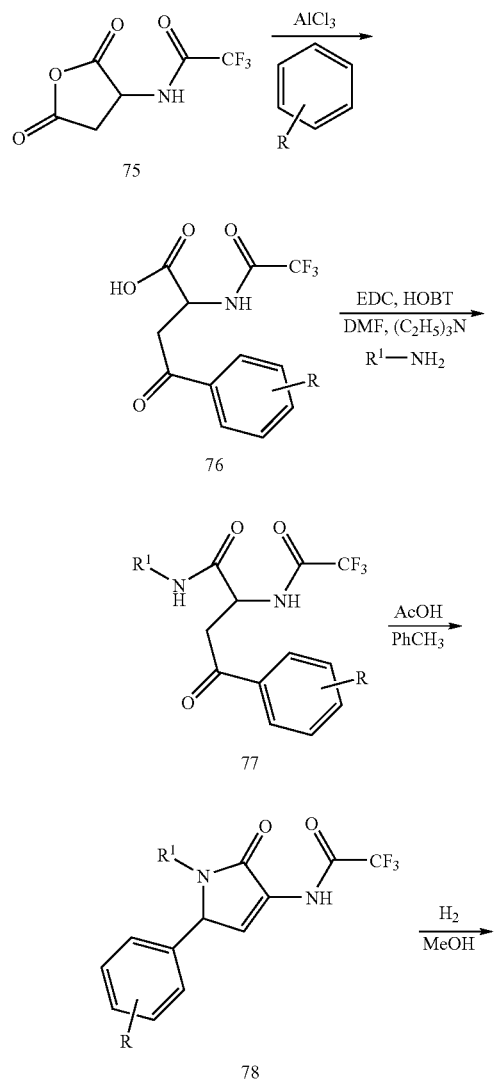

The piperidinones can be assembled following the strategy in Scheme 15. Hydrogenation of 3-nitropyridinone followed by protection of the amino group as its benzyl carbamate affords 83. Regioselective iodination followed by nitrogen alkylation with an electrophile such as an alkyl bromide gives 85. A variety of transition metal catalyzed cross coupling can be performed on the aryl iodide, for example palladium-mediated arylations with phenylboronic acids and sodium carbonate, yield biaryl derivatives 86. Deprotection of the benzyl carbamate and reduction of the pyridinone ring yields piperidinones of the general formula 87.

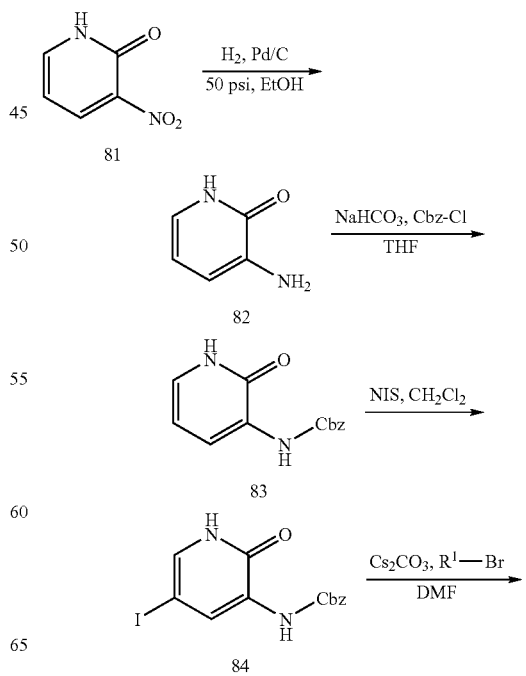

-continued

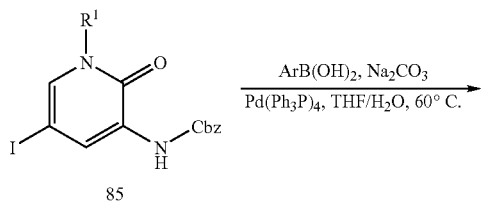

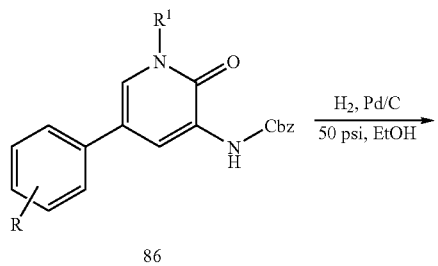

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

EXAMPLES

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

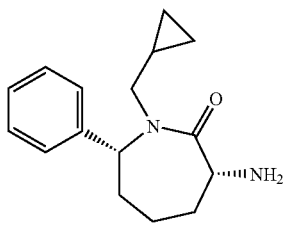

(3R,7R)-3-Amino-1-(cyclopropylmethyl)-7-phenylazepan-2-one

Step A: 3-Bromo-7-phenylazepan-2-one

Phosphorus pentachloride (4.95 g, 23.8 mmol) was added to a solution of 7-phenylazepan-2-one (4.50 g, 23.8 mmol) in dichloromethane (75 mL) at 0° C. After 1 h, iodine (0.060 g, 0.24 mmol) and a solution of bromine (1.22 mL, 23.8 mmol) in dichloromethane (10 mL) were added sequentially and the mixture was allowed to warm to ambient temperature. After 1.5 h, the reaction was quenched with aqueous sodium sulfite. The mixture was extracted with dichloromethane (3×), and the combined organic extracts were dried over magnesium sulfate, filtered, and concentrated. Purification by silica gel chromatography (10% ethyl acetate/hexanes→50% ethyl acetate/hexanes) gave the title compound (4.91 g). MS 268 (M+1).

Step B: (3R,7R)-3-Azido-7-phenylazepan-2-one and (3S,7S)-3-Azido-7-phenylazepan-2-one Sodium azide (8.73 g, 134 mmol) was added to a solution of 3-bromo-7-phenylazepan-2-one in N,N-dimethylformamide (40 mL) and the mixture heated to 60° C. After 2 h the reaction was allowed to cool to ambient temperature, concentrated, and diluted with water. The mixture was extracted with ethyl acetate, and the organic layer was washed with water (3×) and saturated brine, dried over magnesium sulfate, filtered, and concentrated. Purification by silica gel chromatography (30% ethyl acetate/hexanes→50% ethyl acetate/hexanes) gave the racemic cis and trans compounds. The cis enantiomers were separated on a Chiralpak AD column eluting with 100% methanol to give the title compounds, enantiomer A (1.09 g) and enantiomer B (1.06 g). MS 231 (M+1).

Step C: tert-Butyl (3R,7R)-2-oxo-7-phenylazepan-3-ylcarbamate

10% palladium on carbon (0.90 g) was added to a solution of (3R,7R)-3-azido-7-phenylazepan-2-one (0.89 g, 3.87 mmol) in ethanol (10 mL). The reaction vessel was evacuated and back-filled with nitrogen (3×), then back-filled with hydrogen (1 atm). After 18 h, the mixture was filtered and concentrated. Triethylamine (0.61 mL, 4.41 mmol) was added to a solution of the crude amine and di-tert-butyl dicarbonate (0.96 g, 4.41 mmol) in dichloromethane (20 mL). After 1 h, the mixture was concentrated. Purification by silica gel chromatography (100% dichloromethane→95% dichloromethane/methanol) gave the title compound (0.79 g).

Step D: tert-Butyl (3R,7R)-1-(cyclopropylmethyl)-2-oxo-7-phenylazepan-3-ylcarbamate Sodium hydride (60% dispersion in mineral oil; 14.4 mg, 0.36 mmol) was added to a solution of tert-butyl (3R,7R)-2-oxo-7-phenylazepan-3-ylcarbamate (100 mg, 0.33 mmol) and cyclopropylmethyl bromide (0.08 mL, 0.82 mmol) in N,N-dimethylformamide (1 mL) at 0 □C, and the mixture was allowed to warm to ambient temperature. After 6 h, the reaction was quenched with water and the mixture was extracted with ethyl acetate. The organic layer was washed with water (3×), saturated brine, dried over magnesium sulfate, filtered and concentrated. Purification by silica gel chromatography (10% ethyl acetate/hexanes→50% ethyl acetate/hexanes) gave the title compound (82 mg). MS 359 (M+1).

Step E: (3R,7R)-3-Amino-1-(cyclopropylmethyl)-7-phenylazepan-2-one

Trifluoroacetic acid (2.5 mL) was added to a solution tert-butyl (3R,7R)-1-(cyclopropylmethyl)-2-oxo-7-phenylazepan-3-ylcarbamate (82 mg, 0.23 mmol) in dichloromethane (5 mL). After 1 h, the mixture was concentrated and aqueous saturated sodium bicarbonate was added. The mixture was extracted with dichloromethane (2×), and the combined organic extracts were dried over magnesium sulfate, filtered, and concentrated to give the title compound (53 mg). $^1$H NMR (500 MHz, CDCl$_3$) ☐ 7.40-7.37 (m, 2H), 7.34-7.31 (m, 3H), 4.97 (dd, J=9.3, 3.7 Hz, 1H), 4.05 (dd, J=9.8, 4.2 Hz, 1H), 3.24 (dd, J=14.4, 7.1 Hz, 1H), 2.69 (dd, J=14.2, 7.1 Hz, 1H), 2.16-2.10 (m, 2H), 2.03-1.97 (m, 1H), 1.92-1.85 (m, 2H), 1.65-1.56 (m, 1H), 0.69-0.63 (m, 1H), 0.34-0.23 (m, 2H), 0.09-0.04 (m, 1H), −0.10-0.15 (m, 1H).

INTERMEDIATE 2

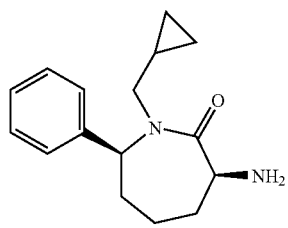

(3S,7S)-3-Amino-1-(cyclopropylmethyl)-7-phenylazepan-2-one

Step A: tert-Butyl (3S,7S)-2-oxo-7-phenylazepan-3-ylcarbamate

10% palladium on carbon (95 mg) was added to a solution (3S,7S)-3-azido-7-phenylazepan-2-one (954 mg, 4.14 mmol) in ethanol (10 mL). The reaction vessel was evacuated and back-filled with nitrogen (3×), then back-filled with hydrogen (1 atm). After 18 h, the mixture was filtered and concentrated. Triethylamine (0.64 mL, 4.6 mmol) was added to a solution of the crude amine and di-tert-butyl dicarbonate (1.0 g, 4.6 mmol) in dichloromethane (20 mL). After 1 h, the mixture was concentrated. Purification by silica gel chromatography (99% dichloromethane→95% dichloromethane/methanol) gave the title compound (983 mg).

Step B: tert-Butyl (3S,7S)-1-(cyclopropylmethyl)-2-oxo-7-phenylazepan-3-ylcarbamate Sodium hydride (60% dispersion in mineral oil; 20.6 mg, 0.52 mmol) was added to a solution of tert-butyl (3S,7S)-2-oxo-7-phenylazepan-3-ylcarbamate (143 mg, 0.47 mmol) and cyclopropylmethyl bromide (0.11 mL, 1.18 mmol) in N,N-dimethylformamide (1 mL) at 0 ☐C, and the mixture was allowed to warm to ambient temperature. After 14 h, the reaction was quenched with water and the mixture was extracted with ethyl acetate. The organic layer was washed with water (3×), saturated brine, dried over magnesium sulfate, filtered and concentrated. Purification by silica gel chromatography (10% ethyl acetate/hexanes→30% ethyl acetate/hexanes) gave the title compound (144 mg). MS 359 (M+1).

Step C: (3S,7S)-3-Amino-1-(cyclopropylmethyl)-7-phenylazepan-2-one

Trifluoroacetic acid (2.5 mL) was added to a solution tert-butyl (3S,7S)-1-(cyclopropylmethyl)-2-oxo-7-phenylazepan-3-ylcarbamate (144.1 mg, 0.40 mmol) in dichloromethane (5 mL). After 1 h, the mixture was concentrated and aqueous saturated sodium bicarbonate was added. The mixture was extracted with dichloromethane (2×), and the combined organic extracts were dried over magnesium sulfate, filtered, and concentrated to give the title compound (110 mg).

Essentially following the procedures outlined for the preparation of Intermediate 2, the Intermediate in Table 1 was prepared.

TABLE 1

| Intermediate | Structure | MS (M + 1) |
|---|---|---|
| 3 | 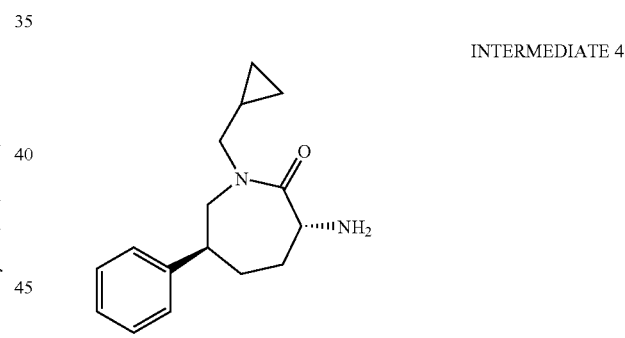 | 318.4 |

INTERMEDIATE 4

(3R,6S)-3-Amino-1-(cyclopropylmethyl)-6-phenylazepan-2-one

Step A: 1-(Cyclopropylmethyl)-6-phenylazepan-2-one

Sodium hydride (60% dispersion in mineral oil; 0.793 g, 19.8 mmol) was added to a solution of 6-phenylazepan-2-one (2.50 g, 13.2 mmol) and cyclopropylmethyl bromide (1.92 mL, 19.8 mmol) in N,N-dimethylformamide (30 mL) at 0° C. and then warmed to ambient temperature. After 18 h the mixture was quenched with water and extracted with ethyl acetate. The organic layer was washed with water (3×) and saturated brine, dried over magnesium sulfate, filtered, and concentrated. Purification by silica gel chromatography (1% methanol/dichloromethane→5% methanol/dichloromethane) gave the title compound (2.33 g). MS 244 (M+1).

Step B: 3-Amino-1-(cyclopropylmethyl)-6-phenylazepan-2-one

Phosphorus pentachloride (1.99 g, 9.57 mmol) was added to a solution of 1-(cyclopropylmethyl)-6-phenylazepan-2-one (2.33 g, 9.57 mmol) in dichloromethane (55 mL) at 0° C. After 1 h, iodine (0.024 g, 0.096 mmol) and a solution of bromine (0.49 mL, 9.57 mmol) in dichloromethane (5 mL) were added sequentially and the mixture was allowed to warm to ambient temperature. After 18 h, the reaction was quenched with aqueous sodium sulfite. The mixture was extracted with dichloromethane (3×), and the combined organic extracts were dried over magnesium sulfate, filtered, and concentrated. Sodium azide (5.60 g, 86.2 mmol) was added to a solution of the crude bromide in N,N-dimethylformamide (50 mL) and the mixture heated to 50° C. After 4 h, the reaction was allowed to cool to ambient temperature, concentrated, and diluted with water. The mixture was extracted with ethyl acetate, washed with water (3×) and saturated brine, dried over magnesium sulfate, filtered, and concentrated. 10% palladium on carbon (0.50 g) was added to a solution of the crude azide in ethanol (50 mL). The reaction vessel was evacuated and back-filled with nitrogen (3×), then back-filled with hydrogen (1 atm). After 18 h, the mixture was filtered and concentrated. Purification by silica gel chromatography [100% dichloromethane→95% dichloromethane/(10% ammonium hydroxide/methanol)] gave the racemic amine. MS 259 (M+1).

Step C: (3R,6S)-3-Amino-1-(cyclopropylmethyl)-6-phenylazepan-2-one

The cis and trans enantiomers were both separated using a Chiralcel OD column eluting with 5% 2-propanol/90% (hexanes with 0.1% diethyl amine)/5% methanol to give the title compound (247 mg). MS 259 (M+1). $^1$H NMR (500 MHz, CDCl$_3$) □ 7.34 (t, J=7.6 Hz, 2H), 7.26-7.23 (m, 1H), 7.17 (d, J=7.6 Hz, 2H), 3.86-3.81 (m, 2H), 3.62 (dd, J=13.9, 6.8 Hz, 1H), 3.32 (d, J=11.1 Hz, 1H), 3.08 (dd, J=13.9, 7.3 Hz, 1H), 2.79-2.74 (m, 1H), 2.14-2.12 (m, 1H), 2.02-1.97 (m, 2H), 1.77-1.67 (m, 1H), 1.03-0.99 (m, 1H), 0.55-0.49 (m, 2H), 0.28-0.25 (m, 2H).

INTERMEDIATE 5

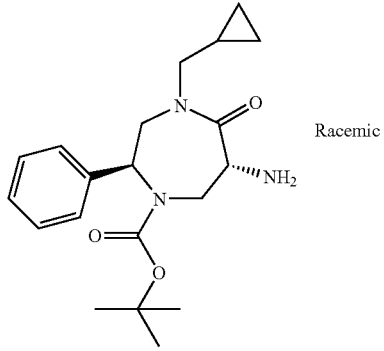

Racemic tert-Butyl (2S,6R and 2R,6S)-6-amino-4-(cyclopropylmethyl)-5-oxo-2-phenyl-1,4-diazepane-1-carboxylate

Step A: Ethyl 3-[(2-amino-1-phenylethyl)amino]propanoate

Trans-□-Nitrostyrene (4.04 g, 27.1 mmol) was added to a solution of ethyl 3-aminopropanoate hydrochloride (4.16 g, 27.1 mmol), and N,N-diisopropylethylamine (9.43 mL, 54.2 mmol) in acetonitrile (70 mL). After 15 min, anhydrous hydrochloric acid gas was bubbled into the solution until acidic. The mixture was concentrated, redissolved in ethanol (60 mL) and aqueous hydrochloric acid (12 M; 30 mL), and cooled to 0° C. Zinc dust (8.80 g, 134 mmol) was added in portions over 5 min. After 0.5 h, the mixture was concentrated to remove ethanol and saturated aqueous sodium carbonate was added. The mixture was extracted with dichloromethane (3×), and the combined organic extracts were dried over magnesium sulfate, filtered and concentrated to give the title compound (9.5 g). MS 237 (M+1).

Step B: Ethyl N-{2-[(cyclopropylmethyl)amino]-1-phenylethyl}-beta-alaninate A mixture of ethyl 3-[(2-amino-1-phenylethyl)amino]propanoate (6.38 g, 27.0 mmol), magnesium sulfate (10 g, 83.1 mmol), and cyclopropanecarboxaldehyde (2.02 mL, 27.2 mmol) in dichloroethane (200 mL) was adjusted to pH 6 with acetic acid. After 1 h, sodium triacetoxyborohydride (5.72 g, 27.0 mmol) was added. After an additional 30 min, saturated aqueous sodium bicarbonate was added and the mixture was extracted with dichloromethane (3×). The combined organic extracts were dried over magnesium sulfate, filtered, and concentrated. Purification by silica gel chromatography [100% dichloromethane→95% dichloromethane/5% (10% ammonium hydroxide/methanol)] gave the title compound (3.14 g). MS 291 (M+1).

Step C: 4-(Cyclopropylmethyl)-2-phenyl-1,4-diazepan-5-one

Sodium hydroxide (1M; 6.53 mL, 6.53 mmol) was added to a solution of ethyl N-{2-[(cyclopropylmethyl)amino]-1-phenylethyl}-beta-alaninate (1.81 g, 6.22 mmol) in methanol (10 mL). After 1 h, the mixture was concentrated and azeotroped with toluene (3×) to give the crude acid. Diphenylphosphoryl azide (2.68 ml, 12.43 mmol) was added to a solution of the crude acid (1.77 g, 6.22 mmol) and 4-methylmorpholine (1.37 mL, 12.4 mmol) in N,N-dimethylformamide (124 mL). After 18 h, the reaction was concentrated and diluted with water. The mixture was extracted with dichloromethane (3×), and the combined organic extracts were dried over magnesium sulfate, filtered, and concentrated. Purification by silica gel chromatography [100% dichloromethane→90% dichloromethane/10% (10% ammonium hydroxide/methanol)] gave the title compound (1.38 g). MS 245 (M+1). $^1$H NMR (500 MHz, CDCl$_3$) □ 7.47-7.30 (m, 5H), 3.89-3.88 (m, 2H), 3.65 (dd, J=13.9, 6.6 Hz, 1H), 3.31-3.26 (m, 1H), 3.24-3.21 (m, 1H), 3.02-2.93 (m, 3H), 2.70-2.65 (m, 1H), 1.02-0.97 (m, 1H), 0.58-0.49 (m, 2H), 0.28-0.21 (m, 2H).

Step D: tert-Butyl 4-(cyclopropylmethyl)-5-oxo-2-phenyl-1,4-diazepane-1-carboxylate Triethylamine (0.53 mL, 3.79 mmol) was added to a solution of 4-(cyclopropylmethyl)-2-phenyl-1,4-diazepan-5-one (0.925 g, 3.79 mmol) and di-tert-butyl dicarbonate (0.826 g, 3.79 mmol) in dichloromethane (20 mL). After 18 h, the mixture was diluted with water. The mixture was extracted with dichloromethane, washed with saturated brine, dried over magnesium sulfate, filtered, and concentrated. Purification by silica gel chromatography (100% dichloromethane→95% dichloromethane/methanol) gave the title compound (1.38 g). MS 345 (M+1).

Step E: tert-Butyl 6-bromo-4-(cyclopropylmethyl)-5-oxo-2-phenyl-1,4-diazepane-1-carboxylate Lithium diisopropylamide (1 M in THF; 2.13 mL, 2.13 mmol) was added to tert-butyl 4-(cyclopropylmethyl)-5-oxo-2-phenyl-1,4-diazepane-1-carboxylate (0.489 g, 1.42 mmol) in tetrahydrofuran (5 mL) at −78° C. After 30 min, the enolate solution was transferred dropwise via cannula to a solution of bromine (0.36 mL, 7.10 mmol) in tetrahydrofuran (3 mL) at −78° C. over a period of 5 min. After 15 min, the mixture was quenched with aqueous saturated sodium sulfite and allowed to warm to ambient temperature. The mixture was extracted with ethyl acetate, washed with saturated 50 aqueous sodium bicarbonate and saturated brine, dried over magnesium sulfate, filtered, and concentrated. MS 423 (M+1).

Step F: cis and trans tert-Butyl-6-azido-4-(cyclopropylmethyl)-5-oxo-2-phenyl-1,4-diazepane-1-carboxylate Sodium azide (0.841 g, 12.9 mmol) was added to a solution of tert-butyl 6-bromo-4-(cyclopropylmethyl)-5-oxo-2-phenyl-1,4-diazepane-1-carboxylate (0.609 g, 1.43 mmol) in N,N-dimethylforamide (10 mL) and heated to 70° C. After 1 h, the mixture was allowed to cool to ambient temperature and water was added. The mixture was extracted with ethyl acetate, washed with water (3×), saturated brine, dried over magnesium sulfate, filtered, and concentrated. Purification by silica gel chromatography (20% ethyl acetate/hexanes→50% ethyl acetate/hexanes) gave 170 mg of the trans isomer and 24 mg of the cis isomer. MS 386 (M+1).

Step G: tert-Butyl (2R,6S and 2S,6R)-6-amino-4-(cyclopropylmethyl)-5-oxo-2-phenyl-1,4-diazepane-1-carboxylate 10% palladium on carbon (45.5 mg) was added to a solution of trans tert-butyl-6-azido-4-(cyclopropylmethyl)-5-oxo-2-phenyl-1,4-diazepane-1-carboxylate (165 mg, 0.428 mmol) in ethanol (15 mL). The reaction vessel was evacuated and back-filled with nitrogen (3×), then back-filled with hydrogen (1 atm). After 3 h, the mixture was filtered and concentrated to give the title compound (154 mg). MS 360 (M+1).

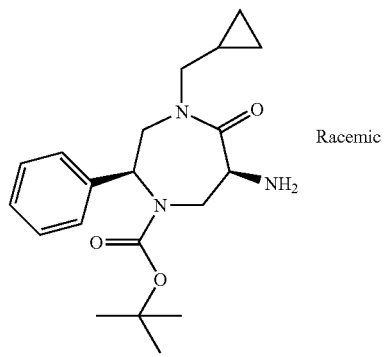

INTERMEDIATE 5a

Racemic tert-Butyl (2S,6S and 2R,6R)-6-amino-4-(cyclopropylmethyl)-5-oxo-2-phenyl-1,4-diazepane-1-carboxylate 10% palladium on carbon (24 mg) was added to a solution of is cis-butyl-6-azido-4-(cyclopropylmethyl)-5-oxo-2-phenyl-1,4-diazepane-1-carboxylate (24 mg, 0.062 mmol) in ethanol (5 mL). The reaction vessel was evacuated and back-filled with nitrogen (3×), then back-filled with hydrogen (1 atm). After 4 h, the mixture was filtered and concentrated to give the title compound (22 mg). MS 360 (M+1).

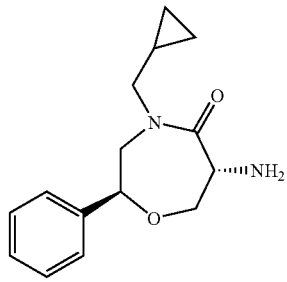

INTERMEDIATE 6

(2S,6R)-6-Amino-4-(cyclopropylmethyl)-2-phenyl-1,4-oxazepan-5-one

Step A: tert-Butyl cyclopropylmethyl[(2S)-2-hydroxy-2-phenylethyl]carbamate (S)-Styrene oxide (4.83 g, 40.3 mmol) and cyclopropanemethylamine (4.00 g, 56.4 mmol) were dissolved in isopropyl alcohol (100 mL) and heated to reflux. After 8 h, the reaction was allowed to cool to ambient temperature and concentrated. Triethylamine (5.61 mL, 40.3 mmol) was added to a solution of the crude amine and di-tert-butyl dicarbonate (8.78 g, 40.3 mmol) in dichloromethane (100 mL). After 18 h, water was added, and the mixture was extracted with ethyl acetate. The organic layer was washed with brine, dried over magnesium sulfate, filtered and concentrated. Purification by silica gel chromatography (5% ethyl acetate/hexanes→20% ethyl acetate/hexanes) gave the title compound (5.48 g).

Step B: Methyl N-[(benzyloxy)carbonyl]-O-{(1S)-2-[(tert-butoxycarbonyl)(cyclopropylmethlyl)amino]-1-phenylethyl}-D-serinate Boron trifluoride diethyl etherate (0.10 mL, 0.84 mmol) was added to a solution of tert-butyl cyclopropylmethyl[(2S)-2-hydroxy-2-phenylethyl]carbamate (2.45 g, 8.39 mmol) and 1-benzyl 2-methyl (2R)-aziridine-1,2-dicarboxylate (1.97 g, 8.39 mmol) in chloroform (20 mL). After 3 h, the reaction was concentrated. Purification by silica gel chromatography (100% hexanes→30% ethyl acetate/hexanes) gave the title compound (1.21 g).

Step C: N-[(Benzyloxy)carbonyl]-O-{(1S)-2-[(tert-butoxycarbonyl)(cyclopropylmethyl)amino]-1-phenylethyl}-D-serine Aqueous sodium hydroxide (1 M; 3.81 mL, 3.81 mmol) was added to a solution of methyl N-[(benzyloxy)carbonyl]-O-{(1S)-2-[(tert-butoxycarbonyl)(cyclopropylmethyl)amino]-1-phenylethyl}-D-serinate (1.30 g, 2.46 mmol) in tetrahydrofuran (20 mL). After 18 h, aqueous hydrochloric acid (1 M; 3.81 mL, 3.81 mmol) was added. The mixture was extracted with dichloromethane (3×), and the combined organic extracts were dried over magnesium sulfate, filtered, and concentrated to give the title compound. (1.27 g) MS 535 (M+Na).

Step D: Benzyl (2S,6R)-4-(cyclopropylmethyl)-5-oxo-2-phenyl-1,4-oxazepan-6-ylcarbamate Trifluoroacetic acid (5.0 mL) was added to a solution N-[(benzyloxy)carbonyl]-O-{(is)-2-[(tert-butoxycarbonyl)(cyclopropylmethyl)amino]-1-phenylethyl}-D-serine (1.27 g, 2.47 mmol) in dichloromethane (15 mL). After 2 h, the mixture was concentrated and azeotroped with toluene (3×) to give the crude amine. Diphenylphosphoryl azide (1.07 ml, 4.95 mmol) was added to a solution of the crude amine and 4-methylmorpholine (0.82 mL, 7.41 mmol) in N,N-dimethylformamide (100 mL). After 18 h, the mixture was concentrated and water was added. The mixture was extracted with ethyl acetate, and the organic layer was washed with water (2×) and saturated brine, dried over magnesium sulfate, filtered, and concentrated. Purification by silica gel chromatography (5% ethyl acetate/hexanes→50% ethyl acetate/hexanes) gave the title compound (0.426 g). MS 395 (M+1).

Step E: (2S,6R)-6-Amino-4-(cyclopropylmethyl)-2-phenyl-1,4-oxazepan-5-one

10% palladium on carbon (20 mg) was added to a solution (2S,6R)-6-amino-4-(cyclopropylmethyl)-2-phenyl-1,4-oxazepan-5-one (179 mg, 0.454 mmol) in ethanol (15 mL). The reaction vessel was evacuated and back-filled with nitrogen (3×), then back-filled with hydrogen (1 atm). After 18 h, the mixture was filtered and concentrated to give the title compound (113 mg). MS 261 (M+1). ¹H NMR (500 MHz, CDCl₃) ☐ 7.40-7.31 (m, 5H), 4.53 (d, J=8.5 Hz, 1H), 4.10-4.03 (m, 2H), 3.90 (dd, J=15.9, 7.1 Hz, 1H), 3.80-3.65 (m, 2H), 3.36 (d, J=15.9 Hz, 1H), 3.03 (dd, J=13.9, 6.6 Hz, 1H), 1.06-1.01 (m, 1H), 0.64-0.53 (m, 2H), 0.33-0.25 (m, 2H).

Essentially following the procedures outlined for the preparation of Intermediate 6, the Intermediates in Table 2 were prepared.

TABLE 2

| Intermediate | Structure | MS (M + 1) |
| --- | --- | --- |
| 7 | racemic | 261.0 |
| 8 | racemic | 261.0 |

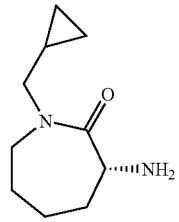

INTERMEDIATE 9

(3R)-3-Amino-1-(cyclopropylmethyl)azepan-2-one

Step A: tert-Butyl (3R)-1-(cyclopropylmethyl)-2-oxoazepan-3-ylcarbamate

Sodium hydride (60% dispersion in mineral oil; 30 mg, 1.24 mmol) was added to a solution tert-butyl (3R)-2-oxoazepan-3-ylcarbamate (258 mg, 1.13 mmol) and cyclopropylmethyl bromide (0.27 mL, 2.83 mmol) in N,N-dimethylformamide (3 mL) at 0° C., and the mixture was allowed to warm to ambient temperature. After 6 h, the reaction was quenched with water and the mixture was extracted with ethyl acetate. The organic layer was washed with water (3×), saturated brine, dried over magnesium sulfate, filtered and concentrated. Purification by silica gel chromatography (100% dichloromethane→5% methanol/dichloromethane) gave the title compound (257 mg). MS 283 (M+1).

Step B: (3R)-3-Amino-1-(cyclopropylmethyl)azepan-2-one

Trifluoroacetic acid (5 mL) was added to a solution of tert-butyl (3R)-1-(cyclopropylmethyl)-2-oxoazepan-3-ylcarbamate (257 mg, 0.91 mmol) in dichloromethane (10 mL). After 1 h, the mixture was concentrated and azeotroped with dichloromethane (3×) to give the crude amine.

Essentially following the procedures outlined for the preparation of Intermediate 9, the Intermediates in Table 3 were prepared.

TABLE 3

| Intermediate | Structure | MS (M + 1) |
|---|---|---|
| 10 | 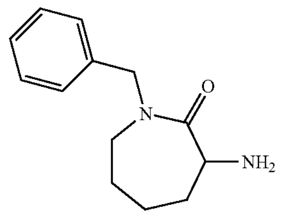 | 219.0 |
| 11 | 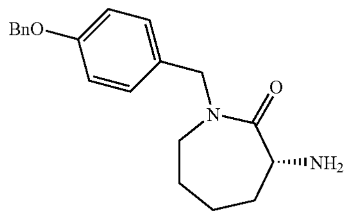 | 325.1 |
| 12 | 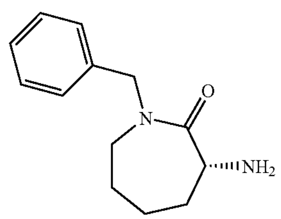 | 219.1 |

INTERMEDIATE 13

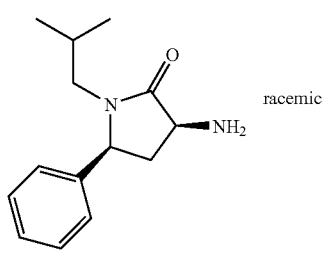

racemic cis-3-Amino-1-isobutyl-5-phenylpyrrolidin-2-one

Step A:
4-Oxo-4-phenyl-2-[(trifluoroacetyl)amino]butanoic acid

A solution of 3-[(trifluoroacetyl)amino]succinic anhydride (4.00 g, 19.0 mmol) and aluminum chloride (5.56 g, 41.7 mmol) in benzene (80 mL) was refluxed for 5 h, then cooled in an ice bath and quenched by the slow addition of water. The reaction mixture was worked up with ethyl acetate and 10% hydrochloric acid. The residue was purified by chromatography (silica gel, 100% methylene chloride to 90/10/1/1 methylene chloride/methanol/acetic acid/water gradient elution). Recrystallization of the resulting oil from methylene chloride/hexanes produced the title compound as a white solid (3.00 g). $^1$H NMR (500 MHz, ($d_6$-acetone) ☐ 11.56 (bs, 1H), 8.63 (bs, 1H), 8.06 (dd, J=8.3, 1.2 Hz, 2H), 7.70-7.67 (m, 1H), 7.57 (t, J=7.7 Hz, 2H), 5.14-5.10 (m, 1H), 3.84 (dd, J=18.3, 6.8 Hz, 1H), 3.77 (dd, J=18.1, 4.6 Hz, 1H).

Step B: N-Isobutyl-4-oxo-4-phenyl-2-[(trifluoroacetyl)amino]butanamide

A solution of 4-oxo-4-phenyl-2-[(trifluoroacetyl)amino] butanoic acid (3.9 g, 13.5 mmol), isobutylamine (2.68 mL, 27.0 mmol), N-[3-(dimethylamino)propyl]-N'-ethylcarbodiimide hydrochloride (5.17 g, 27.0 mmol), 1H-1,2,3-benzotriazol-1-ol hydrate (3.64 g, 27.0 mmol), and N,N-diisopropylethylamine (11.7 mL, 67.4 mmol) was stirred overnight at room temperature in dimethylformamide (20 mL). The reaction was worked up with methylene chloride and saturated sodium bicarbonate. The organic extracts were washed with brine, dried over sodium sulfate, filtered and concentrated. Chromatography (silica gel, 0 to 20% ethyl acetate in hexane gradient elution), gave the title compound as a yellow solid (1.41 g). MS 345 (M+1). $^1$H NMR (500 MHz, CDCl$_3$) ☐ 7.95 (d, J=7.3 Hz, 2H), 7.92 (bs, 1H), 7.63 (t, J=7.4 Hz, 1H), 7.50 (t, J=7.7 Hz, 2H), 6.86 (bs, 1H), 5.02-4.99 (m, 1H), 3.78 (dd, J=18.3, 2.4 Hz, 1H), 3.33 (dd, J=18.3, 9.0 Hz, 1H), 3.10 (t, J=6.4 Hz, 2H), 1.81-1.73 (m, 1H), 0.88 (d, 6H).

Step C: 2,2,2-Trifluoro-N-(1-isobutyl-2-oxo-5-phenyl-2,5-dihydro-1H-pyrrol-3-yl)acetamide A solution of N-isobutyl-4-oxo-4-phenyl-2-[(trifluoroacetyl)amino]butanamide (0.500 g, 1.45 mmol) and acetic acid (0.831 mL, 14.5 mmol) in toluene (15 mL) was heated to reflux. After 48 hours the reaction was cooled and concentrated. The crude product was purified by chromatography (silica gel, 0 to 50% ethyl acetate in hexane gradient elution) to give the title compound as a solid (0.412 g). MS 327 (M+1) $^1$H NMR (500 MHz, CDCl$_3$) ☐ 7.40-7.36 (m, 3H), 7.20 (d, J=2.0 Hz, 1H), 7.12-7.11 (m, 2H), 5.12 (d, J=2.0 Hz, 1H), 3.53 (dd, J=13.9, 9.4 Hz, 1H), 2.61 (dd, J=13.9, 5.9 Hz, 1H), 1.89-1.80 (m, 1H), 0.87 (d, J=6.6 Hz, 3H), 0.84 (d, J=6.6 Hz, 3H).

Step D: cis and trans-2,2,2-Trifluoro-N-(1-isobutyl-2-oxo-5-phenylpyrrolidin-3-yl)acetamide A solution of 2,2,2-trifluoro-N-(1-isobutyl-2-oxo-5-phenyl-2,5-dihydro-1H-pyrrol-3-yl)acetamide (300 mg, 0.919 mmol) and 10% palladium on carbon (50.0 mg) in methanol (6 mL) was stirred under a hydrogen balloon. After 2 hours the reaction was filtered through a Celite plug and concentrated. The crude product was purified by chromatography (silica gel, 0 to 50% ethyl acetate in hexane gradient elution) to give the title compound as a 1.4/1 mixture of cis/trans isomers (300 mg). Careful chromatography (silica gel, 0 to 20% ethyl acetate in hexane gradient elution, then 20 to 50% ethyl acetate in hexane gradient elution) allowed for the isolation of a portion of each the cis isomer ($2^{nd}$ eluting, 150 mg) and the trans isomer ($1^{st}$ eluting, 85 mg), along with several mixed fractions. Each isomer was carried forward individually. cis $^1$H NMR (500 MHz, CDCl$_3$) ☐ 7.42-7.35 (m, 3H), 7.26-7.24 (m, 3H), 4.60 (dd, J=9.3, 6.2 Hz, 1H), 4.53-4.48 (m, 1H), 3.48 (dd, J=13.7, 9.8 Hz, 1H), 3.21-3.16 (m, 1H), 2.46 (dd, J=13.7, 5.6 Hz, 1H), 1.88-1.72 (m, 2H), 0.81 (d, J=6.6 Hz, 3H), 0.78 (d, J=6.8 Hz, 3H); trans $^1$H NMR (500 MHz, CDCl$_3$) ☐ 7.55 (bs, 1H), 7.42-7.38 (m, 2H), 7.36-7.33 (m, 1H), 7.13 (d, J=7.8 Hz, 1H), 4.77 (d, J=8.8 Hz, 1H), 4.57-4.52

(m, 1H), 3.54 (dd, J=13.7, 9.3 Hz, 1H), 2.68-2.65 (m, 1H), 2.58 (dd, J=13.7, 5.9 Hz, 1H), 2.48-2.41 (m, 1H), 1.96-1.88 (m, 1H), 0.90 (d, J=2.2 Hz, 3H), 0.89 (d, J=2.4 Hz, 3H).

Step E:
cis-3-Amino-1-isobutyl-5-phenylpyrrolidin-2-one

To a solution of cis-2,2,2-trifluoro-N-(1-isobutyl-2-oxo-5-phenylpyrrolidin-3-yl)acetamide (50.0 mg, 0.152 mmol) in methanol (3 mL) and water (1 mL) was added potassium carbonate (63.1 mg, 0.447 mmol). After 27 hours, the reaction solution was concentrated, and worked up with methylene chloride and water. The organic extracts were dried over sodium sulfate, filtered and concentrated to produce the title compound (32.7 mg). MS 233 (M+1).

INTERMEDIATE 13a

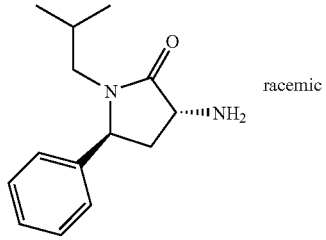

racemic trans-3-Amino-1-isobutyl-5-phenylpyrrolidin-2-one

To a solution of trans-2,2,2-trifluoro-N-(1-isobutyl-2-oxo-5-phenylpyrrolidin-3-yl)acetamide (63.2 mg, 0.192 mmol) in methanol (3 mL) and water (1 mL) was added potassium carbonate (79.8 mg, 0.578 mmol). After 27 hours, the reaction solution was concentrated and worked up with methylene chloride and water. The organic extracts were dried over sodium sulfate, filtered and concentrated to produce the title compound (44.7 mg). MS 233 (M+1).

INTERMEDIATE 14

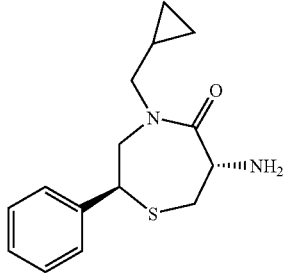

(2S,6S)-6-Amino-4-(cyclopropylmethyl)-2-phenyl-1,4-thiazepan-5-one

Step A: Methyl N-(tert-butoxycarbonyl)-S-(2-nitro-1-phenylethyl)-D-cysteinate

Diisopropylethylamine (3.38 mL, 19.4 mmol) was added to a solution of methyl N-(tert-butoxycarbonyl)-D-cysteinate (3.04 g, 12.9 mmol) and □-trans-nitrostyrene (1.93 g, 12.92 mmol) in acetonitrile (80 mL). After 15 min, the reaction was concentrated. Purification by silica gel chromatography (100% hexanes→30% ethyl acetate/hexanes) gave the title compound (4.52 g).

Step B: Methyl S-(2-amino-1-phenylethyl)-N-(tert-butoxycarbonyl)-D-cysteinate

10% palladium on carbon (3.04 g) was added to a solution of methyl N-(tert-butoxycarbonyl)-S-(2-nitro-1-phenylethyl)-D-cysteinate (1.00 g, 2.60 mmol) in acetic acid (50 mL). The reaction vessel was evacuated and back-filled with nitrogen (3×), then back-filled with hydrogen (50 psi). After 18 h the mixture was filtered, concentrated, and saturated aqueous sodium carbonate was added. The mixture was extracted with dichloromethane (3×), and the combined organic extracts were dried over magnesium sulfate, filtered, and concentrated to give the title compound (0.73 g). MS 355 (M+1).

Step C: Methyl N-(tert-butoxycarbonyl)-S-{2-[(cyclopropylmethyl)amino]-1-phenylethyl}-D-cysteinate Cyclopropanecarboxaldheyde (104 mg, 1.48 mmol) was added to a solution of methyl S-(2-amino-1-phenylethyl)-N-(tert-butoxycarbonyl)-D-cysteinate (583 mg, 1.65 mmol) in methanol (25 mL) adjusted to pH 6 with acetic acid. After 15 min, sodium cyanoborohydride (155 mg, 2.47 mmol) was added. After an additional 1 h, saturated aqueous sodium bicarbonate was added and the mixture was extracted with dichlormethane (2×). The combined organic extracts were dried over magnesium sulfate, filtered, and concentrated. Purification by silica gel [100% dichloromethane->97% dichloromethane/3% (10% ammonium hydroxide in methanol)] gave the title compound (305 mg). MS 409 (M+1).

Step D: tert-Butyl (2S,6S)-4-(cyclopropylmethyl)-5-oxo-2-phenyl-1,4-thiazepan-6-ylcarbamate Lithium hydroxide (63 mg, 1.49 mmol) was added to a solution of methyl N-(tert-butoxycarbonyl)-S-{2-[(cyclopropylmethyl)amino]-1-phenylethyl}-D-cysteinate (507 mg, 1.24 mmol) in tetrahydrofuran (10 mL) and water (2 mL). After 1 h, then mixture was concentrated and azeotroped with toluene (3×) to give the crude acid. Diphenylphosphoryl azide (0.53 ml, 2.48 mmol) was added to a solution of the crude acid and 4-methylmorpholine (0.20 mL, 1.86 mmol) in N,N-dimethylformamide (25 mL). After 4 h, the mixture was concentrated and water was added. The mixture was extracted with ethyl acetate, and the organic layer was washed with water (2×) and saturated brine, dried over magnesium sulfate, filtered, and concentrated. Purification by silica gel chromatography (5% ethyl acetate/hexanes→20% ethyl acetate/hexanes) gave the title compound (149 mg). MS 377 (M+1).

Step E: (2S,6S)-6-Amino-4-(cyclopropylmethyl)-2-phenyl-1,4-thiazepan-5-one

Trifluoroacetic acid (2.0 mL) was added to a solution of tert-butyl (2S,6S)-4-(cyclopropylmethyl)-5-oxo-2-phenyl-1,4-thiazepan-6-ylcarbamate (90 mg, 0.239 mmol) in dichloromethane (5 mL). After 1 h, the mixture was concentrated and aqueous saturated sodium bicarbonate was added. The mixture was extracted with dichloromethane (2×), and the combined organic extracts were dried over magnesium sulfate, filtered, and concentrated to give the crude product (57 mg). $^1$H NMR (500 MHz, CDCl$_3$) □ 7.38-7.30 (m, 5H), 4.36-4.28 (m, 2H), 4.06 (d, J=9.3 Hz, 1H), 3.74 (dd, J=14.4, 1.5 Hz, 1H), 3.67 (dd, J=13.9, 7.3 Hz, 1H), 3.08 (dd, J=13.9, 6.6 Hz, 1H), 3.00 (dd, J=14.4, 9.8 Hz, 1H), 2.66 (dd, J=14.4, 1.9 Hz, 1H), 1.02-0.99 (m, 1H), 0.57-0.53 (m, 2H), 0.27-0.23 (m, 2H).

INTERMEDIATE 15

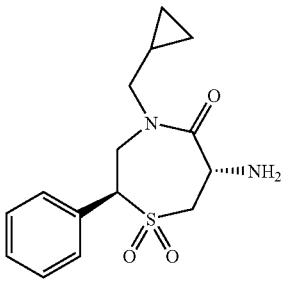

(2S,6S)-6-Amino-4-(cyclopropylmethyl)-2-phenyl-1,4-thiazepan-5-one 1,1-dioxide

Step A: tert-Butyl (2S,6S)-4-(cyclopropylmethyl)-1,1-dioxido-5-oxo-2-phenyl-1,4-thiazepan-6-ylcarbamate Oxone (488 mg, 0.80 mmol) was added to a solution of tert-butyl (2S,6S)-4-(cyclopropylmethyl)-5-oxo-2-phenyl-1,4-thiazepan-6-ylcarbamate (60 mg, 0.16 mmol) in methanol (7.5 mL) and water (7.5 mL). After 18 h, water was added. The mixture was extracted with ethyl acetate, and the organic layer was washed with saturated brine, dried over magnesium sulfate, filtered and concentrated to give the title compound (63 mg).

Step B: (2S,6S)-6-Amino-4-(cyclopropylmethyl)-2-phenyl-1,4-thiazepan-5-one 1,1-dioxide Trifluoroacetic acid (2.0 mL) was added to a solution of tert-butyl (2S,6S)-4-(cyclopropylmethyl)-1,1-dioxido-5-oxo-2-phenyl-1,4-thiazepan-6-ylcarbamate (63 mg, 0.167 mmol) in dichloromethane (5 mL). After 1 h, the mixture was concentrated and aqueous saturated sodium bicarbonate was added. The mixture was extracted with dichloromethane (2×), and the combined organic extracts were dried over magnesium sulfate, filtered, and concentrated to give the crude product (50 mg).

INTERMEDIATE 16

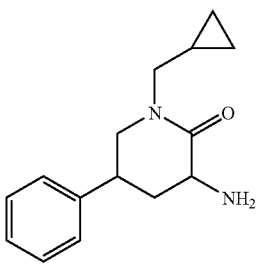

3-Amino-1-(cyclopropylmethyl)-5-phenylpiperidin-2-one

Step A: 3-Aminopyridin-2(1H)-one

3-Nitropyridin-2(1H)-one (1.195 g, 8.53 mmol) and 10% palladium on carbon (0.156 g) were stirred in ethanol (30 ml) overnight under hydrogen atmosphere (50 psi). Catalyst was filtered from the solution and solvent removed in vacuo to produce the title compound (0.930 mg).

Step B: Benzyl 2-oxo-1,2-dihydropyridin-3-ylcarbamate

Sodium bicarbonate (1.70 g, 16.89 mmol) and benzyl chloroformate (1.58 g, 9.29 mmol) were added to a solution of 3-aminopyridin-2(1H)-one (0.930 g, 8.45 mmol) in tetrahydrofuran (20 mL). After 7 h, the mixture was extracted with ethyl acetate and saturated sodium bicarbonate. The organic extract was washed with water and saturated brine, dried over magnesium sulfate, filtered, and concentrated. Purification by chromatography [silica gel, 1% to 5% methanol (10% ammonium hydroxide) in dichloromethane gradient elution] gave the title compound (1.304 g). MS 245 (M+1)

Step C: Benzyl 5-iodo-2-oxo-1,2-dihydropyridin-3-ylcarbamate

N-Iodosuccinimide (0.292 g, 1.30 mmol) was added to a solution of benzyl 2-oxo-1,2-dihydropyridin-3-ylcarbamate (0.317 g, 1.3 mmol) in anhydrous dichloromethane (10 mL) and stirred overnight. The mixture was concentrated and purified by chromatography [silica gel, 0% to 50% ethyl acetate in hexanes gradient elution] to give the title compound (0.245 g). MS 371 (M+1)

Step D: Benzyl 1-(cyclopropylmethyl)-5-iodo-2-oxo-1,2-dihydropyridin-3-ylcarbamate Cyclopropylmethyl bromide (0.100 mL, 0.99 mmol) and cesium carbonate (0.323 mg, 0.99 mmol) were added to a solution of benzyl 5-iodo-2-oxo-1,2-dihydropyridin-3-ylcarbamate (0.245 g, 0.66 mmol) in dimethylformamide (3 mL) and stirred overnight. The mixture was diluted with water and extracted with ethyl acetate. The organic layer was washed with saturated brine, dried over magnesium sulfate, filtered, and concentrated. Purification by chromatography (silica gel, 10% to 50% ethyl acetate in hexanes gradient elution) gave the title compound (0.190 g). MS 425 (M+1)

Step E: Benzyl 1-(cyclopropylmethyl)-2-oxo-5-phenyl-1,2-dihydropyridin-3-ylcarbamate Tetrakis(triphenylphosphine)palladium(0) (0.132 mg, 0.11 mmol) and benzyl 1-(cyclopropylmethyl)-5-iodo-2-oxo-1,2-dihydropyridin-3-ylcarbamate (0.097 mg, 0.229 mmol) in tetrahydrofuran (1 mL) were stirred at room temperature for 30 minutes. A solution of phenylboronic acid in ethanol (1 mL) was then added to the reaction mixture. After 1 h, a 2 M solution of sodium carbonate (1 mL) was added and the reaction was heated to reflux. After 3 h, the mixture was allowed to cool to ambient temperature and extracted with ethyl acetate and water. The combined organic extracts were washed with saturated brine, dried over magnesium sulfate, filtered and concentrated. Purification by chromatography (silica gel, 5% to 30% ethyl acetate in hexanes gradient elution) gave the title compound (0.061 g). MS 375 (M+1)

Step F: 3-Amino-1-(cyclopropylmethyl)-5-phenylpiperidin-2-one

Benzyl 1-(cyclopropylmethyl)-2-oxo-5-phenyl-1,2-dihydropyridin-3-ylcarbamate (0.061 g, 0.163 mmol) and 10% palladium on carbon (0.060 g) were stirred in ethanol (15 ml) for 6 h under hydrogen atmosphere (50 psi). Catalyst was filtered from the solution and solvent removed in vacuo to produce the title compound (0.031 mg). MS 245 (M+1)

INTERMEDIATE 17

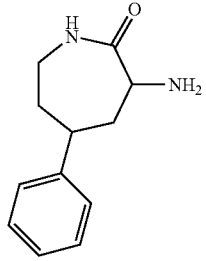

3-Amino-1-(cyclopropylmethyl)-5-phenylazepan-2-one

Step A: (Azidomethyl)cyclopropane

Sodium azide (7.22 g, 111.1 mmol) was added to a solution of cyclopropylmethyl bromide (5.0 g, 37.0 mmol) in N,N-dimethylformamide (20 mL) in a sealed tube and the mixture heated to 110° C. After 5 h, the mixture was cooled to ambient temperature. Water was added, and the mixture was extracted with dichloromethane (3×). The combined organic extracts were washed with water (3×), saturated brine, and dried over sodium sulfate. The solution was decanted to give the title compound in dichloromethane.

Step B:
1-(Cyclopropylmethyl)-5-phenylazepan-2-one

4-Phenylcyclohexone (1.0 g, 5.74 mmol) was added to a solution of (azidomethyl)cyclopropane in dichloromethane (0.238 M). The mixture was cooled to 0° C. and titanium(IV) chloride was added (1 M in dichloromethane; 14.35 mL, 14.35 mmol). After 5 min, the reaction mixture was warmed to ambient temperature. After 18 h, the reaction was quenched with saturated sodium bicarbonate (30 mL). The mixture was extracted with dichloromethane (3×), and the combined organic extracts were washed with water (3×), saturated brine, dried over sodium sulfate, filtered and concentrated. The crude product was purified by silica gel chromatography [100% dichloromethane→97% dichloromethane/3% (10% ammonium hydroxide/methanol)]. The product was re-purified by reverse phase HPLC (C-18 column, 95% water/acetonitrile→5% water/acetonitrile with 0.1% trifluoroacetic acid) to give the title product (0.322 g). MS 244 (M+1).

Step C:
3-Bromo-1-(cyclopropylmethyl)-5-phenylazepan-2-one

Phosphorus pentachloride (0.3 g, 1.44 mmol) was added slowly to a solution of 1-(cyclopropylmethyl)-5-phenylazepan-2-one (0.35 g, 1.44 mmol) in dichloromethane (8 mL) at 0° C. After 1 h, iodine (3.6 mg, 0.01 mmol) and bromine (0.07 mL, 1.44 mmol) were added, and the mixture was allowed to warm to ambient temperature. After 1 h, another 0.3 g of phosphorus pentachloride was added. After an additional 18 h, the reaction was quenched with saturated sodium bicarbonate. The mixture was extracted with dichloromethane (3×), and the combined organic extracts were washed with water (3×), saturated brine, dried over sodium sulfate, filtered and concentrated.

Step D:
3-Azido-1-(cyclopropylmethyl)-5-phenylazepan-2-one

Sodium azide (0.24 g, 3.72 mmol) was added to a solution of 3-bromo-1-(cyclopropylmethyl)-5-phenylazepan-2-one (0.3 g, 0.93 mmol) in acetonitrile (4 mL) and water (1 mL), and the mixture heated to 100° C. After 18 h, the mixture was allowed to cool to ambient temperature and concentrated. Water was added and the mixture was extracted with dichloromethane (3×). The combined organic extracts were washed with water (3×), saturated brine, dried over sodium sulfate, filtered and concentrated.

Step E:
3-Amino-1-(cyclopropylmethyl)-5-phenylazepan-2-one

10% palladium on carbon (30 mg) was added to a solution of 3-azido-1-(cyclopropylmethyl)-5-phenylazepan-2-one (0.3 g, 1.05 mmol) in methanol (4 mL). The reaction vessel was evacuated and back-filled with nitrogen (3×), then back-filled with hydrogen (1 atm). After 18 h, the reaction was filtered and concentrated. Purification by silica gel chromatography [100% dichloromethane→93% dichloromethane/7% (10% ammonium hydroxide/methanol)] gave the title compound (60 mg). The racemic product was resolved on a chiralpak AS (250×20 mm) column using 20% propanol/hexanes→50% propanol/hexanes (0.1% diethylamine in hexanes) to give four enantiomerically pure isomers. MS 259 (M+1).

INTERMEDIATE 18

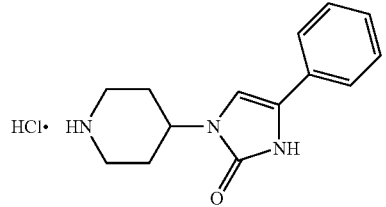

4-Phenyl-1-piperidin-4-yl-1,3-dihydro-2H-imidazol-2-one hydrochloride

4-Phenyl-1-piperidin-4-yl-1,3-dihydro-2H-imidazol-2-one hydrochloride was prepared according to the procedure described in U.S. Pat. No. 6,344,449 B1.

INTERMEDIATE 19

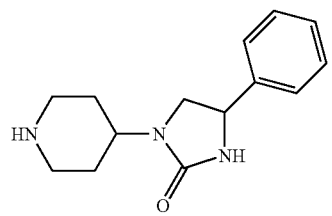

4-Phenyl-1-piperidin-4-yl-imidazolidin-2-one

A solution of 4-phenyl-1-piperidin-4-yl-1,3-dihydro-2H-imidazol-2-one hydrochloride (510 mg, 1.82 mmol) in methanol (10 mL) was hydrogenated at 1 atm hydrogen over palladium on carbon (100 mg). After 4 h, the reaction was filtered and the crude product purified by reverse phase HPLC (C-18, 5% to 95% 0.1% trifluoroacetic acid/acetonitrile in 0.11% aqueous trifluoroacetic acid gradient elution). The title compound was obtained as the trifluoroacetic acid salt (304 mg). MS 246 (M+1)

INTERMEDIATE 20

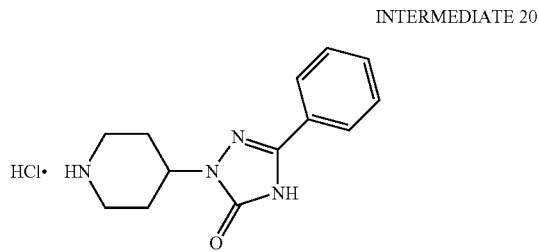

5-Phenyl-1-piperidin-4-yl-2,4-dihydro-3H-1,2,4-triazol-3-one hydrochloride

Step A: 9H-Fluoren-9-ylmethyl 4-[(t-butoxycarbonyl)hydrazono]piperidine-1-carboxylate A solution of 1-[(9H-fluoren-9-yl)methyloxycarbonyl]-4-piperidone (16.0 g, 50.0 mmol) and tert-butyl carbazate 7.25 g, 55.5 mmol) in ethanol (250 mL) was refluxed for 1 h. The solution was cooled and concentrated. Addition of ether (100 mL) produced the title compound as a white precipitate (21.0 g). $^1$H NMR (500 MHz, CDCl$_3$) ☐ 7.77 (d, J=7 Hz, 2H), 7.57 (d, J=7 Hz, 2H), 7.40 (t, J=7 Hz, 2H), 7.32 (t, J=7 Hz, 2H), 4.50 (br s, 2H), 4.24 (t, J=6 Hz, 1H), 3.4-3.7 (br m, 4H), 2.47 (br s, 2H), 2.1-2.2 (br m, 2H), 1.56 (s, 9H).

Step B: 9H-Fluoren-9-ylmethyl 4-[(t-butoxycarbonyl)hydrazino]piperidine-1-carboxylate A solution of 9H-fluoren-9-ylmethyl 4-[(t-butoxycarbonyl)hydrazono]piperidine-1-carboxylate (10.0 g, 22.9 mmol) in acetic acid (150 mL) was shaken with platinum oxide (1.0 g) under 45 psi hydrogen on a Parr apparatus for 2 h. The solution was filtered and concentrated to give the title compound.

Step C: 9H-Fluoren-9-ylmethyl 4-hydrazinopiperidine-1-carboxylate

A solution of 9H-fluoren-9-ylmethyl 4-[(tert-butoxycarbonyl)hydrazino]piperidine-1-carboxylate (20 g, 45.7 mmol) was dissolved in trifluoroacetic acid (100 mL) and stirred at room temperature for 1.5 h. The reaction was concentrated and the residue dissolved in methanol and purified by reverse phase HPLC. Pure fractions were isolated and combined to give the trifluoroacetic acid salt of the title compound (3.01 g). $^1$H NMR (500 MHz, DMSO-d$_6$) ☐ 7.89 (d, J=8 Hz, 2H), 7.61 (d, J=8 Hz, 2H), 7.40 (t, J=8 Hz, 2H), 7.32 (t, J=8 Hz, 2H), 4.33 (d, J=6 Hz, 2H), 4.25 (t, J=6 Hz, 1H), 3.5-4.0 (br s, 6H), 3.05 (br s, 1H), 2.80 (br s, 2H), 1.89 (br s, 2H), 1.2 (br s, 2H).

Step D: 9H-Fluoren-9-ylmethyl 4-(5-oxo-3-phenyl-4,5-dihydro-1H-1,2,4-triazol-1-yl)piperidine-1-carboxylate A solution of 9H-fluoren-9-ylmethyl 4-hydrazinopiperidine-1-carboxylate trifluoroacetic acid salt (2.95 g, 6.54 mmol) was refluxed for 2 h with ethyl N-benzothioyl carbamate (1.50 g, 7.1 mmol) (prepared by the procedure of E. P. Papadopoulus, J. Org. Chem., 1976, 41(6) 962-965) in tetrahydrofuran (30 mL) with diisopropylethyl amine (1.25 mL, 7.1 mmol). The reaction was cooled and concentrated, then dissolved with heating in acetonitrile. A white solid crystallized upon cooling, giving the title compound (2.06 g). $^1$H NMR (500 MHz, CDCl$_3$) ☐ 7.80 (d, J=7 Hz, 2H), 7.77 (d, J=7 Hz, 2H), 7.61 (d, J=7 Hz, 2H), 7.48 (m, 3H), 7.40 (t, J=7 Hz, 2H), 7.33 (t, J=7 Hz, 2H), 4.46 (d, J=6 Hz, 2H), 4.36 (m, 2H), 4.27 (t, J=6 Hz, 1H), 4.26 (br s, 1H), 3.02 (br s, 2H), 2.04 (br s, 2H), 1.94 (br m, 2H).

Step E: 5-Phenyl-1-piperidin-4-yl-2,4-dihydro-3H-1,2,4-triazol-3-one hydrochloride A solution of 9H-fluoren-9-ylmethyl 4-(5-oxo-3-phenyl-4,5-dihydro-1H-1,2,4-triazol-1-yl)piperidine-1-carboxylate (2.06 g, 4.41 mmol) and diethylamine (15 mL) in tetrahydrofuran (15 mL) was stirred at room temperature for 2 h. The reaction was concentrated and the crude product purified by column chromatography (silica gel, 0 to 10% {5% ammonium hydroxide/methanol} in dichloromethane gradient elution), giving the title compound as a white solid (0.95 g). $^1$H NMR (500 MHz, CDCl$_3$) ☐ 7.84 (d, J=7 Hz, 2H), 7.47 (m, 3H), 4.30 (m, 1H), 3.25 (d, J=13 Hz, 2H), 2.79 (t, J=13 Hz, 2H), 2.04 (d, J=4, 12 Hz, 2H), 1.93 (br d, J=10 Hz, 2H).

INTERMEDIATE 21

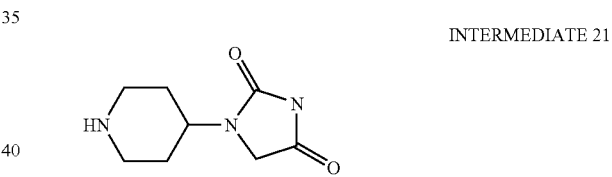

1-Piperidin-4-ylimidazolidine-2,4-dione

Step A: tert-Butyl 4-[(2-ethoxy-2-oxoethyl)amino]piperidine-1-carboxylate

Sodium cyanoborohydride (189 mg, 3.01 mmol) was added to a solution of 1-boc-4-piperidone (500 mg, 2.51 mmol) and glycine ethyl ester hydrochloride (350 mg, 2.51 mmol) in methanol (12.5 mL). After 16 h, the mixture was quenched with saturated ammonium chloride solution, concentrated, and partitioned between dichloromethane and saturated sodium bicarbonate solution. The organic layer was washed with brine, dried over magnesium sulfate, filtered, and concentrated. Purification by silica gel chromatography [100% dichloromethane→95% dichloromethane/5% (10% ammonium hydroxide/methanol)] gave the title compound (600 mg).

Step B: tert-Butyl 4-(2,4-dioxoimidazolidin-1-yl)piperidine-1-carboxylate

Potassium cyanate (31 mg, 0.384 mmol) was added to a solution of tert-butyl 4-[(2-ethoxy-2-oxoethyl)amino]piperidine-1-carboxylate (100 mg, 0.384 mmol) in water (2 mL).

Acetic acid was then added to adjust pH of reaction to 4-5 and the mixture was heated at 40 °C. After 16 h, the reaction was cooled to ambient temperature and purified by reverse phase HPLC (C-18, 95% water/acetonitrile→5% water/acetonitrile with 0.1% trifluoroacetic acid) to give the title compound (33 mg).

Step C: 1-Piperidin-4-ylimidazolidine-2,4-dione

Trifluoroacetic acid (0.300 mL) was added to a solution of tert-butyl 4-(2,4-dioxoimidazolidin-1-yl)piperidine-1-carboxylate (32 mg, 0.113 mmol) in dichloromethane (1 mL). After 4 h, the reaction was concentrated to give the title compound. MS 184.04 (M+1).

INTERMEDIATE 21A

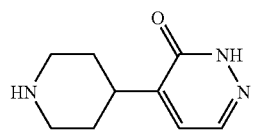

4-Piperidin-4-ylpyridazin-3(2H)-one

Step A. Benzyl 4-[1-(ethoxycarbonyl)but-3-en-1-yl]piperidine-1-carboxylate

To a −78 °C solution of benzyl 4-(2-ethoxy-2-oxoethyl)piperidine-1-carboxylate (5.02 g, 16.4 mmol) in THF (90 mL) was added lithium hexamethyldisilazide (1.0 M in THF, 18.1 mL, 18.1 mmol). After 1 h allyl bromide (2.19 g, 18.1 mmol) was added, the reaction stirred at this temperature for 0.5 h, then warmed to 25 °C. After 3 h the reaction was quenched by the addition of saturated aqueous ammonium chloride and extracted with ethyl acetate (2×). The combined organic layers were dried over MgSO₄, filtered, and concentrated under reduced pressure. The crude product was purified by silica gel chromatography, eluting with a gradient of 0 to 60% EtOAc:hexanes to give the title compound (4.08 g). MS: m/z=346.1 (M+1).

Step B. Benzyl 4-[1-(ethoxycarbonyl)-3-oxopropyl]piperidine-1-carboxylate

Benzyl 4-[1-(ethoxycarbonyl)but-3-en-1-yl]piperidine-1-carboxylate (4.08 g, 11.8 mmol) was dissolved in THF (45 mL), and osmium tetroxide (0.45 mL, 2.5% solution in t-butanol) was added followed by a solution of sodium periodate (7.57 g, 35.4 mmol) in water (37 mL). After 24 h, the reaction was diluted with saturated aqueous Na₂SO₃ and NaHCO₃ and extracted with ethyl acetate (4×). The combined organic washes were dried over sodium sulfate, filtered and evaporated. The crude product was purified by silica gel chromatography, eluting with a gradient of 50 to 100% EtOAc:hexanes to give the title compound (2.39 g). MS: m/z=348.1 (M+1).

Step C. Benzyl 4-(3-oxo-2,3-dihydropyridazin-4-yl)piperidine-1-carboxylate

Benzyl 4-[1-(ethoxycarbonyl)-3-oxopropyl]piperidine-1-carboxylate (2.39 g, 6.89 mmol) was dissolved in acetic acid (100 mL) and hydrazine (4.42 g, 137 mmol) was added. This mixture was heated at 50° C. for 24 h, and then concentrated to dryness. The residue was diluted with saturated aqueous NaHCO₃ and extracted with dichloromethane (3×), the combined organics dried, and concentrated to give a white solid (1.90 g). This material was dissolved in acetonitrile (20 mL), copper(II) chloride (1.62 g, 12.0 mmol) added and the reaction heated to 50° C. After 2 h, the reaction was filtered through celite with dichloromethane. The rinsate was washed with water (75 mL) and the aqueous phase backwashed with dichloromethane (3×). The combined organic washes were washed with 1N HCl, dried and concentrated. The crude product was purified by silica gel chromatography, eluting with a gradient of 0 to 12% MeOH:DCM to give the title compound (0.90 g). MS: m/z=314.1 (M+1).

Step D. 4-Piperidin-4-ylpyridazin-3(2H)-one

A solution of benzyl 4-(3-oxo-2,3-dihydropyridazin-4-yl)piperidine-1-carboxylate (0.90 mg, 2.88 mmol) and 10% Pd/C (500 mg) in EtOH (25 mL), was hydrogenated under a balloon for 4 h. The reaction was filtered through Celite with more EtOH and concentrated to afford the title compound (465 mg). MS 180.1 (M+1).

INTERMEDIATE 22

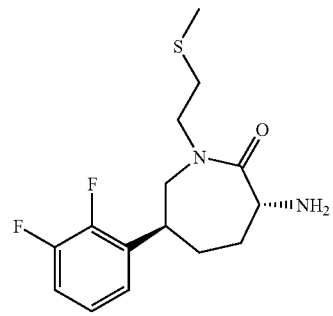

(3R,6S)-3-Amino-6-(2,3-difluorophenyl)-1-[2-(methylthio)ethyl]azepan-2-one

Step A:
2-Bromo-N-(2,4-dimethoxybenzyl)prop-2-en-1-amine

Triethylamine (16.0 mL, 114 mmol) was added to a solution of 2,4-dimethoxybenzylamine hydrochloride (11.1 g, 54.5 mmol) and 2,3-dibromopropene (10.9 g, 54.5 mmol) in dichloromethane (200 mL). After 18 h, water was added and the mixture was extracted with dichloromethane (3×). The combined organic extracts were washed with saturated brine, dried over magnesium sulfate, filtered and concentrated. Purification by silica gel chromatography [100% dichloromethane→95% dichloromethane/5% (10% ammonium hydroxide/methanol)] gave the title compound (7.85 g).

Step B: Benzyl (1R)-1-{[(2-bromoprop-2-enyl)(2,4-dimethoxybenzyl)amino]carbonyl}but-3-enylcarbamate 1-[3-(Dimethylamino)propyl]-3-ethylcarbodiimide hydrochloride (55 mg, 0.285 mmol) was added to a solution of 2-bromo-N-(2,4-dimethoxybenzyl)prop-2-en-1-amine (73 mg, 0.256 mmol) and (2R)-2-{[(benzyloxy)carbonyl]amino}pent-4-enoic acid (71 mg, 0.285 mmol) in dichloromethane (5 mL). After 18 h the mixture was concentrated. Purification by silica gel chromatography (5% ethyl acetate/hexanes→30% ethyl acetate/hexanes) gave the title compound (77 mg). MS 517 (M+1).

Step C: Benzyl (1R)-1-{[[2-(2,3-difluorophenyl)prop-2-enyl](2,4-dimethoxybenzyl)amino]carbonyl}but-3-enylcarbamate Dichloro[1,1'-bis(diphenylphosphino)ferrocene]palladium dichloromethane adduct (0.726 g, 0.889 mmol) was added to a solution of benzyl (1R)-1-{[(2-bromoprop-2-enyl)(2,4-dimethoxybenzyl)amino]carbonyl}but-3-enylcarbamate (9.2 g, 17.8 mmol), 2,3-difluorophenylboronic acid (2.95 g, 18.7 mmol) and sodium carbonate (2 M in water; 19.6 mL, 39.1 mmol) in N,N-dimethylformamide (60 mL) and heated to 75 °C. After 2 h, the mixture was allowed to cool to ambient temperature and extracted with dichloromethane (3×). The combined organic extracts were washed with saturated brine, dried over magnesium sulfate, filtered and concentrated. Purification by silica gel chromatography (5% ethyl acetate/hexanes→55% ethyl acetate/hexanes) gave the title compound (6.8 g). MS 551.2 (M+1).

Step D: Benzyl (3R)-6-(2,3-difluorophenyl)-1-(2,4-dimethoxybenzyl)-2-oxo-2,3,4,7-tetrahydro-1H-azepin-3-ylcarbamate

[1,3-Bis-(2,4,6-trimethylphenyl-2-imidazolidinylidene)dichloro(phenylmethylene)-(tricyclohexylphosphine)ruthenium] (Grubbs second generation catalyst) (2.62 g, 3.09 mmol) was added to a solution of benzyl (1R)-1-{[[2-(2,3-difluorophenyl)prop-2-enyl](2,4-dimethoxybenzyl)amino]carbonyl}but-3-enylcarbamate (6.8 g, 12.35 mmol) in dichloromethane (1800 mL) and heated to 40 °C. After 48 h, additional catalyst (0.52 g, 0.613 mmol) was added and the reaction heated at 40 °C for an additional 48 h. The mixture was allowed to cool to ambient temperature and concentrated. Purification by silica gel chromatography (5% ethyl acetate/hexanes→55% ethyl acetate/hexanes) gave the title compound (3.71 g). MS 523.1 (M+1).

Step E: Benzyl (3R)-6-(2,3-difluorophenyl)-2-oxo-2,3,4,7-tetrahydro-1H-azepin-3-ylcarbamate Trifluoroacetic acid (60 mL) was added to a solution of benzyl (3R)-6-(2,3-difluorophenyl)-1-(2,4-dimethoxybenzyl)-2-oxo-2,3,4,7-tetrahydro-1H-azepin-3-ylcarbamate (3.70 g, 7.08 mmol) in dichloromethane (40 mL). After 18 h, the mixture was concentrated at 25 °C, methanol (150 mL) was added, and the precipitate filtered. The filtrate was concentrated and diluted with dichloromethane (100 mL). The mixture was extracted with water (2×), saturated aqueous sodium bicarbonate (2×), and saturated brine, dried over magnesium sulfate, filtered and concentrated. Purification by silica gel chromatography (5% ethyl acetate/hexanes→65% ethyl acetate/hexanes) gave the title compound (1.75 g). MS 373.1 (M+1).

Step F: tert-Butyl (3R,6S)-6-(2,3-difluorophenyl)-2-oxoazepan-3-ylcarbamate

10% palladium on carbon (700 mg) was added to a solution of benzyl (3R)-6-(2,3-difluorophenyl)-2-oxo-2,3,4,7-tetrahydro-1H-azepin-3-ylcarbamate (2.6 g, 6.98 mmol) and di-tert-butyl dicarbonate (5.03 g, 23.0 mmol) in toluene (200 mL). The reaction vessel was evacuated and back-filled with nitrogen (3×), then back-filled with hydrogen (1 atm). After 24 h, the mixture was filtered and concentrated. Purification by preparative reverse phase chromatography (DeltaPak C18, 15 □, 47 mm×300 mm, 70 mL/min: 80% H₂O/NH₄OAc: 20% CH₃CN to 100% CH₃CN over 60 min) afforded the pure trans title compound (1.2 g). MS 341.2 (M+1).

Step G: tert-Butyl (3R,6S)-6-(2,3-difluorophenyl)-1-[2-(methylthio)ethyl]-2-oxoazepan-3-ylcarbamate Sodium hydride (60% dispersion in mineral oil; 40 mg, 0.600 mmol) was added to a solution of tert-butyl (3R,6S)-6-(2,3-difluorophenyl)-2-oxoazepan-3-ylcarbamate (170 mg, 0.500 mmol) in N,N-dimethylformamide (4 mL) at 0 °C. After 5 minutes the mixture was cooled to −30° C. and 1-iodo-2-(methylthio)ethane [prepared according to known procedures: J. Org. Chem., 1987, 52, 2299-2301 (158 mg, 0.782 mmol)] was added. Additional sodium hydride (33 mg, 0.495 mmol) was added and after 4 h excess sodium hydride (33 mg, 0.495 mmol) and 1-iodo-2-(methylthio)ethane (75.6 mg, 0.374 mmol) were added. After 3 h, the final portions of sodium hydride (33 mg, 0.495 mmol) and 1-iodo-2-(methylthio)ethane (75.6 mg, 0.374 mmol) were added and the mixture stirred at −20° C. overnight. The reaction was quenched with water and the mixture was extracted with ethyl acetate. The organic layer was washed with water (3×), saturated brine, dried over magnesium sulfate, filtered and concentrated. Purification by silica gel chromatography (0% ethyl acetate/hexanes→50% ethyl acetate/hexanes) gave the title compound (77 mg). MS 415 (M+1).

Step H: (3R,6S)-3-Amino-6-(2,3-difluorophenyl)-1-[2-(methylthio)ethyl]azepan-2-one Trifluoroacetic acid (2 mL) was added to a solution of tert-butyl (3R,6S)-6-(2,3-difluorophenyl)-1-[2-(methylthio)ethyl]-2-oxoazepan-3-ylcarbamate (77 mg, 0.186 mmol) in dichloromethane (10 mL). After 30 min, the solution was concentrated and azeotroped with toluene (2×). Saturated aqueous sodium bicarbonate solution was added and the mixture was extracted with dichloromethane (3×). The combined organic extracts were washed with saturated brine, dried over magnesium sulfate, filtered and concentrated. MS 315.2 (M+1).

Essentially following the procedures outlined for the preparation of Intermediate 20, the Intermediates in Table 4 were prepared.

TABLE 4

| Intermediate | Structure | MS (M + 1) |
| --- | --- | --- |
| 23 | [structure] | 285.2 |

TABLE 4-continued

| Intermediate | Structure | MS (M + 1) |
|---|---|---|
| 24 | 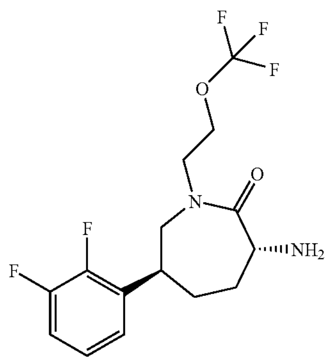 | 353.2 |
| 25 | 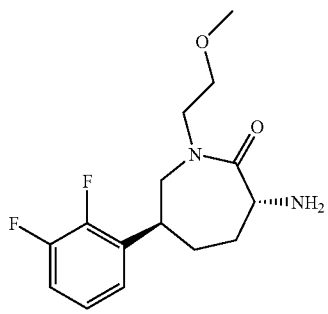 | 299.2 |

Example 1

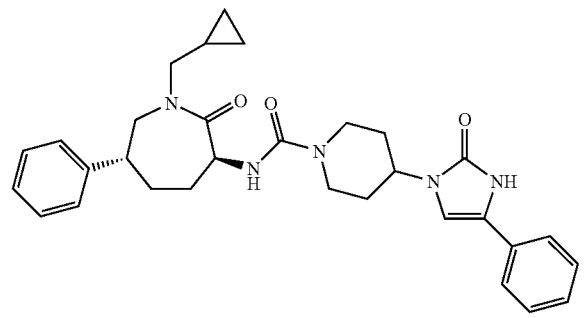

N-[(3S,6R)-1-(cyclopropylmethyl)-2-oxo-6-phenylazepan-3-yl]-4-(2-oxo-4-phenyl-2,3-dihydro-1H-imidazol-1-yl)piperidine-1-carboxamide Triethylamine (0.070 mL, 0.51 mmol) was added to a solution of 3-amino-1-(cyclopropylmethyl)-6-phenylazepan-2-one (131 mg, 0.51 mmol) and p-nitrophenyl chloroformate (102 mg, 0.51 mmol) in tetrahydrofuran (5 mL) at 0° C. After 0.5 h, triethylamine (0.18 mL, 1.28 mmol) and 4-(2-oxo-4-phenyl-2,3-dihydro-1H-imidazol-1-yl)piperidinium chloride (142 mg, 0.51 mmol) were added and the mixture was allowed to warm to ambient temperature. After 2 h, the mixture was concentrated. Purification by preparative reverse phase chromatography (DeltaPak C18, 15 □, 47 mm×300 mm, 65 mL/min: 5% CH$_3$CN to 95% CH$_3$CN over 60 min) afforded the racemic compound. The cis and trans enantiomers were both separated using a Chiralcel AD column eluting with 30% 2-propanol/hexanes→70% propanol/hexanes (0.1% diethylamine in hexanes) to give the title compound (50 mg). MS 528.3 (M+1)

Essentially following the procedure outlined for the preparation of Example 1, the Examples in Table 5 were prepared.

TABLE 5

| Example | R | MS (M + 1) |
|---|---|---|
| 2 | | 488.3 |
| 3 | | 588.3 |
| 4 | | 528.3 |
| 5 | | 528.3 |

TABLE 5-continued

| Example | R | MS (M + 1) |
|---|---|---|
| 6 | cyclopropylmethyl-phenyl-thiazepanone-NH- | 546.3 |
| 7 | cyclopropylmethyl-phenyl-thiazepanone dioxide-NH- | 600.2 (M + Na) |
| 8 | cyclopropylmethyl-phenyl-piperidinone-NH- | 514.2 |
| 9 | isobutyl-phenyl-pyrrolidinone-NH- racemic | 502.3 |
| 10 | isobutyl-phenyl-pyrrolidinone-NH- racemic | 502.3 |

TABLE 5-continued

| Example | R | MS (M + 1) |
|---|---|---|
| 11 | cyclopropylmethyl-phenyl-oxazepanone-NH- racemic | 530.2 |
| 12 | cyclopropylmethyl-phenyl-oxazepanone-NH- racemic | 530.2 |
| 13 | cyclopropylmethyl-phenyl-oxazepanone-NH- | 530.3 |
| 14 | cyclopropylmethyl-phenyl-azepanone-NH- racemic | 528.3 |

TABLE 5-continued

| Example | R | MS (M + 1) |
|---|---|---|
| 15 | (cyclopropylmethyl azepanone with phenyl, racemic) | 528.3 |
| 16 | (methylthioethyl azepanone with 2,3-difluorophenyl) | 584.3 |
| 17 | (hydroxyethyl azepanone with 2,3-difluorophenyl) | 554.3 |
| 18 | (trifluoromethoxyethyl azepanone with 2,3-difluorophenyl) | 622.3 |

TABLE 5-continued

| Example | R | MS (M + 1) |
|---|---|---|
| 19 | (methoxyethyl azepanone with 2,3-difluorophenyl) | 568.3 |

Example 20 tert-Butyl (2S,6R and 2R,6S)-4-(cyclopropylmethyl)-5-oxo-6-({[4-(2-oxo-4-phenyl-2,3-dihydro-1H-imidazol-1-yl)piperidin-1-yl]carbonyl}amino)-2-phenyl-1,4-diazepane-1-carboxylate Triethylamine (0.060 mL, 0.42 mmol) was added to a solution of tert-butyl (2R,6S and 2S,6R)-6-amino-4-(cyclopropylmethyl)-5-oxo-2-phenyl-1,4-diazepane-1-carboxylate (152 mg, 0.423 mmol) and p-nitrophenyl chloroformate (85 mg, 0.42 mmol) in tetrahydrofuran (5 mL) at 0° C. After 1 h, triethylamine (0.18 mL, 1.26 mmol), 4-(2-oxo-4-phenyl-2,3-dihydro-1H-imidazol-1-yl)piperidinium chloride (118 mg, 0.42 mmol) and dichloromethane (5 mL) were added and the mixture was allowed to warm to ambient temperature. After 4 h, the mixture was diluted with saturated aqueous sodium carbonate. The mixture was extracted with ethyl acetate, washed with saturated aqueous sodium carbonate and saturated brine, dried over magnesium sulfate, filtered, and concentrated. Purification by silica gel chromatography (1% methanol/dichloromethane→5% methanol/dichloromethane) gave the title compound (215 mg). MS 629.3 (M+1).

Example 21

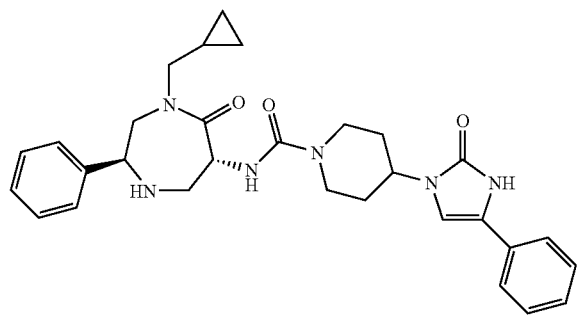

N-[(3S,6R)-1-(Cyclopropylmethyl)-7-oxo-3-phenyl-1,4-diazepan-6-yl]-4-(2-oxo-4-phenyl-2,3-dihydro-1H-imidazol-1-yl)piperidine-1-carboxamide and N-[(3R,6S))-1-(cyclopropylmethyl)-7-oxo-3-phenyl-1,4-diazepan-6-yl]-4-(2-oxo-4-phenyl-2,3-dihydro-1H-imidazol-1-yl)piperidine-1-carboxamide Step A: N-[(3S,6R and 3R,6S)-1-(Cyclopropylmethyl)-7-oxo-3-phenyl-1,4-diazepan-6-yl]-4-(2-oxo-4-phenyl-2,3-dihydro-1H-imidazol-1-yl)piperidine-1-carboxamide Trifluoroacetic acid (3 mL) was added to a solution of tert-butyl (2S,6R and 2R,6S)-4-(cyclopropylmethyl)-5-oxo-6-({[4-(2-oxo-4-phenyl-2,3-dihydro-1H-imidazol-1-yl)piperidin-1-yl]carbonyl}amino)-2-phenyl-1,4-diazepane-1-carboxylate (201 mg, 0.32 mmol) in dichloromethane (10 mL). After 30 min, the mixture was concentrated and saturated aqueous sodium bicarbonate was added. The mixture was extracted with dichloromethane (3×), and the combined organic extracts were dried over magnesium sulfate, filtered, and concentrated. Purification by silica gel chromatography [100% dichloromethane→95% dichloromethane/[10% ammonium hydroxide/methanol)] gave the racemic trans compound (183 mg). MS 529.2 (M+1). $^1$H NMR (500 MHz, CDCl$_3$) □ 9.57 (br s, 1H), 7.42-7.35 (m, 7H), 7.31 (t, J=7.2 Hz, 1H), 7.27-7.23 (m, 2H), 6.51 (s, 1H), 6.24 (d, J=4.4 Hz, 1H), 4.82-4.80 (m, 1H), 4.32-4.27 (m, 1H), 4.25-4.18 (m, 2H), 3.92-3.86 (m, 2H), 3.69 (dd, J=13.9, 6.7 Hz, 1H), 3.40 (dd, J=12.4, 2.0 Hz, 1H), 3.32 (d, J=13.9 Hz, 1H), 3.08 (dd, J=13.9, 7.3 Hz, 1H), 2.97 (t, J=12.9 Hz, 2H), 2.85 (dd, J=12.2, 10.3 Hz, 1H), 2.02 (d, J=10.8 Hz, 2H), 1.78-1.63 (m, 3H), 1.06-1.01 (m, 2H), 0.31-0.25 (m, 2H).

Step B: N-[(3S,6R)-1-(Cyclopropylmethyl)-7-oxo-3-phenyl-1,4-diazepan-6-yl]-4-(2-oxo-4-phenyl-2,3-dihydro-1H-imidazol-1-yl)piperidine-1-carboxamide and N-[(3R,6S))-1-(cyclopropylmethyl)-7-oxo-3-phenyl-1,4-diazepan-6-yl]-4-(2-oxo-4-phenyl-2,3-dihydro-1H-imidazol-1-yl)piperidine-1-carboxamide The trans enantiomers were separated using a Chirlpak AD column eluting with 60% (hexanes with 0.1% trifluoroacetic acid) and 40% isopropanol to give the final products. MS 529.3 (M+1) for both.

Example 22

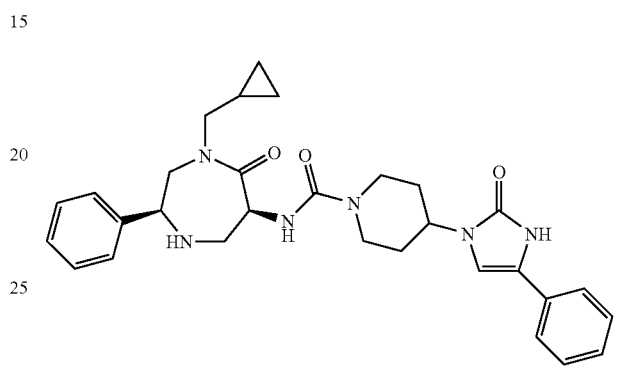

N-[(3S,6S and 3R,6R)-1-(Cyclopropylmethyl)-7-oxo-3-phenyl-1,4-diazepan-6-yl]-4-(2-oxo-4-phenyl-2,3-dihydro-1H-imidazol-1-yl)piperidine-1-carboxamide Step A: tert-Butyl (3S,6S and 3R,6R)-4-(cyclopropylmethyl)-5-oxo-6-({[4-(2-oxo-4-phenyl-2,3-dihydro-1H-imidazol-1-yl)piperidin-1-yl]carbonyl}amino)-2-phenyl-1,4-diazepane-1-carboxylate Triethylamine (0.010 mL, 0.060 mmol) was added to a solution of tert-butyl (2R,6R and 2S,6S)-6-amino-4-(cyclopropylmethyl)-5-oxo-2-phenyl-1,4-diazepane-1-carboxylate (22 mg, 0.061 mmol) and p-nitrophenyl chloroformate (12.3 mg, 0.061 mmol) in tetrahydrofuran (2.5 mL) at 0° C. After 1 h, triethylamine (0.030 mL, 0.180 mmol), 4-(2-oxo-4-phenyl-2,3-dihydro-1H-imidazol-1-yl)piperidinium chloride (17.1 mg, 0.061 mmol) and dichloromethane (2.5 mL) were added and the mixture was allowed to warm to ambient temperature. After 4 h, the mixture concentrated to give the crude compound. MS 629 (M+1).

Step B: N-[(3S,6S and 6R,3R)-1-(Cyclopropylmethyl)-7-oxo-3-phenyl-1,4-diazepan-6-yl]-4-(2-oxo-4-phenyl-2,3-dihydro-1H-imidazol-1-yl)piperidine-1-carboxamide Trifluoroacetic acid (3 mL) was added to a solution of tert-butyl (3S,6S and 3R,6R)-4-(cyclopropylmethyl)-5-oxo-6-({[4-(2-oxo-4-phenyl-2,3-dihydro-1H-imidazol-1-yl)piperidin-1-yl]carbonyl}amino)-2-phenyl-1,4-diazepane-1-carboxylate (38.4 mg, 0.060 mmol) in dichloromethane (10 mL). After 30 min, the mixture was concentrated and saturated aqueous sodium bicarbonate was added. The mixture was extracted with dichloromethane (3×), and the combined organic extracts were dried over magnesium sulfate, filtered, and concentrated. Purification by silica gel chromatography

[99% dichloromethane→95% dichloromethane/[10% ammonium hydroxide/methanol)] gave the title compound (18 mg). MS 529.3 (M+1).

Example 23

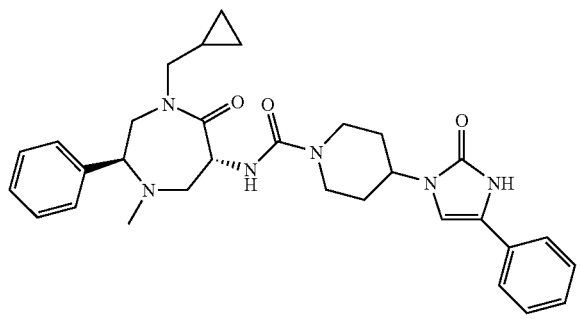

N-[(2S,6R)-4-(Cyclopropylmethyl)-1-methyl-5-oxo-2-phenyl-1,4-diazepan-6-yl]-4-(2-oxo-4-phenyl-2,3-dihydro-1H-imidazol-1-yl)piperidine-1-carboxamide Potassium carbonate (5.8 mg, 0.040 mmol) was added to a solution of N-[(3R,6S)-1-(cyclopropylmethyl)-7-oxo-3-phenyl-1,4-diazepan-6-yl]-4-(2-oxo-4-phenyl-2,3-dihydro-1H-imidazol-1-yl)piperidine-1-carboxamide (11.0 mg, 0.021 mmol) and iodomethane (3 □L, 0.040 mmol) in acetone (0.5 mL). After 18 h, the mixture was concentrated. Purification by silica gel chromatography (1% methanol/dichloromethane→5% methanol/dichloromethane) gave the title compound (4 mg). MS 543.3 (M+1).

Example 24

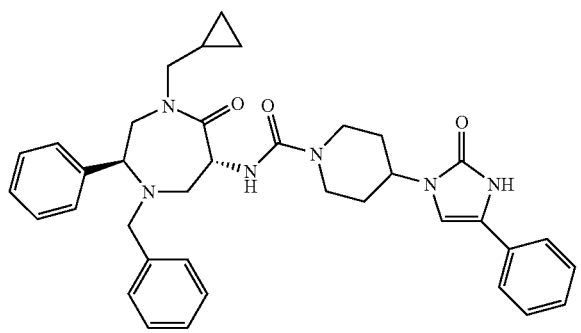

N-[(2S,6R)-1-Benzyl-4-(cyclopropylmethyl)-5-oxo-2-phenyl-1,4-diazepan-6-yl]-4-(2-oxo-4-phenyl-2,3-dihydro-1H-imidazol-1-yl)piperidine-1-carboxamide Potassium carbonate (6.4 mg, 0.05 mmol) was added to a solution of N-[(3R,6S)-1-(cyclopropylmethyl)-7-oxo-3-phenyl-1,4-diazepan-6-yl]-4-(2-oxo-4-phenyl-2,3-dihydro-1H-imidazol-1-yl)piperidine-1-carboxamide (12.2.0 mg, 0.023 mmol) and benzyl bromide (14 □L, 0.12 mmol) in acetone (0.5 mL). After 18 h, the mixture was concentrated. Purification by silica gel chromatography (1% methanol/dichloromethane→5% methanol/dichloromethane) gave the title compound (11 mg). MS 619.3 (M+1).

Example 25

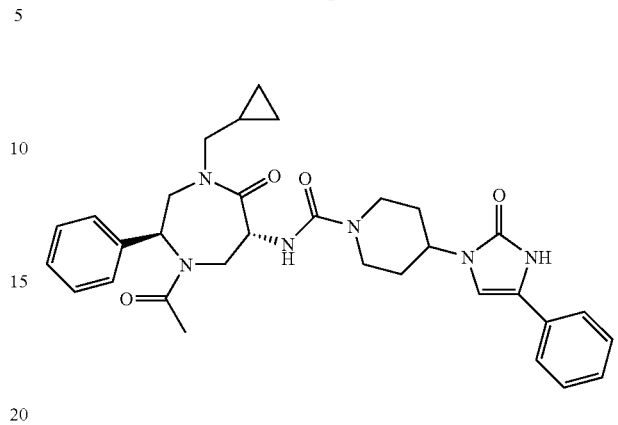

N-[(2S,6R)-1-Acetyl-4-(cyclopropylmethyl)-5-oxo-2-phenyl-1,4-diazepan-6-yl]-4-(2-oxo-4-phenyl-2,3-dihydro-1H-imidazol-1-yl)piperidine-1-carboxamide Acetyl chloride (2.1 □L, 0.03 mmol) was added to a solution of N-[(3R,6S)-1-(cyclopropylmethyl)-7-oxo-3-phenyl-1,4-diazepan-6-yl]-4-(2-oxo-4-phenyl-2,3-dihydro-1H-imidazol-1-yl)piperidine-1-carboxamide (16.9 mg, 0.03 mmol) and triethylamine (9 □L, 0.06 mmol) in dichloromethane (0.5 mL). After 30 min, the mixture was concentrated. Purification by silica gel chromatography (1% methanol/dichloromethane→5% methanol/dichloromethane) gave the title compound (17 mg). MS 571.3 (M+1).

Example 26

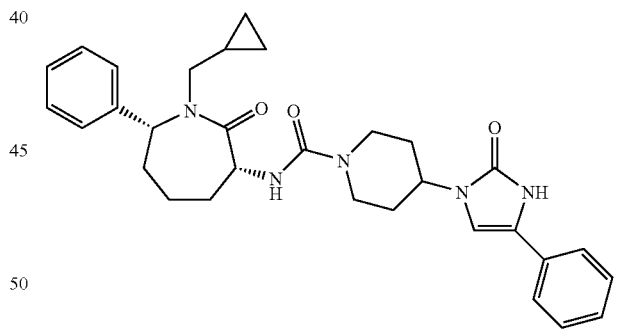

N-[(3R,7R)-1-(cyclopropylmethyl)-2-oxo-7-phenylazepan-3-yl]-4-(2-oxo-4-phenyl-2,3-dihydro-1H-imidazol-1-yl)piperidine-1-carboxamide Diisopropylethylamine (0.020 mL, 0.11 mmol) and phosgene (0.06 mL, 0.56 mmol) were added to a solution of 4-(2-oxo-4-phenyl-2,3-dihydro-1H-imidazol-1-yl)piperidinium chloride (27 mg, 0.111 mmol) in dichloromethane (1 mL) at 0° C. After 30 min, the mixture was concentrated in vacuo and azeotroped with dichloromethane (2×) to give the crude amine. Diisopropylethylamine (0.04 ml, 0.22 mmol) was added to a solution of the crude amine and (3R,7R)-3-amino-1-(cyclopropylmethyl)-7-phenylazepan-2-one (28.7 mg, 0.11 mmol) in dichloromethane (1 mL) and the mixture heated to reflux. After 15 min, the mixture was concentrated and purified by silica gel chromatography (1% methanol/dichloromethane—5% methanol/dichloromethane) gave the title compound (38 mg). MS 528.3 (M+1).

Essentially following the procedure outlined for the preparation of Example 26, the Examples in Table 6 were prepared.

TABLE 6

| Example | R | MS (M + 1) |
|---|---|---|
| 27 | | 510.3 (M + Na) |
| 28 | | 594.3 |

Example 29

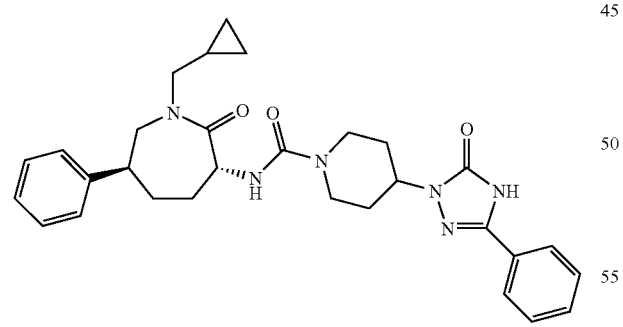

N-[(3R,6S)-1-(Cyclopropylmethyl)-2-oxo-6-phenylazepan-3-yl]-4-(5-oxo-3-phenyl-4,5-dihydro-1H-1,2,4-triazol-1-yl)piperidine-1-carboxamide Triethylamine (0.006 mL, 0.035 mmol) was added to a solution of (3R,6S)-3-amino-1-(cyclopropylmethyl)-6-phenylazepan-2-one (9 mg, 0.035 mmol) and p-nitrophenyl chloroformate (7 mg, 0.035 mmol) in tetrahydrofuran (0.500 mL) at 0° C. After 0.5 h, diisopropylethylamine (0.027 mL, 0.14 mmol), 5-phenyl-1-piperidin-4-yl-2,4-dihydro-3H-1,2,4-triazol-3-one hydrochloride (9 mg, 0.035 mmol), and dichloromethane (0.500 mL) were added and the mixture was heated to reflux. After 2 h, the mixture was concentrated. Purification by reverse phase HPLC (C-18, 95% water/acetonitrile→5% water/acetonitrile with 0.1% trifluoroacetic acid) gave the title compound. MS 529.3 (M+1).

Essentially following the procedure outlined for the preparation of Example 29, the Examples in Table 7 were prepared.

TABLE 7

| Example | R | MS (M + 1) |
|---|---|---|
| 30 | | 531.3 |
| 31 | | 529.3 racemic |
| 32 | | 529.3 racemic |

Example 33

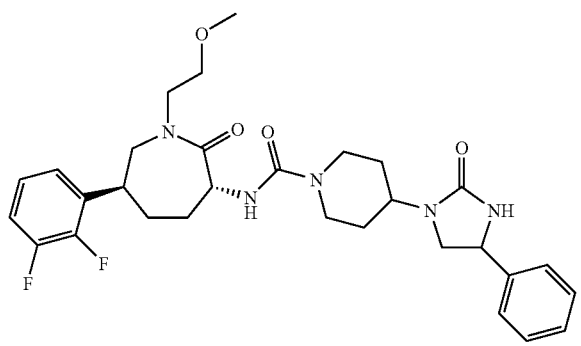

N-[(3R,6S)-6-(2,3-difluorophenyl)-1-(2-methoxyethyl)-2-oxoazepan-3-yl]-4-(2-oxo-4-phenylimidazolidin-1-yl)piperidine-1-carboxamide Triethylamine (0.012 mL, 0.084 mmol) was added to a solution (3R,6S)-3-amino-6-(2,3-difluorophenyl)-1-(2-methoxyethyl)azepan-2-one (25 mg, 0.084 mmol) and p-nitrophenyl chloroformate (25 mg, 0.126 mmol) in tetrahydrofuran (1 mL) at 0° C. After 0.5 h, triethylamine (0.036 mL, 0.252 mmol) and 4-phenyl-1-piperidin-4-yl-imidazolidin-2-one (31 mg, 0.126 mmol) were added and the mixture was allowed to warm to ambient temperature. After 1 h, the mixture was quenched with water, extracted with dichloromethane, and washed with 1 N NaOH solution. The combined organic layer was dried over sodium sulfate, filtered, and concentrated. Purification by silica gel chromatography (0.5% methanol/dichloromethane→6% methanol/dichloromethane) gave the title compound (11 mg). MS 570.3 (M+1).

Example 34

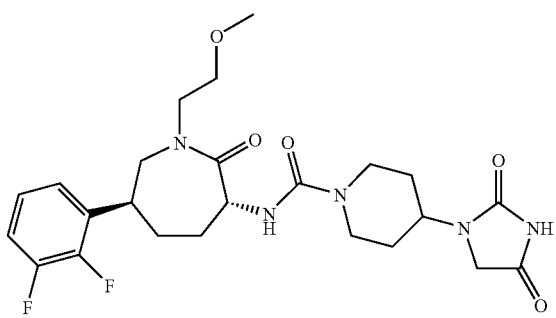

N-[(3R,6S)-6-(2,3-difluorophenyl)-1-(2-methoxyethyl)-2-oxoazepan-3-yl]-4-(2,4-dioxoimidazolidin-1-yl)piperidine-1-carboxamide Triethylamine (0.012 mL, 0.084 mmol) was added to a solution (3R,6S)-3-amino-6-(2,3-difluorophenyl)-1-(2-methoxyethyl)azepan-2-one (25 mg, 0.084 mmol) and p-nitrophenyl chloroformate (25 mg, 0.126 mmol) in tetrahydrofuran (1 mL) at 0° C. After 0.5 h, triethylamine (0.036 mL, 0.252 mmol) and 1-piperidin-4-ylimidazolidine-2,4-dione (23 mg, 0.126 mmol) were added and the mixture was allowed to warm to ambient temperature. After 1 h, the mixture was quenched with water, extracted with ethyl acetate, and washed with 1 N NaOH solution. The combined organic layer was dried over sodium sulfate, filtered, and concentrated. Purification by silica gel chromatography (0.5% methanol/dichloromethane→7% methanol/dichloromethane) gave the title compound (9 mg). MS 508.2 (M+1).

Example 35

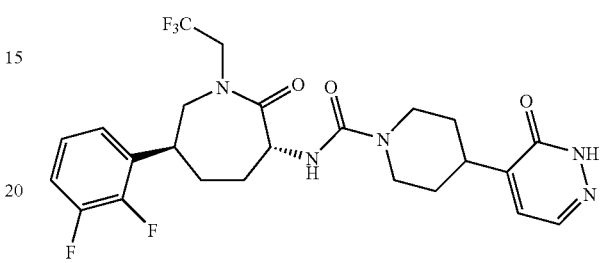

N-[(3R,6S)-6-(2,3-difluorophenyl)-2-oxo-1-(2,2,2-trifluoroethyl)azepan-3-yl]-4-(3-oxo-2,3-dihydropyridazin-4-yl)piperidine-1-carboxamide Triethylamine (11.5 mg, 0.104 mmol) was added to a solution (3R,6S)-3-amino-6-(2,3-difluorophenyl)-1-(2,2,2-trifluoroethyl)azepan-2-one (32 mg, 0.104 mmol) and p-nitrophenyl chloroformate (20 mg, 0.104 mmol) in tetrahydrofuran (1 mL) at 0° C. After 0.5 h, triethylamine (42 mg, 10.416 mmol) and 4-piperidin-4-ylpyridazin-3(2H)-one (19 mg, 0.104 mmol) were added and the mixture was allowed to warm to ambient temperature. After 1 h, the mixture was quenched with water, extracted with ethyl acetate, and washed with 1 N NaOH solution. The combined organic layer was dried over sodium sulfate, filtered, and concentrated. Purification by silica gel chromatography (1% methanol/dichloromethane→10% methanol/dichloromethane) gave the title compound (30 mg). MS 528.1999 (M+1).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above.

What is claimed is:
1. The compound of Formula I:

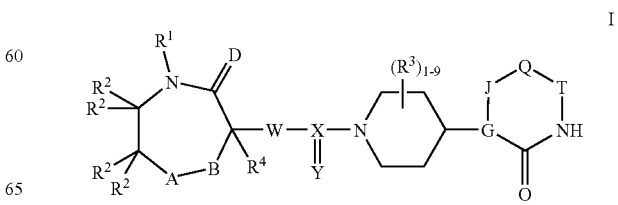

wherein:
A is a bond, $C(R^2)_2$, O, $S(O)_m$ or $NR^2$;
B is $(C(R^2)_2)_n$;
D is O;
$R^1$ is selected from:
1) H, $C_1$-$C_6$ alkyl, $C_2$-$C_6$ alkenyl, $C_2$-$C_6$ alkynyl, $C_{3-6}$ cycloalkyl, and heterocycle, unsubstituted or substituted with one or more substituents independently selected from:
  a) $C_{1-6}$ alkyl,
  b) $C_{3-6}$ cycloalkyl,
  c) aryl, unsubstituted or substituted with 1-5 substituents where the substituents are independently selected from $R^4$,
  d) heteroaryl, unsubstituted or substituted with 1-5 substituents where the substituents are independently selected from $R^4$,
  e) heterocycle, unsubstituted or substituted with 1-5 substituents where the substituents are independently selected from $R^4$,
  f) $(F)_p C_{1-3}$ alkyl,
  g) halogen,
  h) $OR^4$,
  i) $O(CH_2)_s OR^4$,
  j) $CO_2 R^4$,
  k) $(CO)NR^{10}R^{11}$,
  l) $O(CO)NR^{10}R^{11}$,
  m) $N(R^4)(CO)NR^{10}R^{11}$,
  n) $N(R^{10})(CO)R^{11}$,
  o) $N(R^{10})(CO)OR^{11}$,
  p) $SO_2 NR^{10}R^{11}$,
  q) $N(R^{10})SO_2 R^{11}$,
  r) $S(O)_m R^{10}$,
  s) CN,
  t) $NR^{10}R^{11}$,
  u) $N(R^{10})(CO)NR^4 R^{11}$, and
  v) $O(CO)R^4$;
2) aryl or heteroaryl, unsubstituted or substituted with one or more substituents independently selected from:
  a) $C_{1-6}$ alkyl,
  b) $C_{3-6}$ cycloalkyl,
  c) aryl, unsubstituted or substituted with 1-5 substituents where the substituents are independently selected from $R^4$,
  d) heteroaryl, unsubstituted or substituted with 1-5 substituents where the substituents are independently selected from $R^4$,
  e) heterocycle, unsubstituted or substituted with 1-5 substituents where the substituents are independently selected from $R^4$,
  f) $(F)_p C_{1-3}$ alkyl,
  g) halogen,
  h) $OR^4$,
  i) $O_{(CH2)_s} OR^4$,
  j) $CO_2 R^4$,
  k) $(CO)NR^{10}R^{11}$,
  l) $O(CO)NR^{10}R^{11}$,
  m) $N(R^4)(CO)NR^{10}R^{11}$,
  n) $N(R^{10})(CO)R^{11}$,
  o) $N(R^{10})(CO)OR^{11}$,
  p) $SO_2 NR^{10}R^{11}$,
  q) $N(R^{10})SO_2 R^{11}$,
  r) $S(O)_m R^{10}$,
  s) CN,
  t) $NR^{10}R^{11}$,
  u) $N(R^{10})(CO)NR^4 R^{11}$, and
  v) $O(CO)R^4$;
$R^2$ is independently selected from:
1) H, $C_0$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
  a) $C_{1-6}$ alkyl,
  b) $C_{3-6}$ cycloalkyl,
  c) aryl, unsubstituted or substituted with 1-5 substituents where the substituents are independently selected from $R^4$,
  d) heteroaryl, unsubstituted or substituted with 1-5 substituents where the substituents are independently selected from $R^4$,
  e) heterocycle, unsubstituted or substituted with 1-5 substituents where the substituents are independently selected from $R^4$,
  f) $(F)_p C_{1-3}$ alkyl,
  g) halogen,
  h) $OR^4$,
  i) $O(CH_2)_s OR^4$,
  j) $CO_2 R^4$,
  k) $(CO)NR^{10}R^{11}$,
  l) $O(CO)NR^{10}R^{11}$,
  m) $N(R^4)(CO)NR^{10}R^{11}$,
  n) $N(R^{10})(CO)R^{11}$,
  o) $N(R^{10})(CO)OR^{11}$,
  p) $SO_2 NR^{10}R^{11}$,
  q) $N(R^{10})SO_2 R^{11}$,
  r) $S(O)_m R^{10}$,
  s) CN,
  t) $NR^{10}R^{11}$,
  u) $N(R^{10})(CO)NR^4 R^{11}$, and,
  v) $O(CO)R^4$; and,
2) aryl or heteroaryl, unsubstituted or substituted with one or more substituents independently selected from:
  a) $C_{1-6}$ alkyl,
  b) $C_{3-6}$ cycloalkyl,
  c) aryl, unsubstituted or substituted with 1-5 substituents where the substituents are independently selected from $R^4$,
  d) heteroaryl, unsubstituted or substituted with 1-5 substituents where the substituents are independently selected from $R^4$,
  e) heterocycle, unsubstituted or substituted with 1-5 substituents where the substituents are independently selected from $R^4$,
  f) $(F)_p C_{1-3}$ alkyl,
  g) halogen,
  h) $OR^4$,
  i) $O(CH_2)_s OR^4$,
  i) $CO_2 R^4$,
  k) $(CO)NR^{10}R^{11}$,
  l) $O(CO)NR^{10}R^{11}$,
  m) $N(R^4)(CO)NR^{10}R^{11}$,
  n) $N(R^{10})(CO)R^{11}$,
  o) $N(R^{10})(CO)OR^{11}$,
  p) $SO_2 NR^{10}R^{11}$,
  q) $N(R^{10})SO_2 R^{11}$,
  r) $S(O)_m R^{10}$,
  s) CN,
  t) $NR^{10}R^{11}$,
  u) $N(R^{10})(CO)NR^4 R^{11}$, and
  v) $O(CO)R^4$;

or, any two independent $R^2$ on the same carbon or on adjacent carbons may be joined together to form a ring selected from cyclobutyl, cyclopentenyl, cyclopentyl, cyclohexenyl, cyclohexyl, thiazolinyl, oxazolinyl, imidazolinyl, imidazolidinyl, pyrrolinyl, morpholinyl, thiomorpholinyl, thiomorpholinyl S-oxide, thiomorpholinyl S-dioxide, azetidinyl, pyrrolidinyl, piperidinyl, tetrahydrofuranyl, tetrahydropyranyl, tetrahydropyridyl, furanyl, dihydrofuranyl, dihydropyranyl or piperazinyl, where said ring is unsubstituted or substituted with 1-5 substituents independently selected from:
        (a) —$C_{1-6}$alkyl, which is unsubstituted or substituted with 1-3 substituents independently selected from:
            (i) halo,
            (ii) hydroxy,
            (iii) —O—$C_{1-6}$alkyl,
            (iv) —$C_{3-6}$cycloalkyl,
            (v) —$COR^{10}$
            (vi) —$CO_2R^{10}$,
            (vii) —$NR^{10}R^{11}$,
            (viii) —$SO_2R^{10}$,
            (ix) —$CONR^{10}R^{11}$, and
            (x) —$(NR^{10})CO_2R^{11}$,
        (b) —$SO_2NR^{10}R^{11}$
        (c) halo,
        (d) —$SO_2R^{10}$,
        (e) hydroxy,
        (f) —O—$C_{1-6}$alkyl, which is unsubstituted or substituted with 1-5 halo,
        (g) —CN,
        (h) —$COR^{10}$,
        (i) —$NR^{10}R^{11}$,
        (j) —$CONR^{10}R^{11}$,
        (k) —$CO_2R^{10}$,
        (l) —$(NR^{10})CO_2R^{11}$,
        (m) —$O(CO)NR^{10}R^{11}$,
        (n) —$(NR^4)(CO)NR^{10}R^{11}$, and
        (o) oxo;

$R^{10}$ and $R^{11}$ are independently selected from: H, $C_{1-6}$ alkyl, $(F)_pC_{1-6}$ alkyl, $C_{3-6}$ cycloalkyl, aryl, heteroaryl, and benzyl, unsubstituted or substituted with halogen, hydroxy or $C_1$-$C_6$ alkoxy, where $R^{10}$ and $R^{11}$ may be joined together to form a ring selected from: azetidinyl, pyrrolidinyl, piperidinyl, piperazinyl, or morpholinyl, which is unsubstituted or substituted with 1-5 substituents where the substituents are independently selected from $R^4$;

$R^4$ is independently selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;

X is C or S;

Y is O, $(R^4)_2$, NCN, $NSO_2CH_3$, or $NCONH_2$, or Y is $O_2$ when X is S;

$R^5$ is independently selected from H and:
    1) $C_1$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
        a) $C_{1-6}$ alkyl,
        b) $C_{3-6}$ cycloalkyl,
        c) aryl, unsubstituted or substituted with 1-5 substituents where the substituents are independently selected from $R^4$,
        d) heteroaryl, unsubstituted or substituted with 1-5 substituents where the substituents are independently selected from $R^4$,
        e) heterocycle, unsubstituted or substituted with 1-5 substituents where the substituents are independently selected from $R^4$,
        f) $(F)_pC_{1-3}$ alkyl,
        g) halogen,
        h) $OR^4$,
        i) $O(CH_2)_sOR^4$,
        j) $CO_2R^4$,
        k) $(CO)NR^{10}R^{11}$,
        l) $O(CO)NR^{10}R^{11}$,
        m) $N(R^4)(CO)NR^{10}R^{11}$,
        n) $N(R^{10})(CO)R^{11}$,
        o) $N(R^{10})(CO)OR^{11}$,
        p) $SO_2NR^{10}R^{11}$,
        q) $N(R^{10})SO_2R^{11}$,
        r) $S(O)_mR^{10}$,
        s) CN,
        t) $NR^{10}R^{11}$,
        u) $N(R^{10})(CO)NR^4R^{11}$, and,
        v) $O(CO)R^4$;
    2) aryl or heteroaryl, unsubstituted or substituted with one or more substituents independently selected from:
        a) $C_{1-6}$ alkyl,
        b) $C_{3-6}$ cycloalkyl,
        c) aryl, unsubstituted or substituted with 1-5 substituents where the substituents are independently selected from $R^4$,
        d) heteroaryl, unsubstituted or substituted with 1-5 substituents where the substituents are independently selected from $R^4$,
        e) heterocycle, unsubstituted or substituted with 1-5 substituents where the substituents are independently selected from $R^4$,
        f) $(F)_pC_{1-3}$ alkyl,
        g) halogen,
        h) $OR^4$,
        i) $O(CH_2)_sOR^4$,
        j) $CO_2R^4$,
        k) $(CO)NR^{10}R^{11}$,
        l) $O(CO)NR^{10}R^{11}$,
        m) $N(R^4)(CO)NR^{10}R^{11}$,
        n) $N(R^{10})(CO)R^{11}$,
        o) $N(R^{10})(CO)OR^{11}$,
        p) $SO_2NR^{10}R^{11}$,
        q) $N(R^{10})SO_2R^{11}$,
        r) $S(O)_mR^{10}$,
        s) CN,
        t) $NR^{10}R^{11}$,
        u) $N(R^{10})(CO)NR^4R^{11}$, and
        v) $O(CO)R^4$;
    3) $C_{1-6}$ alkyl,
    4) $C_{3-6}$ cycloalkyl,
    5) aryl, unsubstituted or substituted with 1-5 substituents where the substituents are independently selected from $R^4$,
    6) heteroaryl, unsubstituted or substituted with 1-5 substituents where the substituents are independently selected from $R^4$,
    7) heterocycle, unsubstituted or substituted with 1-5 substituents where the substituents are independently selected from $R^4$, $(F)_pC_{1-3}$ alkyl,
    9) halogen,
    10) $OR^4$, 11) $O(CH_2)_sOR^4$,
12) $CO_2R^4$,
13) $(CO)NR^{10}R^{11}$,
14) $O(CO)NR^{10}R^{11}$,
15) $N(R^4)(CO)NR^{10}R^{11}$,
16) $N(R^{10})(CO)R^{11}$,
17) $N(R^{10})(CO)OR^{11}$,
18) $SO_2NR^{10}R^{11}$,
19) $N(R^{10})SO_2R^{11}$,
20) $S(O)_mR^{10}$,
21) CN,
22) $NR^{10}R^{11}$,
23) $N(R^{10})(CO)NR^4R^{11}$, and,
24) $O(CO)R^4$, or two $R^5$ attached to the same carbon form the substituent =O, such that $C(R^5)_2$ may be C=O,
  where the number of $R^5$ substituents that are not H, can range from zero to three;

G-J is selected from: N, C, $C=C(R^5)$, $N-C(R^5)_2$, C=N, $C(R^5)-C(R^5)_2$, $C(R^5)-N(R^6)$, $N(R^6)-N(R^6)$;

Q-T is selected from: $C(R^5)_2-C(R^5)_2$, $C(R^5)=C(R^5)$, $N=C(R^5)$, $C(R^5)=N$, N=N, N and $C(R^5)_2-(C=O)$, $N(R^6)-(C=O)$, $C(R^5)_2-N(R^6)$;

$R^3$ is independently selected from H, substituted or unsubstituted $C_1$-$C_3$ alkyl, CN and $CO_2R^4$;

p is 0 to 2q+1, for a substituent with q carbons;

m is 0, 1 or 2;

n is 0 or 1;

s is 1, 2 or 3;

wherein "heteroaryl" means a stable 5- to 7- membered monocyclic- or stable 8- to 11 -membered bicyclic heterocyclic ring system which is either saturated or unsaturated, and which consists of carbon atoms and from one to four heteroatoms selected from the group consisting of N, O, and S, and wherein the nitrogen and sulfur atoms may optionally be quaternized, and including any bicyclic group in which any of the above-defined heterocyclic rings is fused to a benzene ring;

and "heterocyclic" means a stable 5-to 7- membered monocyclic- or stable 9- to 10-membered fused bicyclic heterocyclic ring system which contains an aromatic ring, any ring of which may be saturated, and which consists of carbon atoms and from one to four heteroatoms selected from the group consisting of N, O, and S, and wherein the nitrogen and sulfur atoms may optionally be oxidized, and the nitrogen heteroatom may optionally be quaternized, and including any bicyclic group in which any of the above-defined heterocyclic rings is fused to a benzene ring; and or a pharmaceutically acceptable salt and individual diastereomers thereof.

2. A compound according to claim 1 having the Formula Ia:

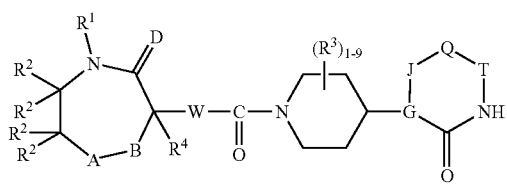

Ia wherein:
  A is a bond, $C(R^2)_2$, O, $S(O)_m$ or $NR^2$;
  B is $(C(R^2)_2)_n$;

D is O;
n is 0 or 1; and
or a pharmaceutically acceptable salt and individual stereoisomers thereof.

3. A compound according to claim 1 having the Formula Ib:

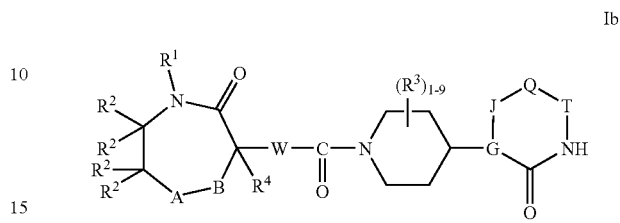

Ib wherein:
  A is a bond, $C(R^2)_2$, O, $S(O)_m$ or $NR^2$;
  B is $(C(R^2)_2)_n$;
  n is 0 or 1; and
or a pharmaceutically acceptable salt and individual stereoisomers thereof.

4. A compound according to claim 1 having the Formula Ic:

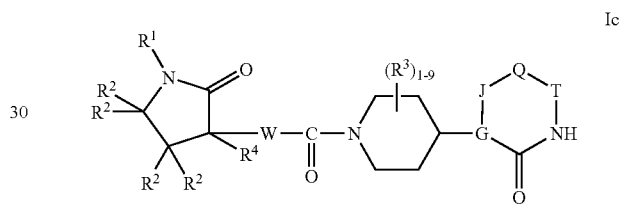

Ic or a pharmaceutically acceptable salt and individual stereoisomers thereof.

5. A compound according to claim 1 having the Formula Id:

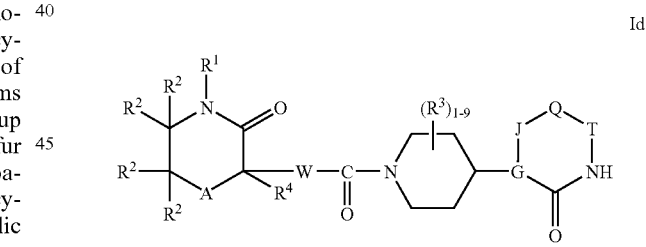

Id wherein:
  A is $C(R^2)_2$, O, $S(O)_m$ or $NR^2$;
or a pharmaceutically acceptable salt and individual stereoisomers thereof.

6. A compound according to claim 1 having the Formula Ie:

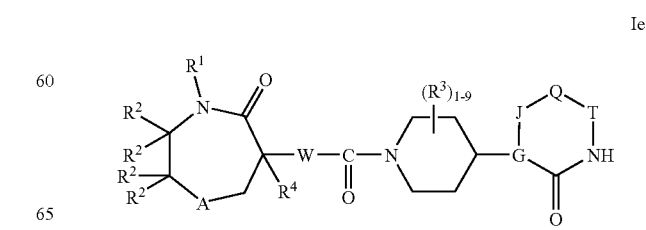

Ie wherein:

A is $C(R^2)_2$, O, $S(O)_m$ or $NR^2$;

or a pharmaceutically acceptable salt and individual stereoisomers thereof.

7. A compound according to claim 1 having the Formulae Ia-Ie, wherein:

$R^1$ is selected from:
1) H, $C_1$-$C_6$ alkyl, $C_{3-6}$ cycloalkyl and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) CN,
   l) $NR^{10}R^{11}$, and
   m) $O(CO)R^4$; and
2) aryl or heteroaryl, unsubstituted or substituted with one or more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$,
   k) CN,
   l) $NR^{10}R^{11}$, and,
   m) $O(CO)R^4$;

$R^2$ is selected from:
1) H, $C_0$-$C_6$ alkyl, $C_2$-$C_6$ alkynyl, $C_{3-6}$ cycloalkyl and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $S(O)_m R^4$,
   l) CN,
   m) $NR^{10}R^{11}$, and
   n) $O(CO)R^4$; and
2) aryl or heteroaryl, unsubstituted or substituted with one more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$,
   k) CN,
   l) $NR^{10}R^{11}$, and
   m) $O(CO)R^4$;

or, any two independent $R^2$ on the same carbon or on adjacent carbons may be joined together to form a ring selected from cyclobutyl, cyclopentenyl, cyclopentyl, cyclohexenyl, cyclohexyl, thiazolinyl, oxazolinyl, imidazolinyl, imidazolidinyl, pyrrolinyl, morpholinyl, thiomorpholinyl, thiomorpholinyl S-oxide, thiomorpholinyl S-dioxide, azetidinyl, pyrrolidinyl, piperidinyl, tetrahydrofuranyl, tetrahydropyranyl, tetrahydropyridyl, furanyl, dihydrofuranyl, dihydropyranyl or piperazinyl, where said ring is unsubstituted or substituted with 1-5 substituents independently selected from:
(a) —$C_{1-6}$alkyl, which is unsubstituted or substituted with 1-3 substituents independently selected from:
  (i) halo,
  (ii) hydroxy,
  (iii) —O—$C_{1-6}$alkyl,
  (iv) —$C_{3-6}$cycloalkyl,
  (v) —$COR^{10}$,
  (vi) —$CO_2 R^{10}$,
  (vii) —$NR^{10}R^{11}$,
  (viii) —$SO_2 R^{10}$,
  (ix) —$CONR^{10}R^{11}$, and
  (x) —$(NR^{10})CO_2 R^{11}$,
(b) —$SO_2 NR^{10}R^{11}$,
(c) halo,
(d) —$SO_2 R^{10}$,
(e) hydroxy,
(f) —O—$C_{1-6}$alkyl, which is unsubstituted or substituted with 1-5 halo,
(g) —CN,
(h) —$COR^{10}$,
(i) —$NR^{10}R^{11}$,
(j) —$CONR^{10}R^{11}$,
(k) —$CO_2 R^{10}$,
(l) —$(NR^{10})CO_2 R^{11}$,
(m) —$O(CO)NR^{10}R^{11}$,
(n) —$(NR^4)(CO)NR^{10}R^{11}$, and
(o) oxo;

$R^{10}$ and $R^{11}$ are independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ may be joined together to form a ring selected from: azetidinyl, pyrrolidinyl, piperidinyl, piperazinyl and morpholinyl, which is unsubstituted or substituted with 1-5 substituents where the substituents are independently selected from $R^4$ $R^4$ is independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;

G-J and Q-T are selected from the following pairings:
G-J is N and Q-T is $C(R^5)_2$—$C(R^5)_2$,
G-J is N, and Q-T is $C(R^5)$=$C(R^5)$,
G-J is N and Q-T is N=$C(R^5)$,
G-J is N, and Q-T is $C(R^5)$=N,
G-J is N, and Q-T is N=N,
G-J is C=$C(R^5)$, and Q-T is $N(R^6)$,
G-J is N, and Q-T is $C(R^5)_2$—(C=O)—,
G-J is N—$C(R^5)_2$, and Q-T is $C(R^5)_2$—$C(R^5)_2$,
G-J is C=$C(R^5)$ and Q-T is $C(R^5)$=$C(R^5)$,
G-J is C=$C(R^5)$, and Q-T is $C(R^5)$=N,
G-J is C=$C(R^5)$, and Q-T is N=$C(R^5)$,
G-J is C=N, and Q-T is $C(R^5)$=$C(R^5)$,
G-J is N—$C(R^5)_2$, and QT is $C(R^5)_2$—(C=O)—,
G-J is $C(R^5)$—$C(R^5)_2$, and QT is $N(R^6)$—(C=O)—,
G-J is $C(R^5)$—$C(R^5)_2$, and QT is $C(R^5)_2$—$C(R^5)_2$,
G-J is $C(R^5)$—$C(R^5)_2$, and QT is $C(R^5)_2$—$N(R^6)$,
G-J is $C(R^5)$—$N(R^6)$, and QT is $C(R^5)_2$—$C(R^5)_2$,
G-J is $C(R^5)$—$C(R^5)_2$, and QT is N=$C(R^5)$,
G-J is N—$C(R^5)_2$, and QT is $C(R^5)_2$—$N(R^6)$,
G-J is N—$N(R^6)$, and QT is $C(R^5)_2$—$C(R^5)_2$, and
G-J is N—$C(R^5)_2$, and QT is N=$C(R^5)$;

$R^5$ is independently selected from H and:
1) $C_1$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
  a) $C_{1-6}$ alkyl,
  b) $C_{3-6}$ cycloalkyl,
  c) aryl, unsubstituted or substituted with 1-5 substituents where the substituents are independently selected from $R^4$,
  d) heteroaryl, unsubstituted or substituted with 1-5 substituents where the substituents are independently selected from $R^4$,
  e) heterocycle, unsubstituted or substituted with 1-5 substituents where the substituents are independently selected from $R^4$,
  f) $(F)_p C_{1-3}$ alkyl,
  g) halogen,
  h) $OR^4$,
  i) $O(CH_2)_s OR^4$,
  j) $CO_2 R^4$,
  k) $(CO)NR^{10}R^{11}$,
  l) $O(CO)NR^{10}R^{11}$,
  m) $N(R^4)(CO)NR^{10}R^{11}$,
  n) $N(R^{10})(CO)R^{11}$,
  o) $N(R^{10})(CO)OR^{11}$,
  p) $SO_2 NR^{10}R^{11}$,
  q) $N(R^{10})SO_2 R^{11}$,
  r) $S(O)_m R^{10}$,
  s) CN,
  t) $NR^{10}R^{11}$,
  u) $N(R^{10})(CO)NR^4 R^{11}$, and
  v) $O(CO)R^4$;
2) aryl or heteroaryl, unsubstituted or substituted with one or more substituents independently selected from:
  a) $C_{1-6}$ alkyl,
  b) $C_{3-6}$ cycloalkyl,
  c) aryl, unsubstituted or substituted with 1-5 substituents where the substituents are independently selected from $R^4$,
  d) heteroaryl, unsubstituted or substituted with 1-5 substituents where the substituents are independently selected from $R^4$,
  e) heterocycle, unsubstituted or substituted with 1-5 substituents where the substituents are independently selected from $R^4$,
  f) $(F)_p C_{1-3}$ alkyl,
  g) halogen,
  h) $OR^4$,
  i) $O(CH_2)_s OR^4$,
  j) $CO_2 R^4$,
  k) $(CO)NR^{10}R^{11}$,
  l) $O(CO)NR^{10}R^{11}$,
  m) $N(R^4)(CO)NR^{10}R^{11}$,
  n) $N(R^{10})(CO)R^{11}$,
  o) $N(R^{10})(CO)OR^{11}$,
  p) $SO_2 NR^{10}R^{11}$,
  q) $N(R^{10})SO_2 R^{11}$,
  r) $S(O)_m R^{10}$,
  s) CN,
  t) $NR^{10}R^{11}$,
  u) $N(R^{10})(CO)NR^4 R^{11}$, and
  v) $O(CO)R^4$;
3) $C_{1-6}$ alkyl,
4) $C_{3-6}$ cycloalkyl,
5) aryl, unsubstituted or substituted with 1-5 substituents where the substituents are independently selected from $R^4$,
6) heteroaryl, unsubstituted or substituted with 1-5 substituents where the substituents are independently selected from $R^4$,
7) heterocycle, unsubstituted or substituted with 1-5 substituents where the substituents are independently selected from $R^4$,
8) $(F)_p C_{1-3}$ alkyl,
9) halogen,
10) $OR^4$,
11) $O(CH_2)_s OR^4$,
12) $CO_2 R^4$,
13) $(CO)NR^{10}R^{11}$,
14) $O(CO)NR^{10}R^{11}$,
15) $N(R^4)(CO)NR^{10}R^{11}$,
16) $N(R^{10})(CO)R^{11}$,
17) $N(R^{10})(CO)OR^{11}$,
18) $SO_2 NR^{10}R^{11}$,
19) $N(R^{10})SO_2 R^{11}$,
20) $S(O)_m R^{10}$,
21) CN,
22) $NR^{10}R^{11}$,
23) $N(R^{10})(CO)NR^4 R^{11}$, and,
24) $O(CO)R^4$, or two $R^5$ attached to the same carbon form the substituent =O, such that $C(R^5)_2$ may be C=O, where the number of $R^5$ substituents that are not H, can range from zero to three;

$R^3$ is independently selected from H, substituted or unsubstituted $C_1$-$C_3$ alkyl, CN and $CO_2 R^4$;

p is 0 to 2q+1, for a substituent with q carbons
m is 0 to 2;
s is 1 to 3;
or a pharmaceutically acceptable salt and individual stereoisomers thereof.

8. The compound of Formula II:

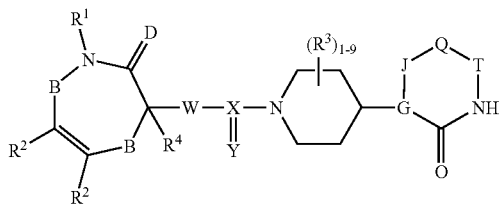

wherein:
B is independently $(C(R^2)_2)_n$;
D is O;
$R^1$ is selected from:
1) H, $C_1$-$C_6$ alkyl, $C_2$-$C_6$ alkenyl, $C_2$-$C_6$ alkynyl, $C_{3-6}$ cycloalkyl, and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_pC_{1-3}$ alkyl,
   g) halogen,
   h) $OR^4$,
   i) $O(CH_2)_sOR^4$,
   j) $CO_2R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2NR^{10}R^{11}$,
   q) $N(R^{10})SO_2R^{11}$,
   r) $S(O)_mR^{10}$,
   s) CN,
   t) $NR^{10}R^{11}$,
   u) $N(R^{10})(CO)NR^4R^{11}$, and
   v) $O(CO)R^4$;
2) aryl or heteroaryl, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_pC_{1-3}$ alkyl,
   g) halogen,
   h) $OR^4$,
   i) $O_{(CH2)s}OR^4$,
   j) $CO_2R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2NR^{10}R^{11}$,
   q) $N(R^{10})SO_2R^{11}$,
   r) $S(O)_mR^{10}$,
   s) CN,
   x) $NR^{10}R^{11}$,
   y) $N(R^{10})(CO)NR^4R^{11}$, and
   v) $O(CO)R^4$;
$R^2$ is independently selected from:
1) H, $C_0$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_pC_{1-3}$ alkyl,
   g) halogen,
   h) $OR^4$,
   i) $O(CH_2)_sOR^4$,
   j) $CO_2R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2NR^{10}R^{11}$,
   q) $N(R^{10})SO_2R^{11}$,
   r) $S(O)_mR^{10}$,
   s) CN,
   t) $NR^{10}R^{11}$,
   u) $N(R^{10})(CO)NR^4R^{11}$, and,
   v) $O(CO)R^4$;
2) aryl or heteroaryl, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_pC_{1-3}$ alkyl,
   g) halogen,
   h) $OR^4$,
   i) $O(CH_2)_sOR^4$,
   j) $CO_2R^4$,
   k) $(CO)NR^{10}R^{11}$,
   l) $O(CO)NR^{10}R^{11}$, m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$, and
v) $O(CO)R^4$;

or, the independent $R^2$ on adjacent carbons may be joined together to form a ring selected from cyclopentenyl, cyclohexenyl, phenyl, naphthyl, thienyl, thiazolyl, thiazolinyl, oxazolyl, oxazolinyl, imidazolyl, imidazolinyl, pyridyl, pyrimidyl, pyrazinyl, pyrrolyl, pyrrolinyl, tetrahydropyridyl, furanyl, dihydrofuranyl and dihydropyranyl, where said ring is unsubstituted or substituted with 1-5 substituents independently selected from:
(a) —$C_{1-6}$alkyl, which is unsubstituted or substituted with 1-3 substituents where the substituents are independently selected from:
(i) halo,
(ii) hydroxy,
(iii) —O—C1-6alkyl,
(iv) —C3-6cycloalkyl,
(v) —COR10
(vi) —CO2R10,
(vii) —NR10R11,
(viii) —SO2R10,
(ix) —CONR10R11, and
(x) —(NR10)CO2R11,
(b) —SO2NR10R11
(c) halo,
(d)—SO2R10,
(e) hydroxy,
(f) —O—C1-6alkyl, which is unsubstituted or substituted with 1-5 halo,
(g) —CN,
(h) —COR10,
(i) —NR10R11,
(j)—CONR10R11,
(k) —CO2R10,
(l) —(NR10)CO2R11,
(m) —O(CO)NR10R11,
(n) —(NR4)(CO)NR10R11, and
(o) oxo;

$R^{10}$ and $R^{11}$ are independently selected from: H, $C_{1-6}$ alkyl, $(F)_pC_{1-6}$ alkyl, $C_{3-6}$ cycloalkyl, aryl, heteroaryl, and benzyl, unsubstituted or substituted with halogen, hydroxy or $C_1$-$C_6$ alkoxy, where $R^{10}$ and $R^{11}$ may be joined together to form a ring selected from: azetidinyl, pyrrolidinyl, piperidinyl, piperazinyl, or morpholinyl, which is unsubstituted or substituted with 1-5 substituents where the substituents are independently selected from $R^4$;

$R^4$ is independently selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;
X is C or S;
Y is O, $(R^4)_2$, NCN, $NSO_2CH_3$ or $NCONH_2$, or Y is $O_2$ when X is S;

$R^5$ is independently selected from H and:
1) $C_1$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
a) $C_{1-6}$ alkyl,
b) $C_{3-6}$ cycloalkyl,
c) aryl, unsubstituted or substituted with 1-5 substituents where the substituents are independently selected from $R^4$,
d) heteroaryl, unsubstituted or substituted with 1-5 substituents where the substituents are independently selected from $R^4$,
e) heterocycle, unsubstituted or substituted with 1-5 substituents where the substituents are independently selected from $R^4$,
f) $(F)_pC_{1-3}$ alkyl,
g) halogen,
h) $OR^4$,
i) $O(CH_2)_sOR^4$,
j) $CO_2R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$, and,
v) $O(CO)R^4$;

2) aryl or heteroaryl, unsubstituted or substituted with one or more substituents independently selected from:
a) $C_{1-6}$ alkyl,
b) $C_{3-6}$ cycloalkyl,
c) aryl, unsubstituted or substituted with 1-5 substituents where the substituents are independently selected from $R^4$,
d) heteroaryl, unsubstituted or substituted with 1-5 substituents where the substituents are independently selected from $R^4$,
e) heterocycle, unsubstituted or substituted with 1-5 substituents where the substituents are independently selected from $R^4$,
f) $(F)_pC_{1-3}$ alkyl,
g) halogen,
h) $OR^4$,
i) $O(CH_2)_sOR^4$,
j) $CO_2R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$, and
v) $O(CO)R^4$;

3) $C_{1-6}$ alkyl,
4) $C_{3-6}$ cycloalkyl, 5) aryl, unsubstituted or substituted with 1-5 substituents where the substituents are independently selected from $R^4$,
6) heteroaryl, unsubstituted or substituted with 1-5 substituents where the substituents are independently selected from $R^4$,
7) heterocycle, unsubstituted or substituted with 1-5 substituents where the substituents are independently selected from $R^4$,
8) $(F)_p C_{1-3}$ alkyl,
9) halogen,
10) $OR^4$,
11) $O(CH_2)_s OR^4$,
12) $CO_2 R^4$,
13) $(CO)NR^{10}R^{11}$,
14) $O(CO)NR^{10}R^{11}$,
15) $N(R^4)(CO)NR^{10}R^{11}$,
16) $N(R^{10})(CO)R^{11}$,
17) $N(R^{10})(CO)OR^{11}$,
18) $SO_2 NR^{10}R^{11}$,
19) $N(R^{10})SO_2 R^{11}$,
20) $S(O)_m R^{10}$,
21) CN,
22) $NR^{10}R^{11}$,
23) $N(R^{10})(CO)NR^4 R^{11}$, and,
24) $O(CO)R^4$, or two $R^5$ attached to the same carbon form the substituent =O, such that $C(R^5)_2$ may be C=O, where the number of $R^5$ substituents that are not H, can range from zero to three;

G-J is selected from: N, C, C=C($R^5$), N—C($R^5$)$_2$, C=N, C($R^5$)—C($R^5$)$_2$, C($R^5$)—N($R^6$), N($R^6$)—N($R^6$);

Q-T is selected from: C($R^5$)$_2$—C($R^5$)$_2$, C($R^5$)=C($R^5$), N=C($R^5$), C($R^5$)=N, N=N, N and C($R^5$)$_2$—(C=O), N($R^6$)—(C=O), C($R^5$)$_2$—N($R^6$);

$R^3$ is independently selected from H, substituted or unsubstituted $C_1$-$C_3$ alkyl, CN and $CO_2 R^4$;

p is 0 to 2q+1, for a substituent with q carbons;

m is 0, 1 or 2;

n is 0 or 1;

s is 1, 2 or 3;

wherein "heteroaryl" means a stable 5- to 7- membered monocyclic- or stable 8- to 11-membered bicyclic heterocyclic ring system which is either saturated or unsaturated, and which consists of carbon atoms and from one to four heteroatoms selected from the group consisting of N, O, and S, and wherein the nitrogen and sulfur atoms may optionally be quaternized, and including any bicyclic group in which any of the above-defined heterocyclic rings is fused to a benzene ring;

and "heterocyclic" means a stable 5-to 7- membered monocyclic- or stable 9-to 10-membered fused bicyclic heterocyclic ring system which contains an aromatic ring, any ring of which may be saturated, and which consists of carbon atoms and from one to four heteroatoms selected from the group consisting of N, O, and S, and wherein the nitrogen and sulfur atoms may optionally be oxidized, and the nitrogen heteroatom may optionally be quaternized, and including any bicyclic group in which any of the above-defined heterocyclic rings is fused to a benzene ring; and or a pharmaceutically acceptable salt and individual diastereomers thereof.

9. A compound according to claim 8, wherein:

$R^1$ is selected from:

1) H, $C_1$-$C_6$ alkyl, $C_{3-6}$ cycloalkyl and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) CN,
   l) $NR^{10}R^{11}$, and
   m) $O(CO)R^4$; and 2) aryl or heteroaryl, unsubstituted or substituted with one or more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$,
   k) CN,
   l) $NR^{10}R^{11}$, and,
   m) $O(CO)R^4$;

$R^2$ is selected from:

1) H, $C_0$-$C_6$ alkyl, $C_2$-$C_6$ alkynyl, $C_{3-6}$ cycloalkyl and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $S(O)_m R^4$,
   l) CN,
   m) $NR^{10}R^{11}$, and
   n) $O(CO)R^4$; and 2) aryl or heteroaryl, unsubstituted or substituted with one more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$, g) $(CO)NR^{10}R^{11}$,
h) $SO_2NR^{10}R^{11}$,
i) $N(R^{10})SO_2R^{11}$,
j) $S(O)_mR^4$,
k) CN,
l) $NR^{10}R^{11}$, and
m) $O(CO)R^4$;

$R^{10}$ and $R^{11}$ are independently selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ may be joined together to form a ring selected from: azetidinyl, pyrrolidinyl, piperidinyl, piperazinyl and morpholinyl, which is unsubstituted or substituted with 1-5 substituents where the substituents are independently selected from $R^4$ $R^4$ is independently selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;

G-J and Q-T are selected from the following pairings:
G-J is N and Q-T is $C(R^5)_2$—$C(R^5)_2$,
G-J is N, and Q-T is $C(R^5)$=$C(R^5)$,
G-J is N and Q-T is N=$C(R^5)$,
G-J is N, and Q-T is $C(R^5)$=N,
G-J is N, and Q-T is N=N,
G-J is C=$C(R^5)$, and Q-T is $N(R^6)$,
G-J is N, and Q-T is $C(R^5)_2$—(C=O)—,
G-J is N—$C(R^5)_2$, and Q-T is $C(R^5)_2$—$C(R^5)_2$,
G-J is C=$C(R^5)$ and Q-T is $C(R^5)$=$C(R^5)$,
G-J is C=$C(R^5)$, and Q-T is $C(R^5)$=N,
G-J is C=$C(R^5)$, and Q-T is N=$C(R^5)$,
G-J is C=N, and Q-T is $C(R^5)$=$C(R^5)$,
G-J is N—$C(R^5)_2$, and QT is $C(R^5)_2$—(C=O)—,
G-J is $C(R^5)$—$C(R^5)_2$, and QT is $N(R^6)$—(C=O)—,
G-J is $C(R^5)$—$C(R^5)_2$, and QT is $C(R^5)_2$—$C(R^5)_2$,
G-J is $C(R^5)$—$C(R^5)_2$, and QT is $C(R^5)_2$—$N(R^6)$,
G-J is $C(R^5)$—$N(R^6)$, and QT is $C(R^5)_2$—$C(R^5)_2$,
G-J is $C(R^5)$—$C(R^5)_2$, and QT is N=$C(R^5)$,
G-J is N—$C(R^5)_2$, and QT is $C(R^5)_2$—$N(R^6)$,
G-J is N—$N(R^6)$, and QT is $C(R^5)_2$—$C(R^5)_2$, and
G-J is N—$C(R^5)_2$, and QT is N=$C(R^5)$;

$R^5$ is independently selected from H and:
1) $C_1$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
  a) $C_{1-6}$ alkyl,
  b) $C_{3-6}$ cycloalkyl,
  c) aryl, unsubstituted or substituted with 1-5 substituents where the substituents are independently selected from $R^4$,
  d) heteroaryl, unsubstituted or substituted with 1-5 substituents where the substituents are independently selected from $R^4$,
  e) heterocycle, unsubstituted or substituted with 1-5 substituents where the substituents are independently selected from $R^4$,
  f) $(F)_pC_{1-3}$ alkyl,
  g) halogen,
  h) $OR^4$,
  i) $O(CH_2)_sOR^4$,
  j) $CO_2R^4$,
  k) $(CO)NR^{10}R^{11}$,
  l) $O(CO)NR^{10}R^{11}$,
  m) $N(R^4)(CO)NR^{10}R^{11}$,
  n) $N(R^{10})(CO)R^{11}$,
  o) $N(R^{10})(CO)OR^{11}$,
  p) $SO_2NR^{10}R^{11}$,
  q) $N(R^{10})SO_2R^{11}$,
  r) $S(O)_mR^{10}$,
  s) CN,
  t) $NR^{10}R^{11}$,
  u) $N(R^{10})(CO)NR^4R^{11}$, and,
  v) $O(CO)R^4$;
2) aryl or heteroaryl, unsubstituted or substituted with one or more substituents independently selected from:
  a) $C_{1-6}$ alkyl,
  b) $C_{3-6}$ cycloalkyl,
  c) aryl, unsubstituted or substituted with 1-5 substituents where the substituents are independently selected from $R^4$,
  d) heteroaryl, unsubstituted or substituted with 1-5 substituents where the substituents are independently selected from $R^4$,
  e) heterocycle, unsubstituted or substituted with 1-5 substituents where the substituents are independently selected from $R^4$,
  f) $(F)_pC_{1-3}$ alkyl,
  g) halogen,
  h) $OR^4$,
  i) $O(CH_2)_sOR^4$,
  j) $CO_2R^4$,
  k) $(CO)NR^{10}R^{11}$,
  l) $O(CO)NR^{10}R^{11}$,
  m) $N(R^4)(CO)NR^{10}R^{11}$,
  n) $N(R^{10})(CO)R^{11}$,
  o) $N(R^{10})(CO)OR^{11}$,
  p) $SO_2NR^{10}R^{11}$,
  q) $N(R^{10})SO_2R^{11}$,
  r) $S(O)_mR^{10}$,
  s) CN,
  t) $NR^{10}R^{11}$,
  u) $N(R^{10})(CO)NR^4R^{11}$, and
  v) $O(CO)R^4$;
3) $C_{1-6}$ alkyl,
4) $C_{3-6}$ cycloalkyl,
5) aryl, unsubstituted or substituted with 1-5 substituents where the substituents are independently selected from $R^4$,
6) heteroaryl, unsubstituted or substituted with 1-5 substituents where the substituents are independently selected from $R^4$,
7) heterocycle, unsubstituted or substituted with 1-5 substituents where the substituents are independently selected from $R^4$,
8) $(F)_pC_{1-3}$ alkyl,
9) halogen,
10) $OR^4$,
11) $O(CH_2)_sOR^4$,
12) $CO_2R^4$,
13) $(CO)NR^{10}R^{11}$,
14) $O(CO)NR^{10}R^{11}$,
15) $N(R^4)(CO)NR^{10}R^{11}$,
16) $N(R^{10})(CO)R^{11}$,
17) $N(R^{10})(CO)OR^{11}$,
18) $SO_2NR^{10}R^{11}$,
19) $N(R^{10})SO_2R^{11}$,
20) $S(O)_mR^{10}$,
21) CN, 22) $NR^{10}R^{11}$,
23) $N(R^{10})(CO)NR^4R^{11}$, and,
24) $O(CO)R^4$, or two $R^5$ attached to the same carbon form the substituent =O, such that $C(R^5)_2$ may be C=O, where the number of $R^5$ substituents that are not H, can range from zero to three;

$R^3$ is independently selected from H, substituted or unsubstituted $C_1$-$C_3$ alkyl, CN and $CO_2R^4$;

p is 0 to 2q+1, for a substituent with q carbons m is 0 to 2;

s is 1 to 3;

or a pharmaceutically acceptable salt and individual stereoisomers thereof.

10. A compound selected from the group consisting of:

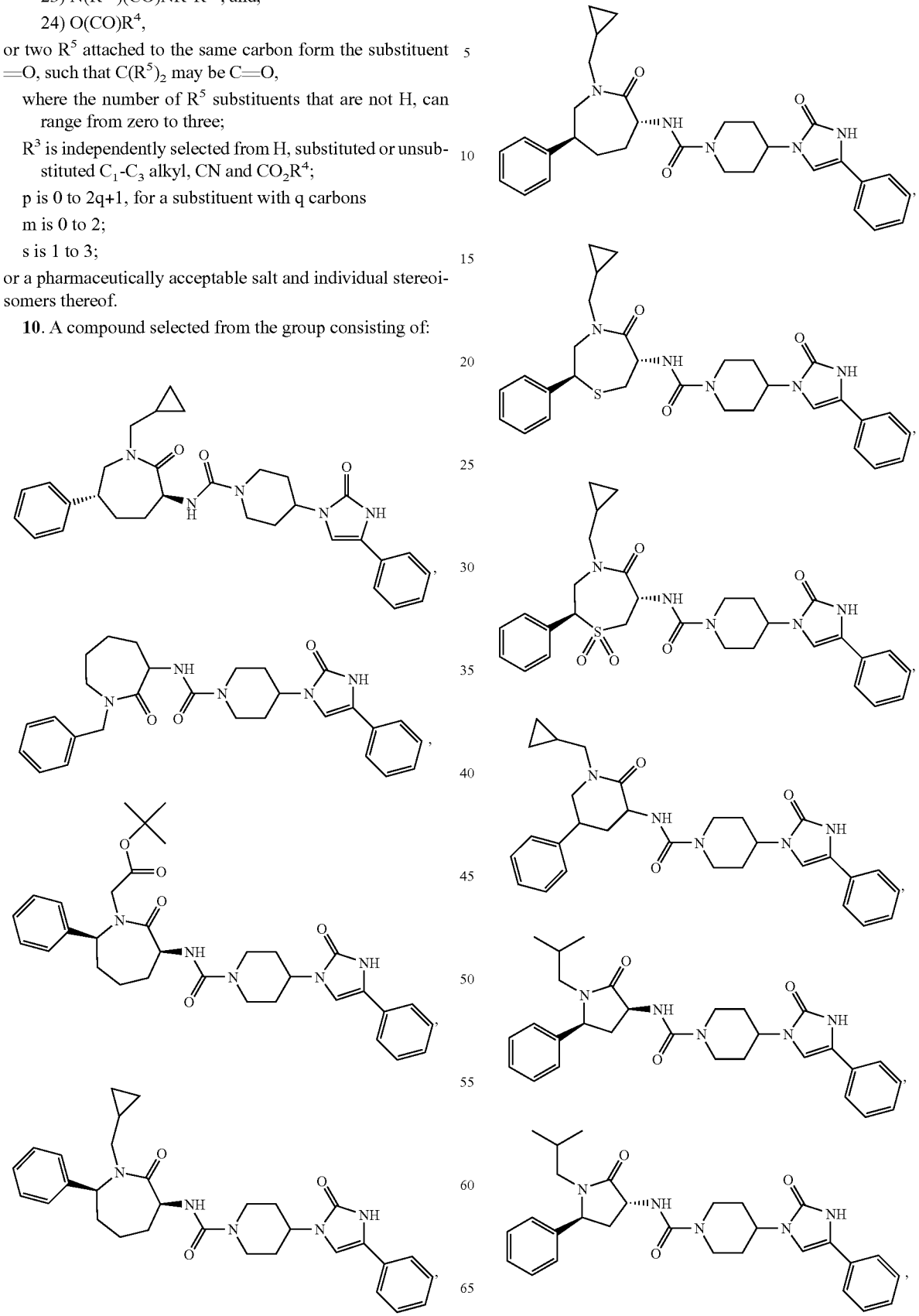

-continued
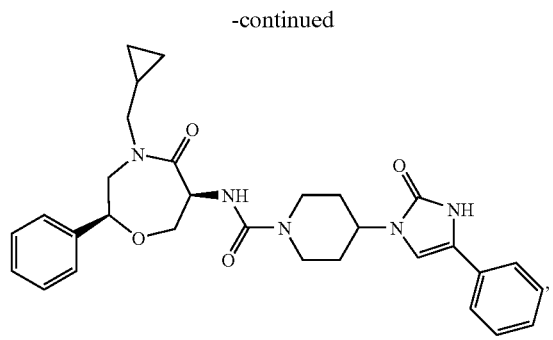
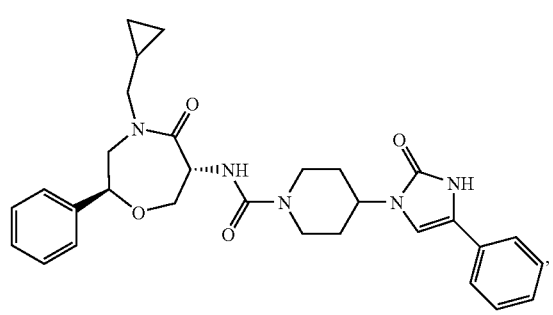
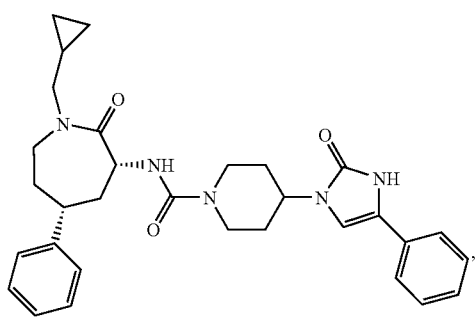
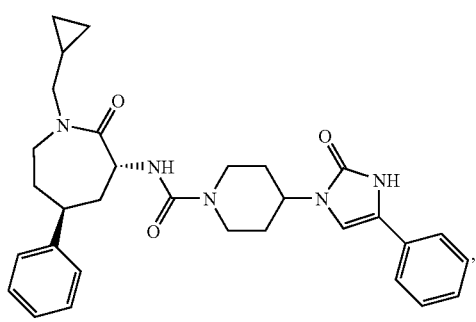
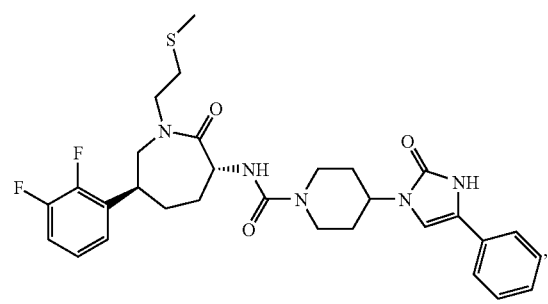
-continued
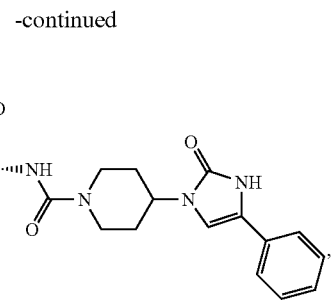
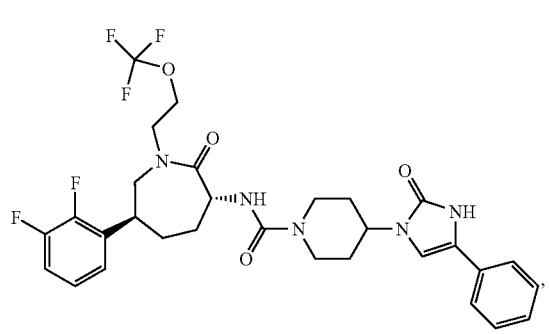
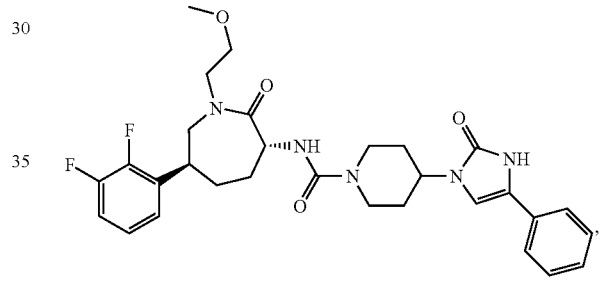
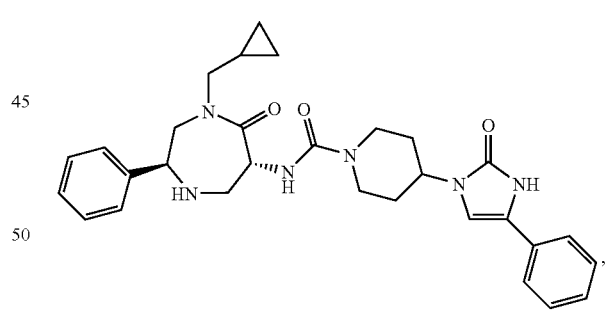
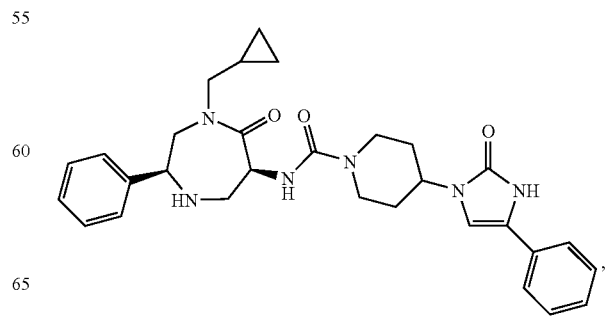

105
-continued
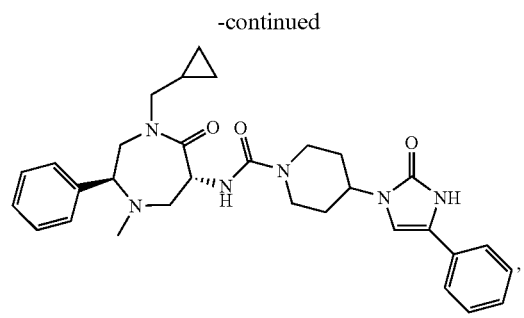
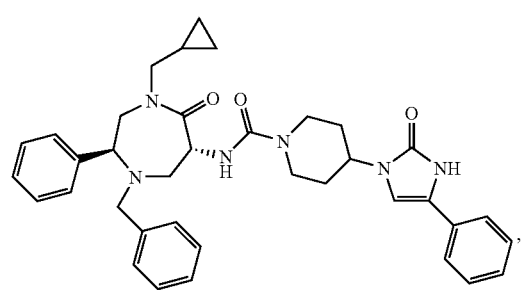
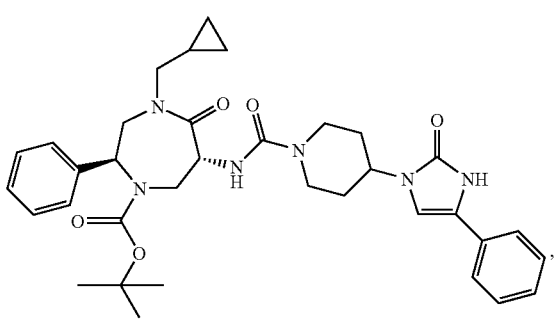
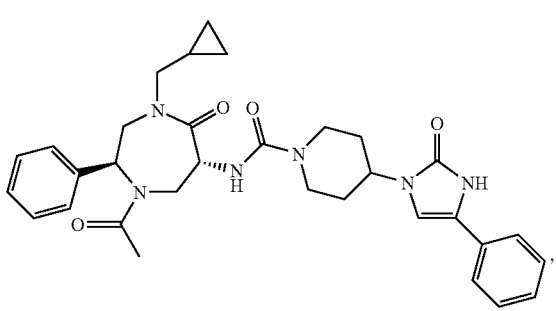
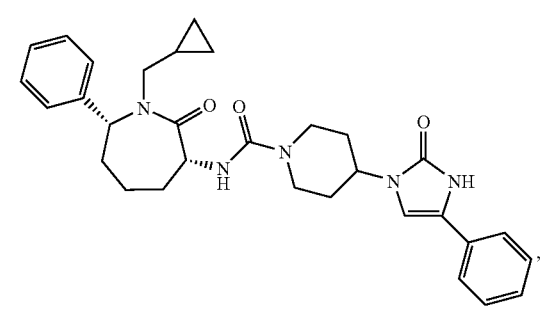
106
-continued
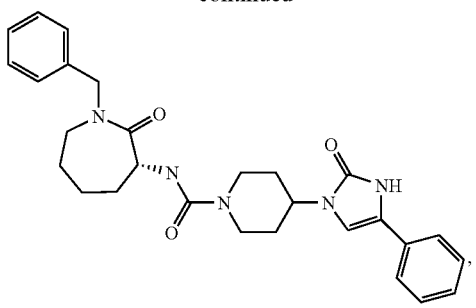
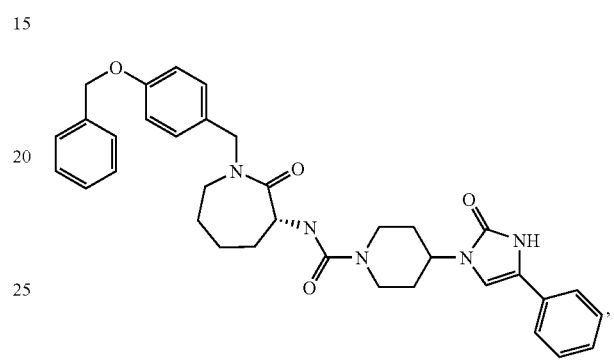
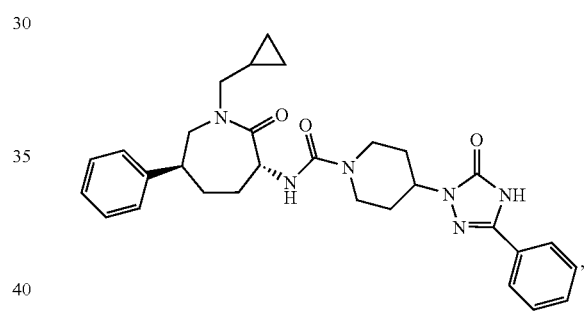
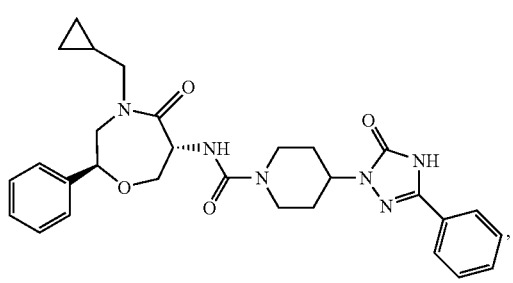
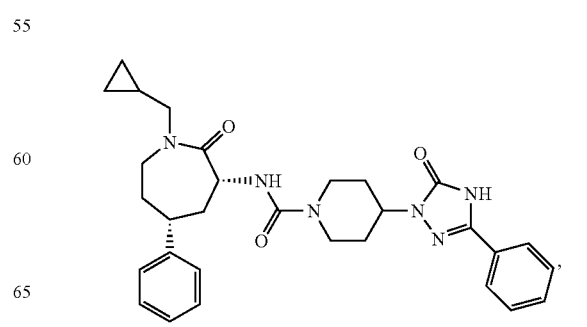

-continued

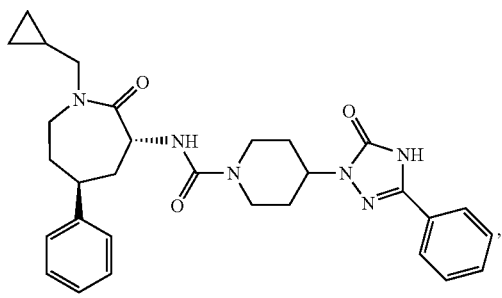

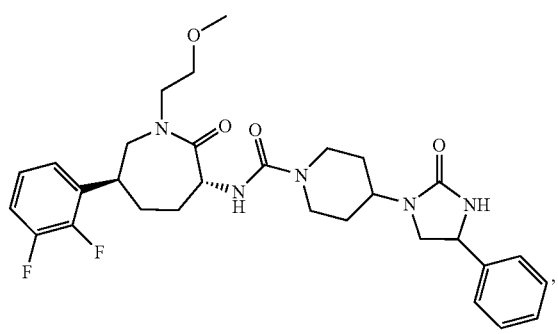

-continued

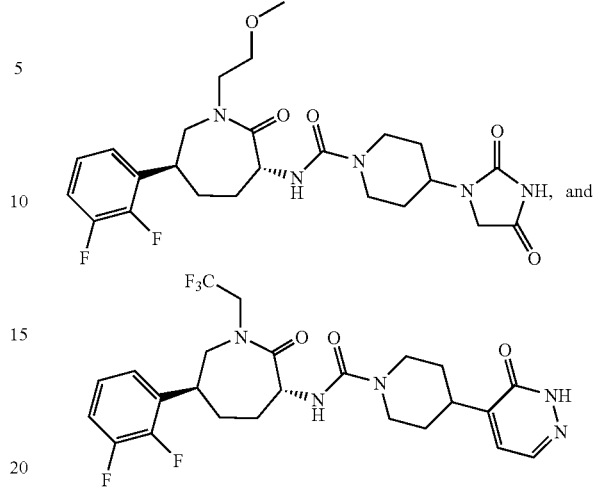

or a pharmaceutically acceptable salt and individual diastereomers thereof.

11. A pharmaceutical composition which comprises an inert carrier and the compound of claim 1.

12. A method for treating headache in a mammalian patient in need of such which comprises administering to the patient a therapeutically effective amount of the compound of claim 1.

* * * * *

UNITED STATES PATENT AND TRADEMARK OFFICE
CERTIFICATE OF CORRECTION

PATENT NO. : 7,491,713 B2
APPLICATION NO. : 10/587121
DATED : February 17, 2009
INVENTOR(S) : Christopher S. Burgey et al.

It is certified that error appears in the above-identified patent and that said Letters Patent is hereby corrected as shown below:

Please delete text at col. 87, lines 31 to 49, and replace with:

wherein "heterocycle" means a stable 5- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur atoms may optionally be quaternized, and including any bicyclic group in which any of the above-defined heterocyclic rings is fused to a benzene ring;

and "heteroaryl" means a stable 5- to 7-membered monocyclic- or stable 9- to 10-membered fused bicyclic heterocyclic ring system which contains an aromatic ring, any ring of which may be saturated, and which consists of carbon atoms and from one to four heteroatoms selected from the group consisting of N, O and S, and wherein the nitrogen and sulfur atoms may optionally be oxidized, and the nitrogen heteroatom may optionally be quaternized, and including any bicyclic group in which any of the above-defined heterocyclic rings is fused to a benzene ring; and Please delete text at col. 93, line 67, and replace with:
  i)  $O(CH_2)_s)OR^4$, Please delete text at col. 95, lines 25 to 49, and replace with:
    (iii)  -O-$C_{1-6}$alky,
    (iv)  -$C_{3-6}$cycloaklyl,
    (v)  -$COR^{10}$,
    (vi)  -$CO_2R^{10}$;
    (vii)  -$NR^{10}R^{11}$,
    (viii)  -$SO_2R^{10}$,
    (ix)  -$CONR^{10}R^{11}$, and
    (x)  -$(NR^{10})CO_2R^{11}$,
 (b)  -$SO_2NR^{10}R^{11}$,
 (c)  halo,
 (d)  -$SO_2R^{10}$,
 (e)  hydroxy,
 (f)  -O-$C_{1-6}$alkyl, which is unsubstituted or substituted with 1-5 halo,
 (g)  -CN
 (h)  -$COR^{10}$,

UNITED STATES PATENT AND TRADEMARK OFFICE
CERTIFICATE OF CORRECTION

PATENT NO.        : 7,491,713 B2
APPLICATION NO. : 10/587121
DATED             : February 17, 2009
INVENTOR(S)       : Christopher S. Burgey et al.

It is certified that error appears in the above-identified patent and that said Letters Patent is hereby corrected as shown below:

CONTINUED:

(i)   $-NR^{10}R^{11}$,
(j)   $-CONR^{10}R^{11}$,
(k)   $-CO_2R^{10}$,
(l)   $-(NR^{10})CO_2R^{11}$,
(m)   $-O(CO)NR^{10}R^{11}$,
(n)   $-(NR^4)(CO)NR^{10}R^{11}$, and Please delete text at col. 97, lines 42 to 60, and replace with:

wherein "heterocycle" means a stable 5- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur atoms may optionally be quaternized, and including any bicyclic group in which any of the above-identified heterocyclic rings is fused to a benzene ring;

and "heteroaryl" means a stable 5- to 7-membered monocyclic- or stable 9- to 10-membered fused bicyclic heterocyclic ring system which contains an aromatic ring, any ring of which may be saturated, and which consists of carbon atoms and from one to four heteroatoms selected from the group consisting of N, O and S, and wherein the nitrogen and sulfur atoms may optionally be oxidized, and the nitrogen heteroatom may optionally be quaternized, and including any bicyclic group in which any of the above-defined heterocyclic rings is fused to a benzene ring; and Signed and Sealed this Twenty-second Day of September, 2009

David J. Kappos
*Director of the United States Patent and Trademark Office*